US006891021B2

(12) United States Patent
Crabtree et al.

(10) Patent No.: US 6,891,021 B2
(45) Date of Patent: May 10, 2005

(54) REGULATED APOPTOSIS

(75) Inventors: Gerald R. Crabtree, Woodside, CA (US); Stuart L. Schreiber, Cambridge, MA (US); David M. Spencer, Los Altos, CA (US); Thomas J. Wandless, Cambridge, MA (US); Peter Belshaw, Somerville, MA (US)

(73) Assignees: Board of Trustees of the Leland Stanford Junior University, Stanford, CA (US); President and Fellows of Harvard College, Cambridge, MA (US)

( * ) Notice: Subject to any disclaimer, the term of this patent is extended or adjusted under 35 U.S.C. 154(b) by 175 days.

(21) Appl. No.: 10/054,712

(22) Filed: Nov. 13, 2001

(65) Prior Publication Data

US 2004/0024725 A1 Feb. 5, 2004

Related U.S. Application Data

(63) Continuation of application No. 09/302,629, filed on Apr. 30, 1999, now Pat. No. 6,316,418, which is a continuation of application No. 09/087,811, filed on May 29, 1998, now Pat. No. 6,054,436, which is a continuation of application No. 08/292,597, filed on Aug. 18, 1994, now Pat. No. 5,834,266, which is a continuation-in-part of application No. 08/179,143, filed on Jan. 7, 1994, now abandoned, which is a continuation-in-part of application No. 08/093,499, filed on Jul. 16, 1993, now abandoned, said application No. 09/302,629, is a continuation-in-part of application No. 08/196,043, filed on Feb. 11, 1994, now abandoned, which is a continuation-in-part of application No. 08/179,748, filed on Jan. 7, 1994, now abandoned, which is a continuation-in-part of application No. 08/092,977, filed on Jul. 16, 1993, now abandoned, which is a continuation-in-part of application No. 08/017,931, filed on Feb. 12, 1993, now abandoned.

(51) Int. Cl.$^7$ .............................. C07K 2/00; C07K 4/00
(52) U.S. Cl. ........................ 530/350; 530/300; 435/7.1; 435/7.2
(58) Field of Search ................................ 530/300, 350; 435/7.1, 7.2

(56) References Cited

U.S. PATENT DOCUMENTS

| 5,171,671 A | | 12/1992 | Evans et al. | |
|---|---|---|---|---|
| 5,834,266 A | * | 11/1998 | Crabtree et al. | ............ 435/456 |
| 6,054,436 A | | 4/2000 | Crabtree et al. | |

FOREIGN PATENT DOCUMENTS

| EP | 0 594 847 | 5/1994 |
|---|---|---|
| WO | WO 92/01052 | 1/1992 |
| WO | WO 93/23550 | 11/1993 |
| WO | WO 93/25533 | 12/1993 |

OTHER PUBLICATIONS

Alberg, D.G and Schreiber, S.L. Structure–Based Design of a Cyclophilin–Calcineurin Bridging Ligand. *Science* 262, 248–250 (1993).

Albers, M.W. et al. Substrate Specificity for the Human Rotamase FKBP: A View of FK506 and Rapamycin as Leucine (twisted amide)–Proline Mimics. *J. Org. Chem.* 55, 4984–4986 (1990).

Albers, M.W. et al. Relationship of FKBP to PDCI–1. *Nature* 351, 527 (1991).

Albers, M.W. et al. FKBP, Thought to be Identical to PKCI–2, Does Not Inhibit Protein Kinase C. *BioMed. Chem. Lett.* 1, 205–210 (1991).

Albers, M.W. et al. An FKBP–Rapamycin Sensitive, Cyclin–Dependent Kinase Activity That Correlates with the FKBP Rapamycin–Induced G1 Arrest Point in MG–63 Cells. *Annals of N. Y. Acad. Sci.* 696, 54–62 (1993).

Andrus, M.B. and Schreiber, S.L. Structure–Based Design of an Acyclic Ligand That Bridges FKBP12 and Calcineurin. *J. Am. Chem. Soc.* 115, 10420–10421 (1993).

Ben–Levy, R. et al. A oncogenic point mutation confers High Affinity Ligand Binding to the neu Receptor. *J. Biol. Chem.* 267, 17304–17313 (1992).

Bergsma, D.J. et al. The Cyclophilin Multigene Family of Peptidyl–Prolyl Isomerases. *J. Biol. Chem.* 266, 23204–23214 (1991).

Bernard, O. et al. High–affinity Interleukin–2 Binding by an Oncogenic Hybrid Interleukin–2 Epidermal Growth Factor Receptor Molecule. *PNAS* 84, 2125–2129 (1987).

Bierer, B.E. et al. Mechanisms of Immunosuppression by FK506: Preservation of T Cell Transmembrane Signal Transduction. *Transplantation* 49, 1168–1202 (1990).

Bierer, B.E. et al. Probing Immunosuppressant Action with a Nonnatural Immunosuppressive Ligand. *Science* 250, 556–559 (Oct. 26 1990).

Bierer, B.E. et al, Two Distinct Signal Transmission Pathways in T Lymphocytes are Inhibited by Complexes Formed Between an Immunophilin and Either FK506 or Rapamycin. *PNAS* 87, 9231–9235 (Dec. 1990).

Bierer, B.E. et al, The Effect of the Immunosuppressant FK506 on Alternate Pathways of T Cell Activation. *Eur. J. Immunol.* 21, 439–445 (1991).

Bonnerot, C. et al. Role of associated γ–chain in Tyrosine Kinase Activation via Murine FcRIII. *EMBO J.* 11, 2747–2757 (1992).

Bram, R.J. et al. Identification of the Immunophilins Capable of Mediating Inhibition of Signal Transduction by Cyclosporin A and FK506: Roles of Calcineurin Binding and Cellular Location. *Mol. Cell. Biol.* 13, 4760–4769 (Aug. 1993).

(Continued)

*Primary Examiner*—James Ketter
*Assistant Examiner*—David A. Lambertson
(74) *Attorney, Agent, or Firm*—Ropes & Gray LLP

(57) ABSTRACT

We have developed a general procedure for the regulated (inducible) dimerization or oligomerization of intracellular proteins and disclose methods and materials for using that procedure to regulatably initiate cell-specific apoptosis (programmed cell death) in genetically engineered cells

12 Claims, 32 Drawing Sheets

OTHER PUBLICATIONS

Byrn, R.A. et al. Biological Properties of a CD4 Immunoadhesin. *Nature* 344, 667–670 (Apr. 12 1990).

Cantley, L.C. et al. Oncogenes and signal transduction. *Cell* 64, 281–302 (Jan. 25 1991).

Chan, A.C. et al. The ζ Chain is associated with a Tyrosine Kinase and upon T–Cell Antigen Receptor Stimulation Associates with ZAP–70, a 70–kDa Tyrosine Phosphoprotein. *PNAS* 88, 9166–9170 (Oct. 1991).

Chung, J. et al. Rapamycin–FKBP specifically blocks growth–dependent activation of and signaling by the 70 kd S6 protein kinases. *Cell* 69, 1227–1235 (Jun. 26 1992).

Clark, M.R. et al. The B Cell Antigen Receptor Complex: Association of Ig–α and Ig–β With Distinct Cytoplasmic Effectors, *Science* 258, 123–126 (Oct. 2 1992).

Clipstone, N.A. et al. Calcineurin: Molecular analysis of its interaction with drug–immunophilin complexes and its role in the regulation of NF–AT. *J. Cell. Biochem. Suppl.* 0 (18B) 274, Abstract #I140 (1994).

Crabtree, G. R. IL–2 receptor in the pathogenesis of human lymphoma. Abstract of NIH Grant 5R01CA039612–03 (1987).

Crabtree, G. R. Pathways of T lymphocyte activation. Abstract of NIH Grant 2R01CA039612–07 (1991).

DiLella, A.G. et al. Chromosomal Band Assignments of the Genes Encoding Human FKBP12 and FKBP13. *Biochem. Biophys. Res. Commun.* 189, 819–823 (Dec. 15 1992).

Donald, D.K. et al. C10 N–Acyl Modified FK–506: A Possible Hybrid Analogue of the Transition State of Petidyl–Prolyl Cis–Trans Isomerization. *Tetrahedron Letters* 31, 1375–1378 (1991).

Durand, D.B et al. Characterization of Antigen Receptor Response Elements within the Interleukin–2 Enhancer. *Mol. Cell. Biol.* 8, 1715–1724 (Apr. 1988).

Eberle, M.K. and Nuninger, F. Synthesis of the Main Metabolite (OL–17) of Cyclosporin A. *J. Org. Chem.* 57, 2689–2691 (1992).

Edaiji, R. et al. High–Level Expression of Recombinant Human FK–Binding Protein from a Fusion Precursor. *J. Prot. Chem.* 11, 213–223 (1992).

Eiseman, E. and Bolen, J.B. Signal Transduction by the Cytoplasmic Domains of FcεRI–y and TCROJ–y in Rat Basophilic Leukemia Cells. *J. Biol. Chem.* 267, 21027–21032 (Oct. 15 1992).

Emmel, E.A. et al. Cyclosporin A Specifically Inhibits Function of Nuclear Proteins Involved in T–Cell Activation. *Science* 246, 1617–1620 (Dec. 22 1989).

Engel, I. et al. High–Efficiency Expression and Solubization of Functional T–Cell antigen Receptor Heterodimers. *Science* 256, 1318–1321 (May 29 1992).

Evans, D.A. et al. Mechanistic Study of the rhodium(I)– and Iridium(I)– Catalyzed Hydroboration Reactions: Scope and Synthetic Applications. *J. Am. Chem. Soc.* 114, 6671–6679 (1992).

Evans et al. Mechanistic study of the rhodium(I)–catalyzed hydroboration reaction. J. Am. Chem. Soc. 114, 6679–6685 (1992).

Fields, S. & Song, O–k., A Novel Genetic System to Detect Protein–Protein Interactions. *Nature* 340, 245–246 (Jul. 20 1989).

Fischer, G. et al. Mip protein of *Legionella pneumophila* exhibits peptidyl–prolyl–cis/trans isomerase (Pplase) activity. *Mol. Microbiol.* 6, 1375–1383 (1992).

Fisher, M.J. et al. On the Remarkable Propensity for Carbon–Carbon Bond Cleavage Reactions in the C8–C10 Region of FK–506. *J. Org. Chem.* 56, 2900–2907 (1991).

Flanagan, W.M. et al. Nuclear Association of a T–Cell Transcription Factor Blocked by a Tyrosine Factor Blocked by FK–506 and Cyclosporin A. *Nature* 352, 803–807 (Aug. 29 1991).

Flanagan, W.M. et al. Intracellular signal transmission: a novel role for the prolyl isomerases. *J. Cell. Biochem. Suppl.* 0 (16 Part A) 61, Abstract #B005 (1992).

Flanagan, W.M. et al. Nuclear association of a transcription factor essential for T cell activation by cyclosporin A and FK506. *J. Cell. Biochem. Suppl.* 0 (16 Part B), 237, Abstract #H514 (1992).

Francavilla, A. et al. Inhibition of Liver, Kidney, and Intestine Regeneration by Rapamycin. *Transplantation* 53, 496–498 (1992).

Fretz, H. et al. Rapamycin and FK506 Binding Proteins (Immunophilins). *J. Am. Chem. Soc.* 113, 1409–1411 (1991).

Friedman, J. & Weissman, I. Two Cytoplasmic Candidates for Immunophilin Action are Revealed by Affinity for a New Cyclophilin: One in the Presence and One in the Presence and One in the Absence of CsA. *Cell* 66, 799–806 (Aug. 23 1991).

Fuh, G. et al. Rational design of potent antagonists to the human growth hormone receptor *Science* 256, 1677–1680 (Jun. 19 1992).

Galat, A. et al. A Rapamycin–Selective 25 kDa Immunophilin. *Biochemistry* 31, 2427–2434 (1992).

Ghosh, A.K. et al. N,N'–Disuccinimidyl Carbonate: A Useful Reagent for Alkoxycarbonylation of Amines. *Tetrahedron Letters* 33, 2781–2784 (1992).

Gottschalk, W.K. et al. The Carboxy Terminal 100 Amino Acid Portion of the Insulin Receptor is Important for Insulin Signaling to Pyruvate Dehydrogenase. *Biochem. Biophys. Res Comm.* 189, 906–911 (Dec. 15 1992).

Haendler, B. et al. Complementary DNA for human T–cell cyclophilin. *EMBO J.* 6, 947–950 (1987).

Haendler, B. et al. Yeast cyclophilin: isolation and characterization of the protein, cDNA and gene. *Gene* 83, 39–46 (1989).

Harding, M.W. et al. A Receptor for the Immunosuppressant FK506 is a cis–trans Peptidyl–Prolyl Isomerase. *Nature* 341, 758–760 (1989).

Herbst, R. et al. Substrate Phosphorylation Specificity of the Human c–kit Receptor Tyrosine Kinase. *J. Biol. Chem.* 266, 19908–19916 (1991).

Howard, F.D. et al. The CD3ζCytoplasmic Domain Mediates CD2–Induced T Cell Activation. *J. Exp. Med.* 176, 139–145 (1992).

Hultsch, T. et al. Immunophilin Ligands Demonstrate Common Features of Signal Transduction Leading to Exocytosis or Transcription. *PNAS* 88, 6229–6233 (Jul. 1991).

Hultsch, T. et al. Inhibition of IgE Receptor–Mediated Exocytosis from Rat Basophilic Leukemia Cells by FK506 is Reversed by Rapamycin: Evidence for Common Signaling Pathways in Mast Cells and T Lymphocytes. *FASEB J*, 5, A1008 [3705] (1991).

Hung, D.T. & Schreiber, S.L. CDNA Cloning of A Human 25 kDa FK506 and Rapamycin Binding Protein. *Biochem. Biophys. Res. Comm.* 184, 733 (Apr. 30 1992).

Ikeda, Y. et al. Structural Basis for Peptidomimicry by a Natural Product. *J. Am. Chem. Soc.* 116, 4143–4144 (1994).

Irving, B.A. & Weiss, A. The Cytoplasmic Domain of the T Cell Receptor ζ Chain is Sufficient to Couple to Receptor–Associated Signal Transduction Pathways. *Cell* 64, 891–901 (Mar. 8 1991).

Ishizaka–Ikeda, E. et al. Signal transduction mediated by growth hormone receptor and its chimeric molecules with the granulocyte colony–stimulating factor receptor. PNAS 90, 123–127 (1993).

Itoh, N. & Nagata, S. A Novel Protein Domain Required for Apoptosis. *J. B. C.* 268, 10932–10937 (May 25 1993).

Itoh, N. et al. Effect of bcl–2 on Fas Antigen Mediated Cell Death. *J. Immunol.* 151, 621–627 (1993).

Jin, Y.–J. et al. Molecular cloning of a membrane–associated human FK506– and rapamycin–binding protein, FKBP–13. *PNAS* 88, 6677–6681 (Aug. 1991).

Kao, P.N. et al. Nuclear target of cyclosporin A and FK506 action is specifically bound by a heterodimeric protein comprising molecular weights 90K and 45K. *J. Cell. Biochem. Suppl.* 0 (16 Part B), 239, Abstract #H523 (1992).

Kaye, R.E. et al. Effects of Cyclosporin A and FK506 on Fce Receptor type I–Initiated Increases in Cytokine mRNA in Mouse Bone Marrow–Derived Progenito Mast Cells: Resistance to FK506 is Associated with a Deficiency in FKBP12. *PNAS* 89, 8542–8546 ( Sep. 1992).

Ke, H. et al. Crystal Structures of Cyclophilin A Complexed with Cyclosporin A and N–methyl–4–[(E)–2–Butenyl]–4, 4–Dimthyltheonine Cyclosporin A. *Structure* 2, 33–44 (Jan. 15 1994).

Kinet, J.–P. Antibody–Cell Interactions: Fc Receptors. *Cell* 57, 351–354 (May 5 1989).

Krishnamurthy, S. Lithium Tris[(3–ethyl–3–pentyl)oxy]aluminum Hydride. A New Remarkable Chemoselective Reagent for the Reduction of Aldehydes in the Presence of Ketones. *J. Org. Chem.* 46, 4628–4629 (1981).

Kruskal, B.A. et al. Phagocytic Chimeric Receptors Require Both Transmembrane and Cytoplasmic Domains from the Mannos Receptor. *J. Exp. Med.* 176, 1673–1680 (1992).

Lammers et al. Differential Signaling Potential in Insulin– and IGF–1–receptor Cytoplasmic Domains. *EMBO J.* 8, 1369–1375 (1989).

Lane et al. Complete Amino Acid Sequence of the FK506 and Rapamycin Binding Protein, FKBP, Isolted from Calf Thymus. *J. Prot. Chem.* 10, 151–160 (1991).

Lanier et al. Co–association of CD3c, with a Receptor (CD16) for IgG Fc on Human Natural Killer Cells. *Nature* 342, 803–805 (1989).

Larson & Nuss. Cyclophilin–dependent stimulation of transcriptionby cyclosporin A. *PNAS* 90, 148 (1993).

Lee, J. et al. HER2 Cytoplasmic Domain Generates Normal Mitogenic and Transforming Signals in a Chimeric Receptor. *EMBO J.* 8, 167–173 (1989).

Lee, A. W.–m. and Neinhuis, A.W. Functional Dissection of Structural Domains in the Receptor for Colony Stimulating Factor–1. *J. Biol. Chem.* 267, 16472–16483 (1992).

Lehtola et al. Receptor Downregulation and DNA Synthesis are Modulated by EGF and TPA in Cells Expressing an EGF/neu Chimera. *Growth Factors* 1, 323–334 (1989).

Lehtola et al. A chimeric EGFR/neu receptor in functional analysis of theneu oncoprotein.*Acta Oncologia* 31, 147–150 (1992).

Lehvaslaiho et al. A Chimeric EGF–R–neu Proto–Oncogene Allows EGF to Regulate neu Tyrosine Kinase and Cell Transformation. *EMBO J.* 8, 159–166 (1989).

Lehvaslaiho, H. et al. Regulation by EGF is maintained in an overexpressed chimeric EDG/neu receptor tyrosine kinase. *J. Cell. Biochem.* 42, 123–133 (1990).

Lefourneur, F. et al. T–cell and basophil activation through the cytoplasmic tail of T–cell–receptor zeta family proteins. PNAS 88, 8905–8909 (1991).

Lefourneur & Klausner. Activation of T Cells by a Tyrosine Kinase Activation Domain in the Cytoplasmic Tail of CD3 ε. *Science* 255, 79–82 (1992).

Lev et al. Receptor functions and ligand–dependent transforming potential of a chimeric kit profo–oncogene. *Mol. Cell. Biol.* 10, 6064–6068 (1990).

Lev et al. A Specific Combination of Substrates is Involved in Signal Transduction by the kit–Encoded Receptor. *EMBO J.* 10, 647–654 (1991).

Liu et al. Cloning, expression, and purification of human cyclophilin in *Escherichia coli* and assessment of the catalytic role of cysteines by site–directed mutagenesis. *PNAS* 87, 2304 (1990).

Liu et al. Calcineurin is a Common Target of Cyclophilin–Cyclosporin A and FKBP–FK506 Complexes. *Cell* 66, 807 (1991).

Liu et al. Inhibition of T Cell Signaling by Immunophilin–Ligand Complexes Correlates With Loss of Calcineurin Phosphatase Activity, *Biochemistry* 31, 3896–3901 (1992).

Liu, FK506 and cyclosporin, molecular probes for studying intracellular signal transduction. *Immunology Today* 14, 290 (1993).

Maki, N. et al. Complementary DNA encoding the human T–Cell FK506–binding protein, a peptidylprolyl cis–trans isomerase distinct from cyclophilin. *PNAS* 87, 5440–5443 (Jul. 1990).

Mares et al. A Chimera between Platelet–Derived Growth Factor B–receptor and Fibroblast Growth Factor Receptor–1 Stimulates Pancreatic β–DNA Synthesis in the Presence of PDGF–BB. *Growth Factors* 6, 93–101 (1992).

Margolis et al. All Autophosphorylation Sites of Epidermal Growth Factor (EGF) Receptor and HER2/neu are Located in their Carboxyl–Terminals Tails. *J. Biol. Chem.* 264, 10667–10671 (1989).

Mattila et al. The Actions of Cyclosporin A and FK506 Suggest A Novel Step in the Activation of T Lymphocytes. *EMBO J.* 9, 4425–4433 (1990).

Meyer et al. Synthetic Investigations of Rapamycin. 1. Synthesis of a C10–C21 Fragment. *J. Org. Chem.* 57, 5058–5060 (1992).

Michnick et al. Solution Structure of FKBP, a Rotamese Enzyme and Receptor for FK506 and Rapamycin, *Science* 252, 836–839 (1991).

Moe et al. Transmembrane Signaling by a Chimera of the *Escherichia coli* Aspartate Receptor and the Human Insulin Receptor. *PNAS* 86, 5683–5687 (1989).

Nakatsuka et al. Total Syntheses of FK506 and an FKBP Probe Reagent, (C8, C9–13C2)–FK506. *J. Am. Chem. Soc.* 112, 5583 (1990).

Nussbaumer et al. C9–Imino and C10–Amino Derivatives of Ascomycin (21–Ethyl–FK506). *Tetrahedron Letters* 33, 3845–3846 (1992).

Orloff et al. Family of Disulphide–Linked Dimers Containing the ζ and η Chains of the T–Cell Receptor and the γChain of the Fc Receptors. *Nature* 347, 189–191 (1990).

Palmiter et al. Transgenic Mice. *Cell* 41, 343–345 (1985).

Patchett et al. Analogs of Cyclosporin A Modified at the D–ALA$^8$ Position. *J. Antibiotics* 45, 94–102 (1992).

Peles et al. Regulated Coupling of the Neu Receptor to Phosphatidylinositol. *J. Biol. Chem.* 267, 12266–12274 (1992).

Price et al. Human cyclophilin B: A second cyclophilin gene encodes a peptidyl–prolyl isomerase with a signal sequence, *PNAS* 88, 1903 (1991).

Ptashne et al. Activators and Targets. *Nature* 346, 329–331 (1990).

Ragan et al. Studies of the Immunosuppressive Agent FK506: Synthesis of an Advanced Intermediate. *J. Org. Chem.* 54, 4267–4268 (1989).

Reins et al. Anti–epidermal growth factor receptor monoclonal antibodies affecting signal transduction. *J. Cell. Biol.* 51, 236–248 (1993).

Riedel et al. Cytoplasmic Domains Determine Signal Specificity, Cellular Routing Characteristics and Influence Ligand Binding of Epidermal Growth Factor and Insulin Receptors. *EMBO J.* 8, 2943–2954 (1989).

Romeo et al. Cellular immunity to HIV activated by CD4 fused to T cell or Fc receptor polypeptides. *Cell* 64, 1037–1046 (1991).

Romo et al. Synthetic Investigations of Rapamycin. 2. Synthesis of a C22–C42 Fragment. *J. Org. Chem.* 57, 5060–5063 (1992).

Romo et al. Total Synthesis of Rapamycin Using an Evans–Tischenko Fragment Coupling. *J. Am. Chem. Soc.* 115, 7906–7907 (1993).

Rosen et al. Inhibition of FKBP Rotamase Activity by Immunosuppressant FK506: A Twisted Amide Surrogate. *Science* 248, 863 (1990).

Rosen et al. Proton and Nitrogen Sequential Assignments and Secondary Structure Determination of the Human FK506 and Rapamycin Binding Protein. *Biochemistry* 30, 4774–4789 (1991).

Rosen et al. Study of Receptor–Ligand Interactions Through Receptor Labeling and Isotope–Edited NMR. *J. Org. Chem.* 56, 6262 (1991).

Rosen et al. Natural Products as Probes of Cellular Function: Studies of Immunophilins. *Angew. Chemie. Int. Ed. Eng.* 31, 384–400 (1992).

Rosen et al. Activation of an Inactive Immunophilin by Mutagenesis. *J. Am. Chem. Soc.* 115, 821–822 (1993).

Rosen, M.K. The molecular basis of receptor–ligand–receptor interactions: Studies of the immunophilin FKBP12. Abstract of Doctoral Thesis (1993).

Roussel et al. Antibody–induced Mitogenicity Mediated by a Chimeric CD2–c–fms Receptor. *Mol. Cell. Biol.* 10, 2407–2412 (1990).

Rudert et al. Apoptosis in L929 cells expressing a CD40/Fas chimeric receptor. Dissociation of stimulatory from inhibory death signaling functions. *Biochem. Biophys. Res. Comm.* 204, 1102 (1994).

Sampson & Gotschlich. Neisseria meningitidis encodes an FK506–inhibitable rotamase. *PNAS* 89, 1164 (1992).

Schreiber, S. L. Synthesis of materials with physiological properties. Abstract of NIH Grant R37GM38627, (1987).

Schreiber et al. Is There a Scaffolding Domain within the Structure of the Immunosuppressive Agent Cyclosporin A (CsA)? Studies of the Cyclophilin Binding Domain of CsA. *Tetrahedron Lett.* 29, 6577 (1988).

Schreiber, S. L. Analysis of cyclosporin–receptor interaction: Synthesis of semi–peptide and non–peptide analogs of cyclosporin A. Abstract of NIH Grant P01GM406600001 (1989).

Schreiber et al. Studies Relating to the Synthesis of the Immunosuppressive Agent FK506: Application of the Two Directional Chain Synthesis Strategy to the Pyranose Moiety. *J. Org. Chem.* 54, p. 9, 15, 17 (1989).

Schreiber et al. Protein Overproduction for Organic Chemists. *Tetrahedron* 47, 2543–2562 (1991).

Schreiber et al. Immunophilin–Ligand Complexes as Probes of Intracellular Signaling Pathways. *Transplantation Proceedings* 23, 2839 (1991).

Schreiber, S. L. Chemistry and Biology of the Immunophilins and their Immunosuppressive Ligands. *Science* 251, 283 (1991).

Schreiber, S. L. Synthesis of materials with physiological properties. Abstract of NIH Grant R37GM38627, (1992).

Schreiber et al. Molecular Recognition of Immunophilins and Immunophilin–Ligand Complexes. *Tetrahedron* 48, 2545–2558 (1992).

Schreiber et al. The Mechanism of Action of Cyclosporin A and FK506. *Immunology Today* 13, 136–142 (1992).

Schreiber, S. L. Immunophilin–Sensitive Phosphatase Action in Cell Signaling Pathways. *Cell* 70, 365–369–8 (1992).

Schultz et al. Atomic Structure of the Immunophilin FKBP13–FK506 Complex: Insights into the Composite Binding Surface for Calcineurin. *J. Am. Chem. Soc.* 116, 3129–3130 (1994).

Seedorf et al. Analysis of platelet–derived growth factor receptor domain function using a novel chimeric receptor approach. *J. Biol. Chem.* 266, 12424–12431 (1991).

Seedorf et al. Differential effects of carboxyl–terminal sequence deletions on platelet–derived growth factor receptor signaling activities and interactions with cellular substrates. *Mol. Cell. Biol.* 12, 4347–4356 (1992).

Selvakumaran et al. Myeloblastic leukemia cells conditionally blocked Myo–estrogen receptor chimeric transgenes for terminal differentiation coupled to growth arrest and apoptosis. *Blood* 81, 2257 (1993).

Serafini et al. Selection and characterization of mutants in a signal transduction/transmission pathway. *J. Cell. Biochem. Suppl.* 0 (6 Part A), 89, Abstract #B234 (1992).

Shaw et al. Identification of a Putative Regulator of Early T Cell Activation Genes. *Science* 241, 202 (1988).

Sistonen et al. Activation of the neu Tyrosine Kinase Induces the fos/jun Transcription Factor Complex, the Glucose Transporter, and Ornithine Decarbocylase. *J. Cell Biol.* 109, 1911–1919 (1989).

Smith et al. FKBP54, a Novel FK506 Binding Protein in Avian Progesterone Receptor Complexes and HeLa Extracts. *J. Biol. Chem.* 268, 24270–24273 (1993).

Somers et al. Synthesis and Analysis of 506BD, a High Affinity Ligand to the Immunophilin, FKBP. *J. Am. Chem. Soc.* 113, 8045–8056 (1991).

Standaert et al. Molecular cloning and overexpression of the human FK506–binding protein FKBP. *Nature* 346, 671 (1990).

Standaert, R.F. Biochemical and structural studies of the FK506– and rapamycin–binding proteins (FKBPs). Abstract of Doctoral Thesis (1992).

Tai et al. Association of a 59–Kilodalton immunophilin with the Glucocorticoid Receptor Complex. *Science* 256, 1315–1318 (1992).

Tai et al. P59 (FK506 Binding Protein 59) Interaction with Heat Shock Proteins is Highly Conserved and May Involve Proteins Other Than Steroid Receptors. *Biochemistry* 32, 8842–8847 (1993).

Tanide et al. Yeast Cyclophilin–related gene encodes a nonessential second peptidyl–prolyl cis–trans isomerase with the secretory pathway. *Transplantation Proceedings* 23, 2856 (1991).

Traber et al. Cyclosporins—New Analogues by Precursor Directed Biosynthesis. *J. Antibiotics* 42, 591–597 (1989).

Ullman et al. Site of action of cyclosporin and FK506 in the pathways of communication between the T–lymphocyte antigen receptor and the early activation genes. *Transplant. Proceed.* 23, 2845 (1991).

Van Duyne et al. Atomic Structure of the Rapamycin human immunophilin FKBP–12 complex. *J. Am. Chem. Soc.* 113, 7433 (1991).

Van Duyne et al. Atomic Structure of FKBP–FK506, an Immunophilin–Immunosuppressant Complex. *Science* 252, 839–842 (1991).

Van Duyne et al. Atomic Structures of the Human Immunophilin FKBP12 Complexes with FK506– and Rapamycin. *J. Mol. Biol.* 229, 105–124 (1993).

VanRheenen et al. An Improved Catalytic OsO4 Oxidation of the Olefins to Cis–1,2 Glycols Using Tertiary Amine Oxides as the Oxidant. *Tetrahedron Letters* 23, 1973–1976 (1976).

Venkitaraman et al. Interleukin 7 receptor functions by recruiting the tyrosine kinase p59$^{fyn}$ through a segment of its cytoplasmic tail. *PNAS* 89, 12083–12087 (1992).

Verweij et al. Cell Type Specificity and Activation Requirements for NFAT-1 (Nuclear Factor of Activated T–Cells) Transcriptional Activity Determined by a New Method Using Transgenic Mice to Assay Transcriptional Activity of an Individual Nuclear Factor. *J. Biol. Chem.* 265, 15788 (1990).

Walsh et al. Cyclosporin A, the Cyclophilin Class of Peptidylprolyl Isomerases, and Blockade of T Cell Signal Transduction, *J. Biol. Chem*, 267, 13115 (1992).

Wandless et al. FK506 and Rapamycin Binding of FKBP: Common Elements Involved in Immunophilin–Ligand Complexation. *J. Am. Chem. Soc.* 113, 2339–2341 (1991).

Wandless, T.J. Turning genes on and off using FKBP and FK506. Doctoral Thesis (1993).

Watanabe–Fukunga et al. Lymphoproliferation Disorder in Mice Explained by Defects in Fas Antigen that Mediates Apoptosis. *Nature* 356, 314–317 (1992).

Weissman et al. Molecular Cloning and Chromosomal Localization of the Human T–Cell Receptor ζ Chain: Distinction from the Molecular CD3 Complex. *PNAS* 85, 9709–9713 (1988).

Wennstrom et al. The platelet–derived growth factor beta–receptor kinase insert confers specific signaling properties to a chimeric fibroblast growth factor receptor. *J. Biol. Chem.* 267, 13749–13756 (1992).

Wittbrodt et al. The Xmrk Receptor Tyrosine Kinase is Activated in Xiphophorous Malignant Melanoma. *EMBO J.* 11, 4239–4246 (1992).

Yang et al. A Composite FKBP12–FK506 Surfact That Contacts Calcineurin. *J. Am. Chem. Soc.* 115, 819–820 (1993).

Yarden et al. Growth factor receptor tyrosine kinases. *Ann. Rev. Biochem.* 57, 443–478 (1988).

Zelle et al. Systematic Degradation of Zincophorin: A Stereoselective Synthesis of the C17–C25 Fragment. *J. Org. Chem.* 51, 5032–5036 (1986).

Zhang et al. The insulin receptor–related receptor. *J. Biol. Chem.* 267, 18320–18328 (1992).

Zydowsky et al. Active site mutants of human cyclophilin A separate peptidyl–prolyl isomerase activity from cyclosporin A binding and calcineurin inhibition. *Prot. Sci.* 1, 1092 (1992).

Zydowsky et al. Overexpressoin, purification, and characterization of yeast cyclophilins A and B. *Protein Sci.* 1, 961 (1992).

* cited by examiner

Construction of intracellular signalling chimera:
1. PCR myristoylated CD3ζ
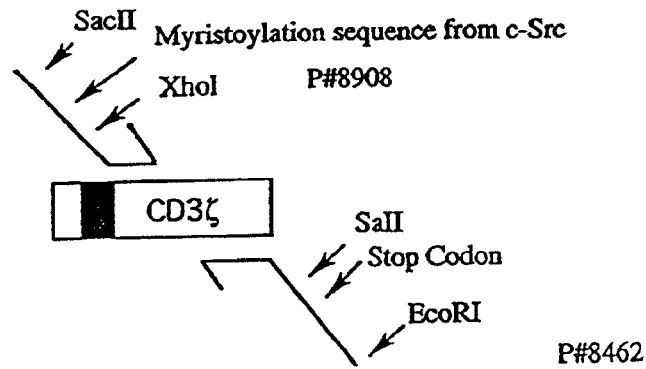
2. Cut and clone PCR fragment
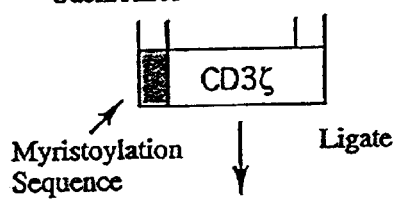
*The MZE series contains a 9aa HA epitope at the 3' end.
pBJ5 (XhoI)(SalI)
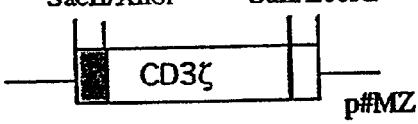 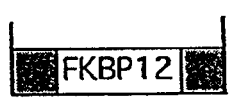
3. SEQUENCE insert
From plasmid #FK12/KS
4. Cut at XhoI or SalI and add FKBP domains
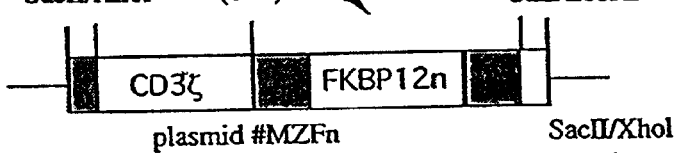 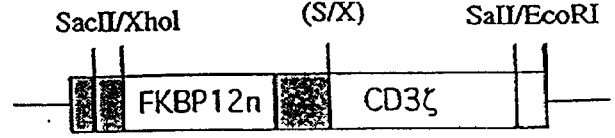
Figure 2

Construction of extracellular signaling chimera:
1. PCR murine signal peptide
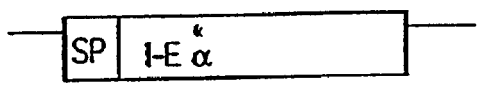
P#6048
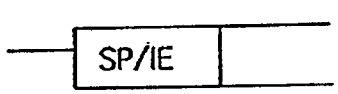
P#6049
2. PCR CD3 trans-membrane and cytoplasmic domains
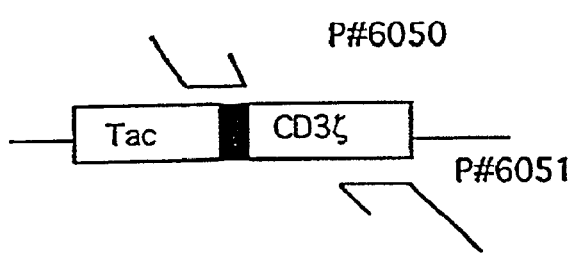
Tζζ
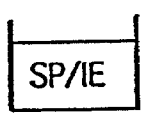 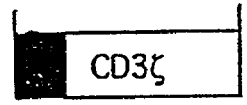
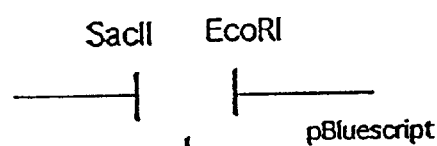
pBluescript
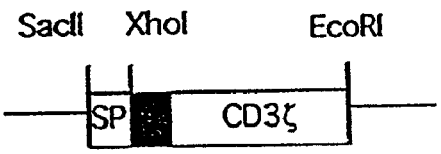
plasmid #SPZ/KS
SEQUENCE insert*
Cut XhoI
Figure 3A

CYCC

6568: 5'-CGACACTCGAGGTGACGGACAAGGTC-3'
         Xhol    homology

6569: 5'-CGACAGTCGACCCAATCAGGGACCTC-3'
         Sall    homology

EPITOPE

7850: 5'-TCGAGTATCCGTACGACGTACCAGACTACGCAG-3'
         Xhol    BsiWI
              Y  P  Y  D  V  P  D  Y  A 7851: 5'-TCGACTGCGTAGTCTGGTACGTCGTACGGATAC-3'
         Sall

EPITOPE: 5SEP, 3XEP

8922: 5'-TCGACTATCCGTACGACGTACCAGACTACGCAC-3'
         Sall

8923: 5'-TCGAGTGCGTAGTCTGGTACGTCGTACGGATAG-3'
         Xhol

Myristoylation from c-src 5SMXZ

8908: 5'-CGACACCGCGGCCACCATGGGGAGTAGCAAGAGCAAGCCT
         Sacll
              KOZAK M  G  S  S  K  S  K  P AAGGACCCCAGCCAGCGCCTCGAGAGGAGTGCAGAGACTG-3'
                              Xhol    ζ-homology
         K  D  P  S  Q  R  L  E  R  S  A  E  T

5XTZ

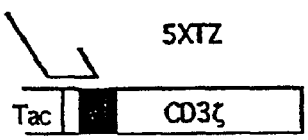

8912: 5'-CGACACTCGAGGAGCTCTGTGACGATG-3'
         Xhol            homology
              E  L  C  D  D

Figure 4B

```
Asp-Lys #4                    XhoI   ┌──── homology ────┐
                              ───    │    * *           │
8061:    5'-CGACACTCGAGCTCTGCTACTTGCTAAAGGGAATCCTCTTC-3'
              E  L  C  Y  L  L  K  G  I  L  F

*GAT to AAG
                                            ┌── homology ──┐
#4 Extension      XhoI                      │              │
                  ───
8907:    5'-CGACACTCGAGCTGCTGGATCCGAAGCTCTGCTACTTGCTAAAG-3'
              E  L  L  D  P  K  L  C  Y  L  K TAC-Tm #3         XhoI   ┌── homology ──┐
                  ───    │              │
7220:    5'-CGACACTCGAGACAACAGAGTACCAGGTAGC-3'
              E  T  T  E  Y  Q  V
```

Figure 4C (partial — immunophilin section)

```
                 ┌──────────────┐
    ─────────────│ immunophilin │─────────────
                 └──────────────┘

FKBP12                XhoI   ┌── homology ──┐
                      ───
6052:    5'-CGACACTCGAGGGCGTGCAGGTGGAGAC-3'
              E  G  V  Q  V  E ┌── homology ──┐
                      SalI   │              │
                      ───
6053:    5'-CGACAGTCGACTTCCAGTTTTAGAAGC-3'
              V  E  L  K  L  L FKBP13                XhoI   ┌── homology ──┐
                      ───
8460:    5'-TCGACACTCGAGACGGGGGCCGAGGGC-3'
              E  T  G  A  E  G ┌── homology ──┐
                      SalI   │              │
                      ───
8461:    5'-CCGACAGTCGACCTCTATTTTGAGCAGC-3'
              V  E  I
```

Figure 4C

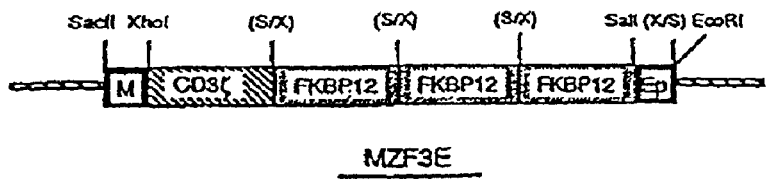
MZF3E
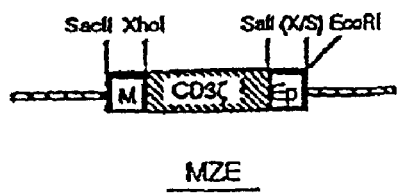
MZE
Cut XhoI/SalI; CIP; + FKBP12 X 3
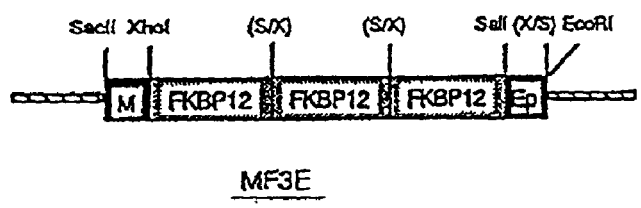
MF3E
+
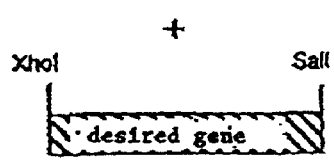
1. Cytoplasmic moiety of surface receptor
2. Tyrosine Kinase
3. Transcription Factor
4. Others
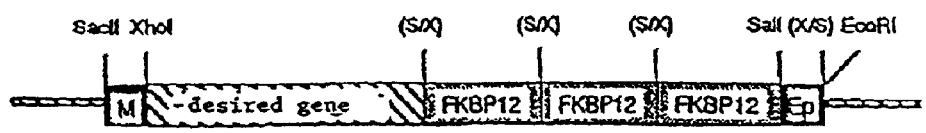
Figure 6B

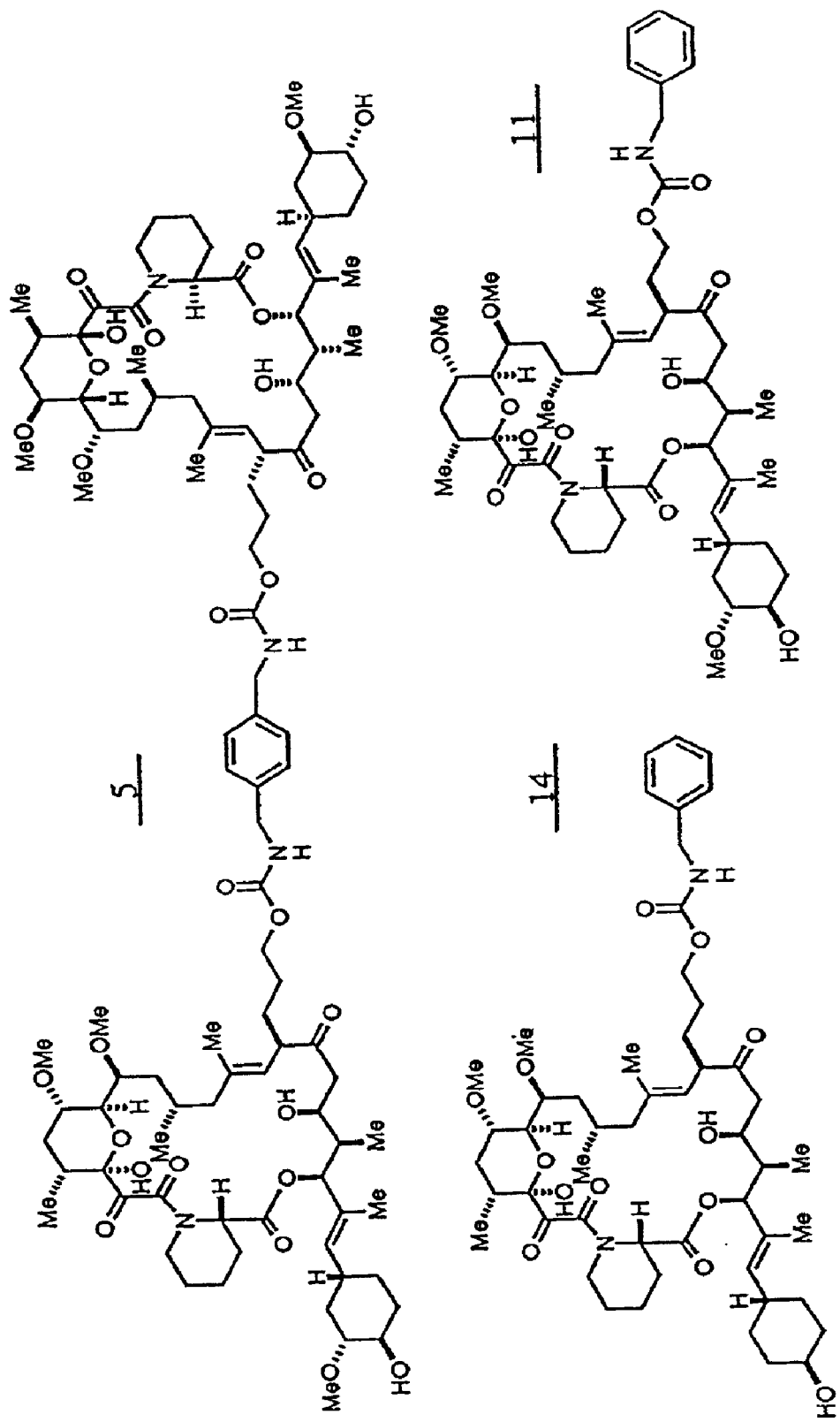
Figure 9A (#1)

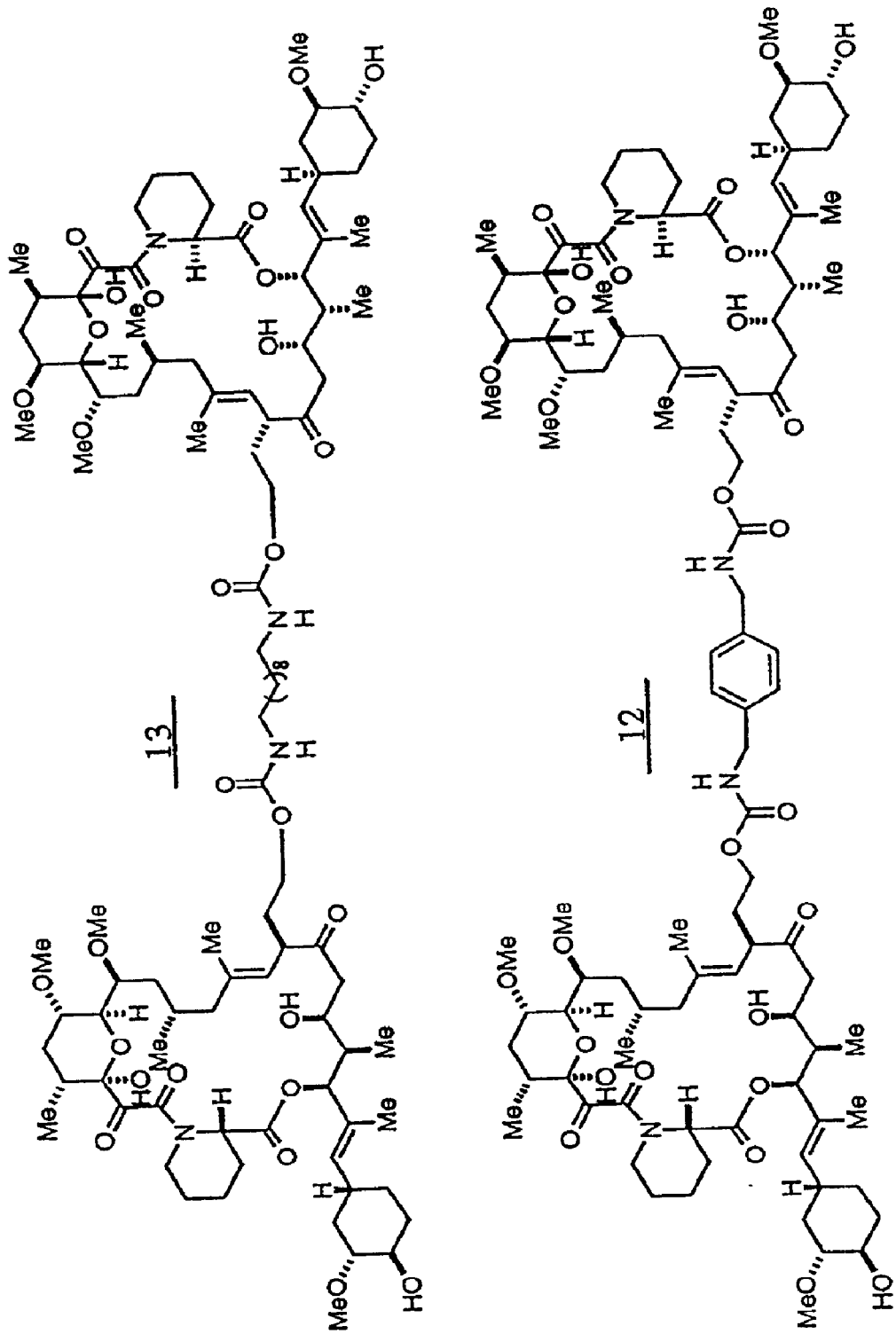
Figure 9A(#2)

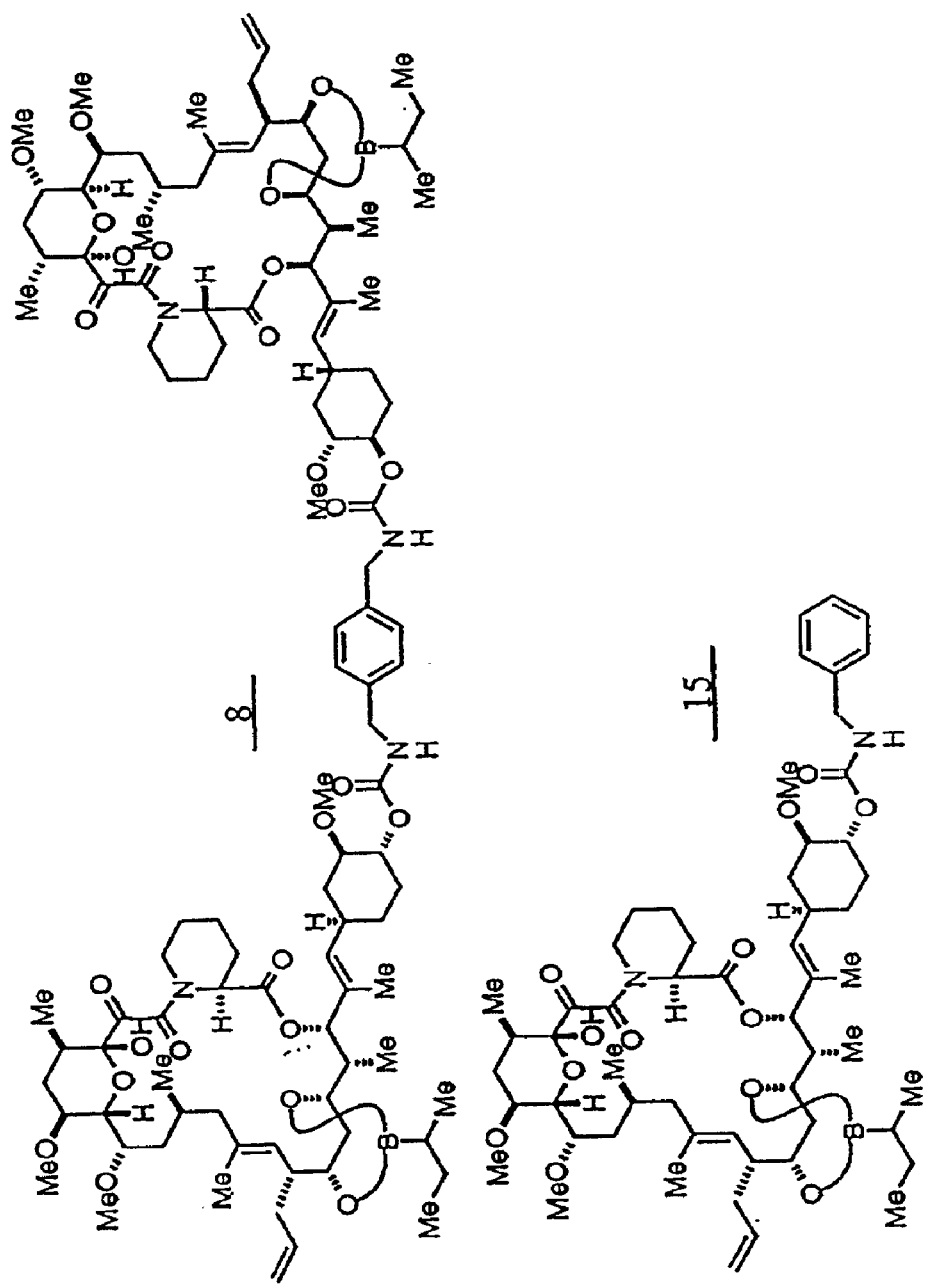
Figure 9B (#1)

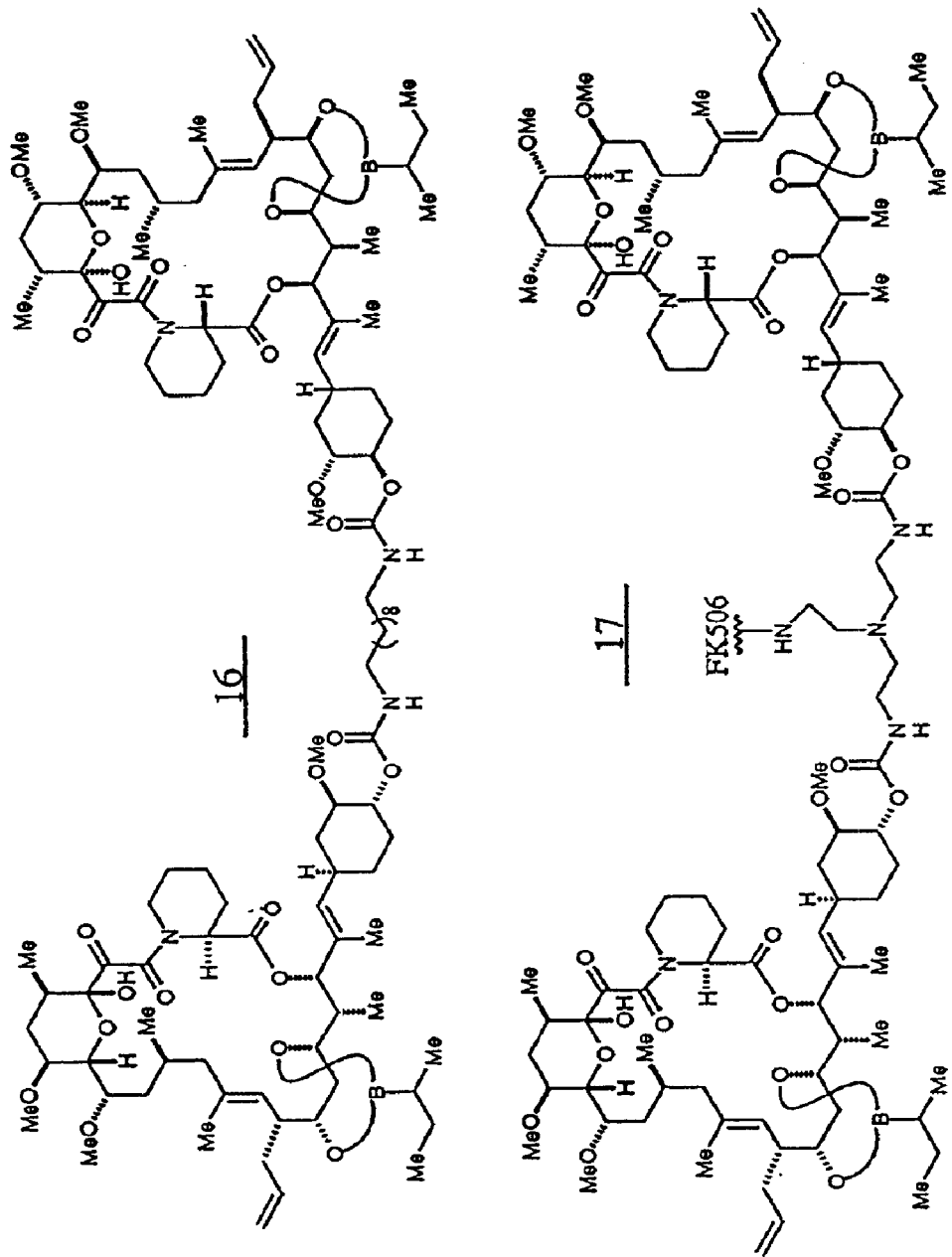
Figure 9B (#2)

Scheme 2: Synthesis of Dimers
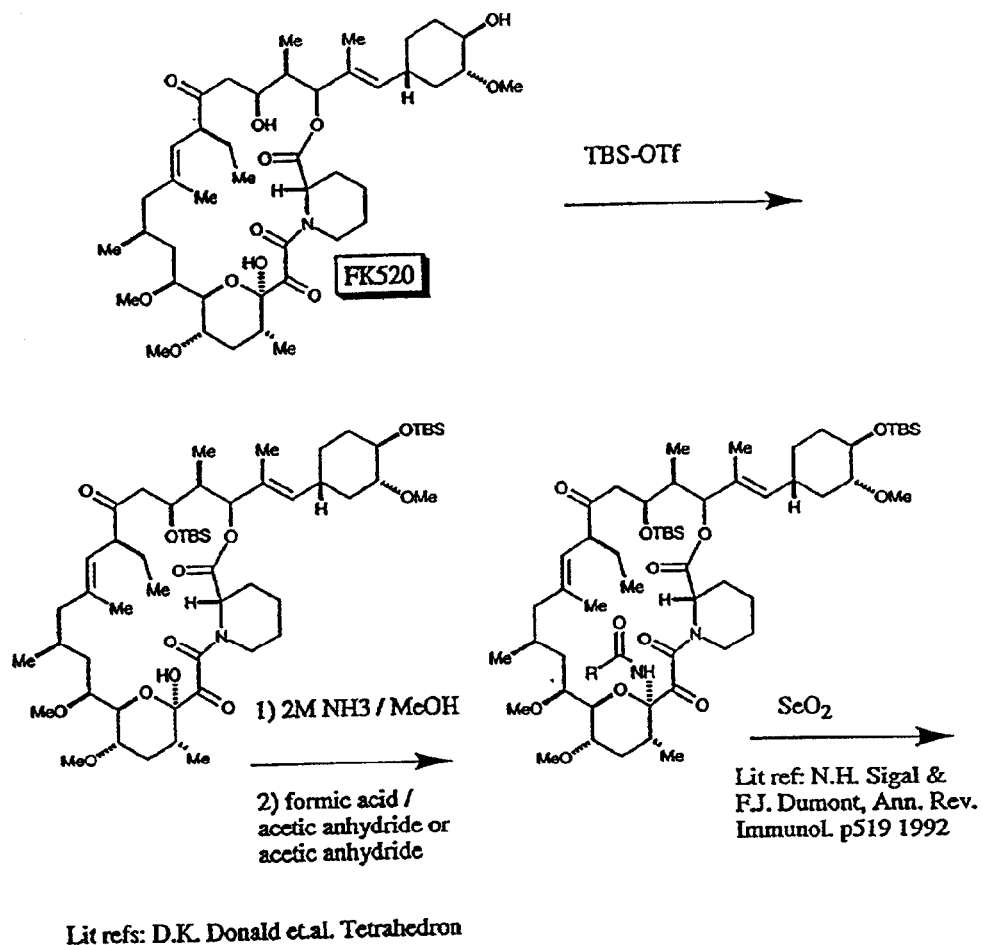
Lit refs: D.K. Donald et al. Tetrahedron Letters p1375, 1991, P.Kocovsky, Tetrahedron Letters p5521, 1992
Lit ref: N.H. Sigal & F.J. Dumont, Ann. Rev. Immunol. p519 1992
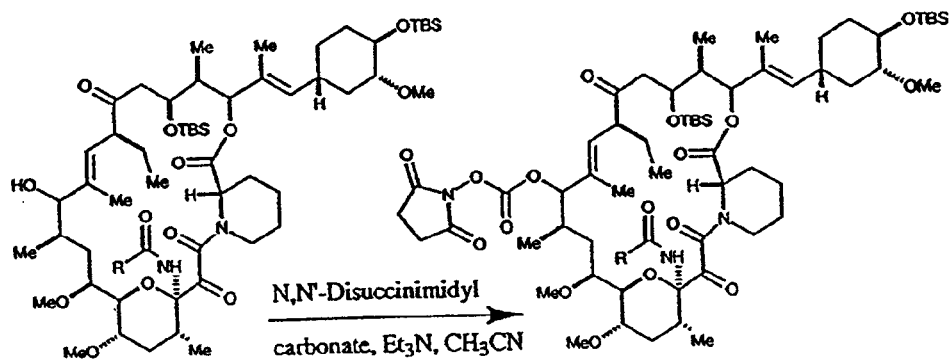
Figure 11A

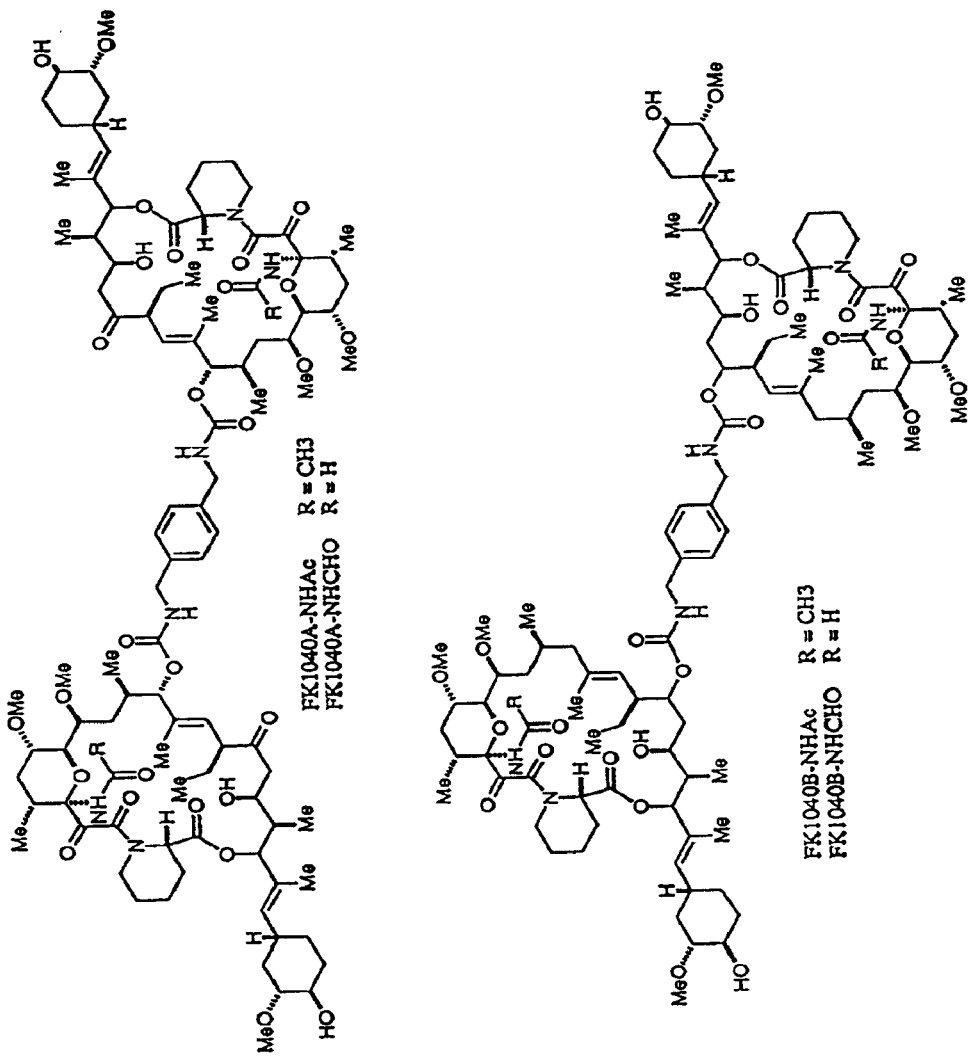
Figure 11B (#1)

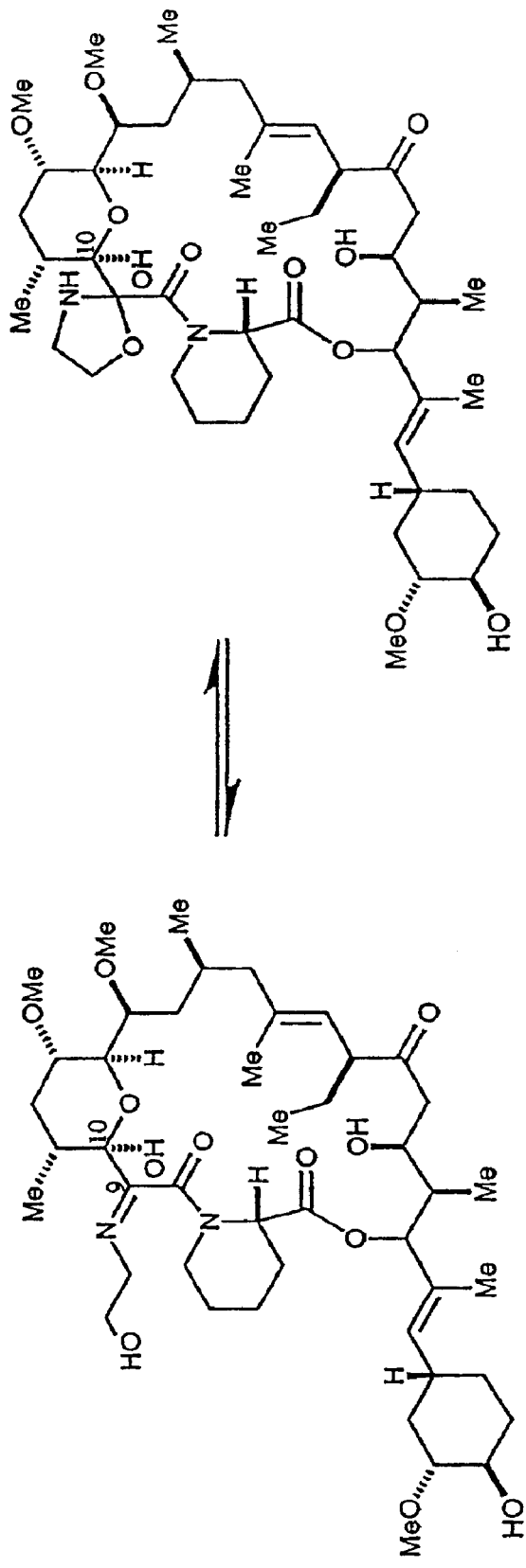
Figure 11B (#2)

Scheme 3    Heterodimerization

Note:

Bump #1 prevents binding to wt FKBP12 and to mutant #2

Bump #2 prevents binding to wt FKBP12 and to mutant #1

Scheme 3: Synthesis of heterodimers

In this example, a heterodimer of a cyclosporine analog and FK520A-NHCO-R were heterodimerized. However, the scheme can easily incorporate other FK506/520 derivatives to form hetero or homodimers

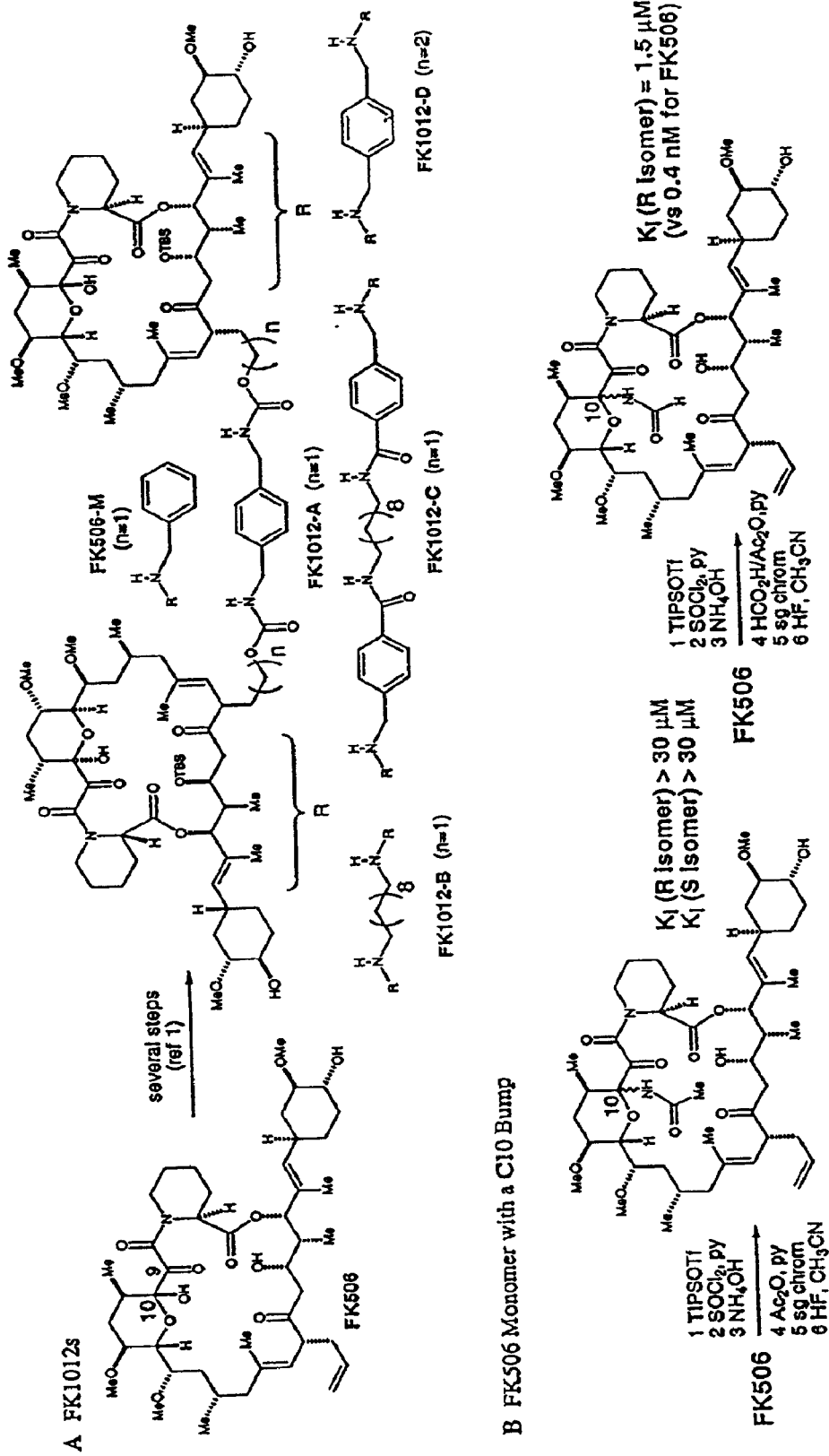
Figure 16 (#1)

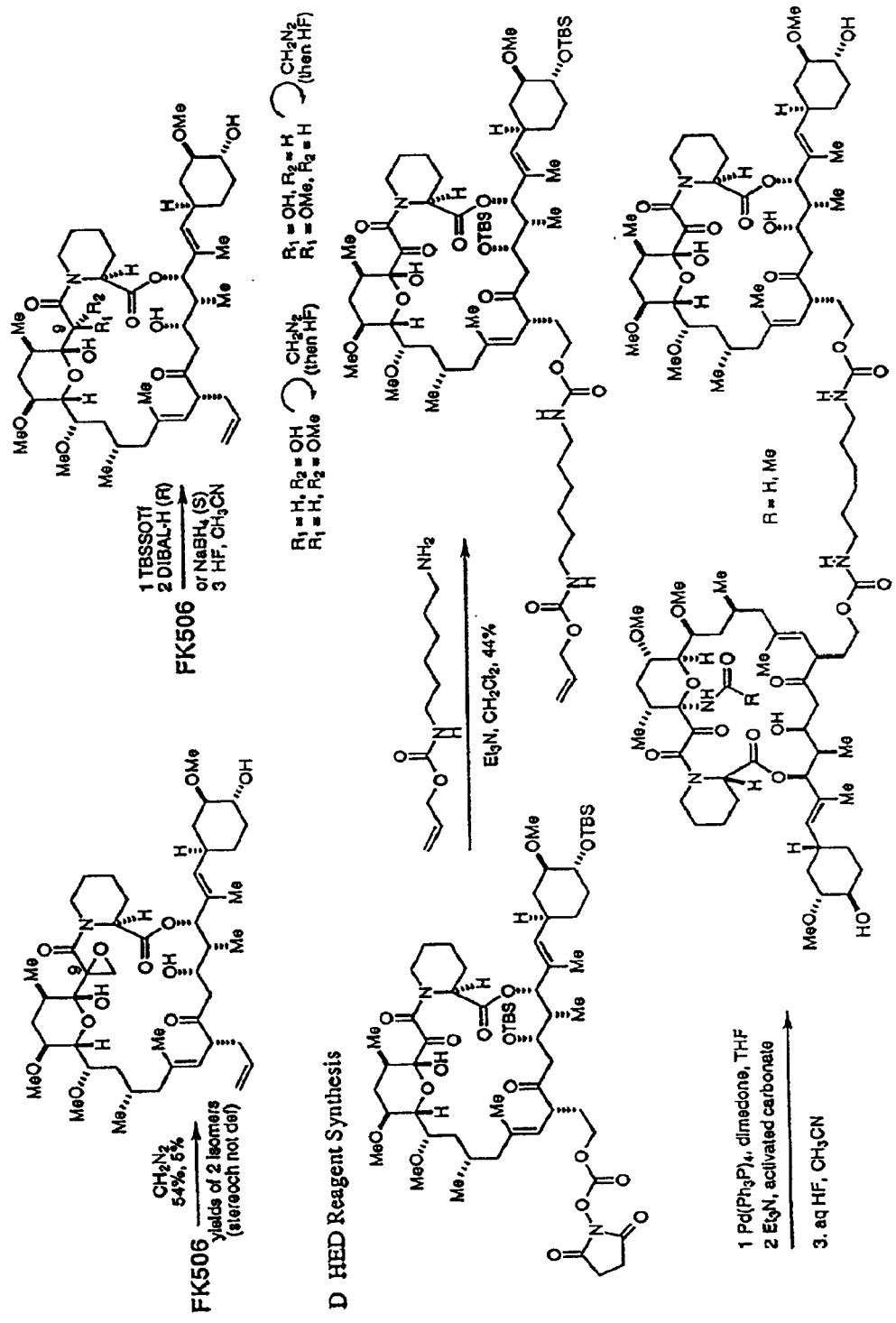
Figure 16 (#2)

A    cDNA construct

- N-terminus of Src (14 aa)
- cytoplasmic tail of ζ
- MZF3E
- 1, 2, or 3 FKBP12 Domains B    expressed protein Extracellular Space Cytoplasm

MZF3E (FKBP12)n
n = 1,2,3

REGULATED APOPTOSIS

This application is a continuation of U.S. Ser. No. 09/302,629, filed Apr. 30, 1999 (U.S. Pat. No. 6,316,418), which is a continuation of U.S. Ser. No. 09/087,811, filed May 29, 1998 (U.S. Pat. No. 6,054,436), which is a continuation of U.S. Ser. No. 08/292,597, filed Aug. 18, 1994 (U.S. Pat. No. 5,834,266), which is a continuation-in-part of U.S. Ser. No. 08/179,143 filed Jan. 7, 1994 (abandoned), which is a continuation-in-part of U.S. Ser. No. 08/093,499 filed Jul. 16, 1993 (abandoned); U.S. Ser. No. 09/302,629 is also a continuation-in-part of U.S. Ser. No. 08/196,043 filed Feb. 11, 1994 (abandoned), which is a continuation-in-part of U.S. Ser. No. 08/179,748 filed Jan. 7, 1994 (abandoned), which is a continuation-in-part of U.S. Ser. No. 08/092,977 filed Jul. 16, 1993 (abandoned), which is a continuation-in-part of U.S. Ser. No. 08/017,931 filed Feb. 12, 1993 (abandoned).

TECHNICAL FIELD

This invention concerns materials, methods and applications relating to the oligomerizing of chimeric proteins with a dimeric or multimeric, preferably non-peptidic, organic molecule. Aspects of the invention are exemplified by recombinant modifications of host cells and their use in gene therapy or other applications of inducible gene expression.

INTRODUCTION

Biological specificity usually results from highly specific interactions among proteins. This principle is exemplified by signal transduction, the process by which extracellular molecules influence intracellular events. Many pathways originate with the binding of extracellular ligands to cell surface receptors. In many cases receptor dimerization leads to transphosphorylation and the recruitment of proteins that continue the signaling cascade. The realization that membrane receptors could be activated by homodimerization resulted from the observation that receptors could be activated by antibodies that cross linked two receptors. Subsequently, many receptors were found to share those properties. The extracellular and transmembrane regions of many receptors are believed to function by bringing the cytoplasmic domains of the receptors in dose proximity by a ligand-dependent dimerization or oligomerization, while the cytoplasmic domains of the receptor convey specific signals to internal compartments of the cell.

Others have investigated ligand-receptor interactions in different systems. For example, Clark, et al., Science (1992) 258, 123 describe cytoplasmic effectors of the B-cell antigen receptor complex Durand, et al., Mol. Cell. Biol. (1988) 8, 1715, Verweij, et al., J. Biol. Chem. (1990) 265, 15788 and Shaw, et al., Science (1988) 241, 202 report that the NF-AT-directed transcription is rigorously under the control of the antigen receptor. Inhibition of NF-AT-directed transcription by cyclosporin A and FK506 is reported by Emmel, et al., Science (1989) 246, 1617 and Flanagan, et al., Nature (1991) 352, 803. Durand, et al., Mol. Cell. Biol. (1988) 8, 1715 and Mattila, et al., EMBO J. (1990) 9, 4425 describe the NF-AT binding sites. References describing the ζ chain include Orloff, et al., Nature (1990) 347, 189–191; Kinet, et al., Cell (1989) 57, 351–354; Weissman, et al., Proc. Natl. Acad. Sci. USA (1988) 85, 9709–9713 and Lanier, Nature (1989) 342, 803–805. A CD4 immunoadhesin is described by Byrn, et al. Nature (1990) 344, 667–670. A CD8-ζ-fused protein is described by Irving, et al., Cell (1992) 64, 891. See also, Letourner and Klausner, Science (1992) 255, 79.

Illustrative articles describing transcriptional factor association with promoter regions and the separate activation and DNA binding of transcription factors include: Keegan et al., Nature (1986) 231, 699; Fields and Song, ibid (1989) 340, 245; Jones, Cell (1990) 61, 9; Lewin, Cell (1990) 61, 1161; Ptashne and Gann, Nature (1990) 346, 329; Adams and Workman, Cell (1993) 72, 306.

Illustrative articles describing vesicle targeting and fusion include: Sollner et al. (1993) Nature 362, 318–324; and Bennett and Scheller (1993) Proc. Natl. Acad. Sci. USA 90, 2559–2563.

Illustrative articles describing regulated protein degradation include: Hochstrasser et al. (1990) Cell 61, 697; Scheffner, M. et al. (1993) Cell 75, 495; Rogers et al. (1986) Science 234, 361–368.

Illustrative publications providing additional information concerning synthetic techniques and modifications relevant to FK506 and related compounds include: GB 2 244 991 A; EP 0 455 427 A1; WO 91/17754; EP 0 465 426 A1, U.S. Pat. No. 5,023,263 and WO 92/00278.

Illustrative publications concerning the Fas antigen, p55 TNF receptor (hereinafter "TNF receptor") and/or apoptosis include: Itoh, et al. (1991) Cell 66, 233–243; Nagata, et al., European Patent Application Publication No. 510 691 (1992); Suda et al, Cell (1993), 75(6), 1169–78; Oehm, et al., J Biological Chem. (1992) 267(15), 10709–10715; and Wong and Goeddel, J Immunol (1994),152(4), 1751–5.

Illustrative discussion of methods and materials for gene therapy is found in Chapter 28 of Watson, Gilman, Witkowski and Zoller, RECOMBINANT DNA, 2d edition (WH Freeman & Co, 1992) and in references cited in the bibliography therein especially on pp 564–565.

However, as will be clear from this disclosure, none of the foregoing authors describe or suggest the present invention. Our invention, which is disclosed in detail hereinafter, involves a generally applicable method and materials for utilizing protein homodimerization, heterodimerization and oligomerization in living cells. (As used herein, the terms oligomer, oligomerize and oligomerization encompass dimers, trimers and higher order oligomers and their formation.) Chimeric responder proteins are intracellularly expressed as fusion proteins with a specific receptor domain. Treatment of the cells with a cell permeable multivalent ligand reagent which binds to the receptor domain leads to dimerization or oligomerization of the chimera. In analogy to other chimeric receptors (see e.g. Weiss, *Cell* (1993) 73, 209), the chimeric proteins are designed such that oligomerization triggers cell death, and in certain embodiments, optional other subsequent events, e.g. the propagation of an intracellular signal via subsequent protein-protein interactions and thereby the activation of a specific subset of transcription factors. The initiation of transcription can be detected using a reporter gene assay. Intracellular crosslinking of chimeric proteins by synthetic ligands has potential in basic investigation of a variety of cellular processes, in regulatably initiating cell death in engineered cells and in regulating the synthesis of proteins of therapeutic or agricultural importance. Furthermore, ligand mediated oligomerization now permits regulated gene therapy. In so doing, it provides a fresh approach to increasing the safety, expression level and overall efficacy obtained with gene therapy.

SUMMARY OF THE INVENTION

This invention provides materials and methods for the genetic engineering of host cells to render the cells and their progeny susceptible, in a regulated fashion, to programmed cell death (apoptosis). This invention is useful as a means for eliminating a population of engineered cells, whether growing in culture or in vivo, and thus provides, inter alia, a fail-safe mechanism for genetically engineered cells used in gene therapy.

The invention involves novel chimeric (or "fused") proteins, DNA constructs encoding them, and ligand molecules capable of oligomerizing the chimeric proteins. The chimeric proteins contain at least one ligand-binding (or "receptor") domain fused to an action domain capable of initiating apoptosis within a cell, as described in detail below. As will also be described, the chimeric proteins may also contain additional domains. The chimeric proteins are recombinant in the sense that the various domains are derived from different sources, and as such, are not found together in nature (i.e., are heterologous);

This invention provides DNA molecules ("constructs") which encode the novel chimeric proteins and which may be used for the genetic engineering of host cells. These constructs are recombinant in the sense that the component portions, e.g. encoding a particular domain or expression control sequence, are not found directly linked to one another in nature. Also provided are methods and compositions for producing and using the modified cells.

To produce the modified cells one introduces DNA encoding the desired chimera(s) into selected host cells. This may be accomplished using conventional vectors (various examples of which are commercially available) and techniques. If desired, the modified cells may then be selected, separated from other cells and cultured, again by conventional methods.

The oligomerizing ligands useful in practicing this invention are capable of binding to two (or more) of the receptor domains, i.e. to two or more chimeric proteins containing such receptor domains. The oligomerizing ligand may bind to the chimera in either order or simultaneously, preferably with a Kd value below about $10^{-6}$, more preferably below about $10^{-7}$, even more preferably below about $10^{-8}$, and in some embodiments below about $10^{-9}$ M. The ligand preferably is a non-protein and has a molecular weight of less than about 5 kDa. The receptor domains of the chimeric proteins so oligomerized may be the same or different. The chimeric proteins are capable of initiating apoptosis of their host cell upon exposure to the ligand, i.e., following oligomerization of the chimera. Thus, apoptosis of genetically engineered cells of this invention occurs following exposure of the cells to a ligand capable of oligomerizing the chimera. Said differently, genetically engineered cells of this invention contain chimeric proteins as described above and are responsive to the presence of a ligand which is capable of oligomerizing those chimera. That responsiveness is manifested by the initiation of cell death.

The encoded chimeric protein may further comprise an intracellular targeting domain capable of directing the chimeric protein to a desired cellular compartment. The targeting domain can be a secretory leader sequence, a membrane spanning domain, a membrane binding domain or a sequence directing the protein to associate with vesicles or with the nucleus, for instance.

The action domains of the chimeric proteins may be selected from any of the proteins or protein domains (preferably of human origin or sequence) which trigger apoptosis upon crosslinking, including, for example, the cytoplasmic domain of the Fas antigen.

As discussed in greater detail later, and by way of example, in various embodiments of this invention the chimeric protein is capable of binding to an FK506-type ligand, a cyclosporin A-type ligand, tetracycline or a steroid ligand. Such binding leads to oligomerization of the chimeric protein with other chimeric protein molecules which may be the same or different.

In addition to the construct(s) encoding the chimera described above (the "primary" chimera), the cells may optionally further contain additional heterologous DNA constructs for the regulatable or constitutive expression of one or more desired genes. For example, the cells may additionally contain one or more other constructs encoding optional chimera, otherwise as described above but containing action domains which, upon ligand-induced oligomerization, trigger biological events other than apoptosis. Such other action domains may be selected from a broad variety of protein domains capable of effecting a desired biological result upon oligomerization of the chimeric protein(s). For instance, the action domain may comprise a protein domain such as a CD3 zeta subunit capable, upon exposure to the ligand and subsequent oligomerization, of initiating a detectable intracellular signal; a DNA-binding protein such as GAL4; or a transcriptional activation domain such as VP16. Numerous other examples are provided herein. One example of a detectable intracellular signal is a signal activating the transcription of a gene under the transcriptional control of a transcriptional control element (e.g. enhancer and/or promoter elements and the like) which is responsive to the oligomerization. Preferably the ligand(s) which oligomerize the primary chimera and lead to apoptosis do not cause oligomerization of the optional chimeric proteins. It is usually even more preferable that the ligand(s) which oligomerize the optional chimera and effect the optional biological events, such as regulated gene transcription, do not lead to oligomerization of the primary chimera or trigger apoptosis. The different sets of ligands are in that sense orthogonal.

As is discussed in greater detail later, in various embodiments of is invention the chimeric proteins are capable of binding to an FK506-type ligand, a cyclosporin A-type ligand, tetracycline or a steroid ligand. Such binding leads to oligomerization of the chimeric protein molecules with other chimeric protein molecules which may be the same or different.

Optionally the cells may contain still another recombinant construct or series of such construct(s), containing a target gene under the transcriptional control of a transcriptional control element (e.g. promoter/enhancer) responsive to a signal triggered by ligand-mediated oligomerization of optional chimeric proteins, i.e. to exposure of the cells to the relevant ligand. These constructs are recombinant in the sense that the target gene is not naturally under the transcriptional control of the responsive transcriptional control element.

Such an optional target gene construct may contain (a) a transcriptional control element responsive to the oligomerization of an optional chimeric protein as described above, and (b) flanking DNA sequence from a target gene permitting the homologous recombination of the transcriptional control element into a host cell in association with the target gene. In other embodiments the construct contains a desired gene and flanking DNA sequence from a target locus permitting the homologous recombination of the target gene into the desired locus. (See e.g., Mansour et al, 1988, Nature 336, 348–352 and subsequent papers by M. Capecchi et al.) The construct may also contain the responsive transcriptional control element, or the responsive element may be provided by the locus. The target gene may encode, e.g., a surface membrane protein, a secreted protein, a cytoplasmic protein or a ribozyme or an antisense sequence.

The constructs of this invention may also contain a selectable marker permitting transfection of the constructs into host cells and selection of transfectants containing the construct. This invention further encompasses DNA vectors containing the various constructs described herein, whether for introduction of the constructs into host cells in tissue culture or for administration to whole organisms for introduction into cells in vivo. In either case the construct may be introduced episomally or for chromosomal integration. The vector may be a viral vector, including for example an adeno-, adeno associated- or retroviral vector.

This invention further encompasses a chimeric protein encoded by any of our DNA constructs, as well as cells containing and/or expressing them, including prokaryotic and eucaryotic cells and in particular, yeast, worm insect, mouse or other rodent, and other mammalian cells, including human cells, of various types and lineages, whether frozen or in active growth, whether in culture or in a whole organism containing them.

To recap, this invention provides cells, preferably but not necessarily mammalian, which contain a first DNA construct encoding a primary chimeric protein comprising (i) at least one receptor domain capable of binding to a selected oligomerizing ligand of this invention and (ii) another protein domain, heterologous with respect to the receptor domain but capable, upon oligomerization with one or more other like domains, of triggering apoptosis of the cells. Following exposure of the cells to the selected ligand, programmed cell death ensues.

In some embodiments, the cells, as just described, also contain one or more optional DNA constructs encoding one or more chimeric proteins comprising (i) at least one receptor domain capable of binding to a selected oligomerizing ligand of this invention and (ii) another protein domain, heterologous with respect to the receptor domain, but capable, upon oligomerization of these optional chimera, of triggering (directly or indirectly) the activation of transcription of a target gene under the transcriptional control of a transitional control element responsive to said oligomerization. The cells will usually also contain a target gene under the expression control of a transitional control element responsive to said oligomerization ligand. Following exposure to the selected ligand the target gene is expressed. Again, the ligand capable of oligomerizing the primary chimera and the ligand(s) capable of oligomerizing the optional chimera should be orthogonal.

In other embodiments, the cells of this invention also contain a DNA construct encoding a first optional chimeric protein containing a DNA-binding domain and at least one receptor domain capable of binding to a first selected ligand moiety. The cells further contain a second optional chimeric protein containing a transcriptional activating domain and at least one receptor domain capable of binding to a second selected ligand moiety (which may be the same or different from the first selected ligand moiety). The cells additionally contain a DNA construct encoding a target gene under the transcriptional control of a heterologous transcriptional control sequence with a cognate binding site for the DNA-binding domain and which is responsive to the transcriptional activating domain such that the cell expresses the target gene following exposure to an oligomerizing ligand containing the selected ligand moiety(ies).

DNA compositions useful for practicing aspects of the invention include those which encode the optional chimera. Those compositions comprise a first DNA construct encoding a chimeric protein comprising at least one receptor domain, capable of binding to a selected ligand, fused to a heterologous additional protein domain capable of initiating a biological process upon exposure to the oligomerizing ligand, i.e. upon oligomerization of the chimeric protein; and a second DNA construct encoding a target gene under the transcriptional control of a transcription control element responsive to the oligomerization ligand.

Another exemplary DNA composition useful in practicing aspects of this invention comprises a first series of DNA constructs encoding a first and second chimeric protein and a second DNA construct encoding a target gene under the transcriptional control of an transcription control element responsive to the oligomerization of the chimeric protein molecules. The DNA construct encoding the first chimeric protein comprises (a) at least one first receptor domain, capable of binding to a selected first ligand moiety, fused to (b) a heterologous additional protein domain capable of initiating a biological process upon [exposure to the oligomerization ligand, i.e. upon oligomerization of the first chimeric protein to a second chimeric protein molecule. The DNA construct encoding the second chimeric protein comprises (i) at least one receptor domain, capable of binding to a selected second ligand moiety, fused to (ii) a heterologous additional protein domain capable of initiating a biological process upon exposure to the oligomerization ligand, i.e., upon oligomerization to the first chimeric protein. The first and second receptor moieties in such cases may be the same or different and the first and second selected ligand moieties may likewise be the same or different.

DNA constructs encoding primary and/or optional chimeric proteins of this invention may contain cell type specific transcriptional regulatory elements. Such elements provide for tissue-specific expression of the chimeras and thus for tissue-specific biological activity triggered by their multimerization. To create transgenic animals containing modified cells of this invention one may transfect the desired constructs into ES cells, if they are available, or microinject the desired constructs directly into early embryos. See e.g. Watson et al, RECOMBINANT DNA (2d ed. 1992), esp. Chaps 14 and 24. In the latter case, use of a tissue-specific expression control sequence (promoter/enhancer) in the primary construct permits tissue-specific expression of the primary chimeric protein(s). That in turn permits tissue-specific, ligand-regulatable triggering of apoptosis, i.e., ligand-inducible ablation of cells in a tissue-specific manner. By incorporation of a cell-type specific transcriptional regulatory element in the optional chimera (in the presence or absence of constructs for the primary chimera), ligand-regulated transcription of a target gene or triggering of other biological events can likewise be achieved in a tissue-specific manner. Animals and their progeny may be conveniently characterized by conventional genetic analysis. It should also be noted that in addition to introduction into ES cells or early embryos, the constructs may also be introduced by administration, e.g. in suitable vehicles or vectors, directly into the desired tissue of the whole organisms.

Our ligands are molecules capable of binding to two or more chimeric protein molecules of this invention to form an oligomer thereof, and have the formula:

linker-{$rbm_1$, $rbm_2$, . . . $rbm_n$} wherein n is an integer from 2 to about 5, $rbm_{(1)}$–$rbm_{(n)}$ are receptor binding moieties which may be the same or different and which are capable of binding to the chimeric protein(s). The rbm moieties are covalently attached to a linker moiety which is a bi- or multi-functional molecule capable of being covalently linked ("-") to two or more rbm moieties. Preferably the ligand has a molecular weight of less than about 5 kDa and is not a protein. Examples of such ligands include those in which the rbm moieties are the same or different and comprise an FK506-type moiety, a cyclosporin-type moiety, a steroid or tetracycline. Cyclosporin-type moieties include cyclosporin and derivatives thereof which are capable of binding to a cyclophilin, naturally occurring or modified, preferably with a Kd value below about $10^{-6}$ M. In some embodiments it is preferred that the ligand bind to a naturally occurring receptor with a Kd value greater than about $10^{-6}$M and more preferably greater than about $10^{-5}$ M. Illustrative ligands of this invention are those in which at least one rbm comprises a molecule of FK506, FK520, rapamycin or a derivative thereof modified at C9, C10 or both, which ligands bind to a modified receptor or chimeric molecule containing a modified receptor domain with a Kd value at least one, and preferably 2, and more preferably 3 and even more preferably 4 or 5 or more orders of magnitude less than their Kd values with respect to a naturally occurring receptor protein. Linker moieties are also described in detail later, but for the sake of illustration, include such moieties as a C2–C20 alkylene, C4–C18 azalkylene, C6–C24 N-alkylene azalkylene, C6–C18 arylene, C8–C24 ardialkylene or C8–C36 bis-carboxamido alkylene moiety.

The monomeric rbm's of this invention, as well as compounds containing sole copies of an rbm, which are capable of binding to our chimeric proteins but not effecting dimerization or higher order oligomerization thereof (in view of the monomeric nature of the individual rbm) are oligomerization antagonists.

In an important aspect of ties invention, genetically engineered cells of this invention can be grown together with other cells and can be selectively ablated from the mixture of cells by addition of an effective amount of an oligomerization ligand which corresponds to (i.e. is capable of binding to) the primary chimeric protein. Thus, contacting the cells with the oligomerization ligand triggers cell death in the engineered cells. For example, such cells may be permitted to produce an endogenous or heterologous product for some desired period, and may then be deleted by addition of the ligand. In such cases, the cells are engineered to produce a primary chimera in accordance with this invention. The cells, which may be further engineered to express a desired gene under ligand-induced regulation, may be grown in culture by conventional means. In that case, addition to the culture medium of the ligand for the optional chimera leads to expression of the desired gene and production of the desired protein. Expression of the gene and production of the protein can then be turned off by adding to the medium an oligomerization antagonist reagent, as is described in detail below. In other cases, production of the protein is constitutive. In any event, the engineered cells can then be eliminated from the cell culture after they have served their intended purpose (e.g. production of a desired protein or other product) by adding to the medium an effective amount of the appropriate oligomerizing ligand to cause oligomerization of the primary chimera and induce apoptosis in the engineered cells. Engineered cells of this invention can also be used in vivo, to modify whole organisms, preferably animals, including humans, e.g. such that the cells produce a desired protein or other result within the animal containing such cells. Such uses include gene therapy. Alternatively, the chimeric proteins and oligomerizing molecules can be used extracellularly to bring together proteins which act in concert to initiate a physiological action.

This invention thus provides materials and methods for selectively ablating cells in response to the addition of an oligomerizing ligand. The method involves providing cells engineered in accordance with this invention and exposing the cells to the ligand.

Thus, this invention provides a method for using cells engineered as described herein for producing a heterologous protein via regulated activation of transcription of a target gene in the cells and for eliminating the engineered cells when desired. The method involves providing cells of this invention which express a primary chimeric protein capable, upon oligomerization, of initiating apoptosis, and which cells further contain and are capable of expressing (a) at least one DNA construct encoding a chimeric protein capable, following oligomerization, of activating transcription of (b) a target gene. The chimeric protein comprises at least one receptor domain capable of binding to a selected oligomerization ligand. The receptor domain is fused to an action domain capable—on exposure to the oligomerizing ligand, i.e., upon oligomerization with one or more other chimeric proteins containing another copy of the action domain—of initiating an intracellular signal. That signal is capable of activating transcription of a gene, such as the target gene in this case, which is under the transcriptional control of a transcriptional control element responsive to that signal. The method thus involves exposing the cells to an oligomerization ligand capable of binding to the chimeric protein in an amount effective to result in expression of the target gene. In cases in which the cells are growing in culture, exposing them to the ligand is effected by adding the ligand to the culture medium. In cases in which the cells are present within a host organism, exposing them to the ligand is effected by administering the ligand to the host organism. For instance, in cases in which the host organism is an animal, in particular, a mammal (including a human), the ligand is administered to the host animal by oral, bucal, sublingual, transdermal, subcutaneous, intramuscular, intravenous, intra-joint or inhalation administration in an appropriate vehicle therefor. To ablate the engineered cells, one adds to the culture medium or administers to the host organism, as the case may be, a second oligomerizing ligand which is capable of oligomerizing the primary chimera.

This invention further encompasses pharmaceutical compositions for eliminating genetically engineered cells of this invention from a mixture of different cells, including from animal tissue or from a subject containing such engineered cells. Such pharmaceutical compositions comprise an oligomerization ligand of this invention in admixture with a pharmaceutically acceptable carrier and optionally with one or more pharmaceutically acceptable excipients. The oligomerization ligand can be a homo-oligomerization reagent or a hetero-oligomerization reagent as described in detail elsewhere so long as it is capable of binding to a primary chimeric protein of this invention or triggering apoptosis of engineered cells of this invention. Likewise, this invention further encompasses a pharmaceutical composition comprising an oligomerization antagonist of this invention admixture with a pharmaceutically acceptable carrier and optionally with one or more pharmaceutically acceptable excipients for preventing or reducing, in whole or part, the level of oligomerization of chimeric proteins in engineered cells of this invention, in cell culture or in a subject, and thus for preventing or de-activating cell death in the relevant cells. Thus, the use of the oligomerization reagents and of the oligomerization antagonist reagents to prepare pharmaceutical compositions is encompassed by this invention.

This invention also offers a method for providing a host organism, preferably an animal, and in many cases a mammal, responsive to an oligomerization ligand of his invention. The method involves introducing into the organism cells which have been engineered ex vivo in accordance with this invention, i.e. containing a DNA construct encoding a chimeric protein hereof, and so forth. Alternatively, one can introduce the DNA constructs of this invention into a host organism, e.g. mammal under conditions permitting transfection of one or more cells of the host mammal in vivo.

We further provide kits for producing cells susceptable to ligand-regulated apoptosis. One kit contains at least one DNA construct encoding one of our primary chimeric proteins, containing at least one receptor domain and an action domain (e.g., the cytoplasmic domain of Fas or of a TNF receptor, as described elsewhere). In one embodiment the DNA constrict contains a conventional polylinker to provide the practitioner a site for the incorporation of cell-type specific expression control element(s) (promoter and/or enhancer elements) to provide for cell-type or tissue-specific expression of one or more of the chimeras. The kit may contain a quantity of a ligand of this invention capable of oligomerizing the chimeric protein molecules encoded by the DNA constructs of the kit, and may contain in addition a quantity of an oligomerization antagonist e.g. monomeric ligand reagent. Where a sole chimeric protein is encoded by the construct(s), the oligomerization ligand is a homo-oligomerization ligand. Where more than one such chimeric protein is encoded, a hetero-oligomerization ligand may be included. The kit may further contain a additional DNA constructs encoding optional chimera and/or target gene constructs and/or a transcription control element responsive to oligomerization of the chimeric protein molecules. The DNA constructs will preferably be associated with one or more selection markers for convenient selection of transfectants, as well as other conventional vector elements useful for replication in prokaryotes, for expression in eukaryotes, and the like. The selection markers may be the same or different for each different DNA construct, permitting the selection of cells which contain various combinations of such DNA construct(s).

For example, one kit of this invention contains a DNA construct encoding a primary chimeric protein as described elsewhere; a first optional DNA construct encoding a chimeric protein containing at list one receptor domain (capable of binding to a selected ligand), fused to a transcriptional activator domain; a second optional DNA construct encoding a chimeric protein containing at least one receptor domain (capable of binding to a selected ligand), fused to a DNA binding domain; and a target gene DNA construct encoding a target gene under the control of a transcriptional control element containing a DNA sequence to which the DNA binding domain binds and which is transcriptionally activated by exposure to the ligand in the presence of the first and second optional chimeric proteins.

Alternatively, a DNA construct for introducing a target gene under the control of a responsive transcriptional control element may contain a cloning site in place of a target gene to provide a kit for engineering cells to inducably express a gene to be provided by the practitioner.

Other kits of this invention may contain one or two (or more) DNA constructs for chimeric proteins in which one or more contain a cloning site in place of an action domain (transcriptional initiation signal generator, transcriptional activator, DNA binding protein, etc.), permitting the user to insert whichever action domain s/he wishes. Such a kit may optionally include other elements as described above, e.g. DNA construct for a target gene under responsive expression control, oligomerization ligand, antagonist, etc.

Any of the kits may also contain positive control cells which were stably transformed with constructs of this invention such that they express a reporter gene (for CAT, beta-galactosidase or any conveniently detectable gene product) in response to exposure of the cells to the ligand. Reagents for detecting and/or quantifying the expression of the reporter gene may also be provided.

BRIEF DESCRIPTION OF THE FIGURES

FIG. 2 is a flow diagram of the preparation of the intracellular signaling chimera plasmids and p#MXFn and p#MFnZ, where n indicates the number of binding domains.

FIGS. 3A and 3B are a flow diagram of the preparation of the extracellular signalling chimera plasmid p#1FK3/pBJ5.

FIGS. 4A, 4B and 4C are sequences of the primers used in the constructions of the plasmids employed in the subject invention (SEQ ID NOs: 4–6, 8–10, 12, 14–35, 37–40).

FIGS. 6A and 6B is a chart of the activity of various ligands with the TAg Jurkat cells described in Example 1. For FIG. 6B, see also Spencer et al, Science 262, 1019, FIG. 3 and caption esp. 3B on p. 1020 therein.

FIGS. 9A and 9B are the chemical structures of the allyl-linked FK506 variants and the cyclohexyl-linked FK506 variants, respectively.

FIGS. 11A and B are a flow diagram of a synthesis of derivatives of FK520 and chemical structures of FK520, where the bottom structures are designed to bind to mutant FKBP12.

FIGS. 16A and 16B depicts synthetic schemes for HOD and HOD reagents based on FK506-type moieties.

DESCRIPTION

I. General Discussion

This invention provides chimeric proteins, organic molecules for oligomerizing the chimeric proteins and a system for using them. The fused proteins (chimeras) have a binding domain for binding to the (preferably small) organic oligomerizing molecule and an action domain, which can effectuate a physiological action or cellular process as a result of oligomerization of the chimeric proteins.

Figure 14:
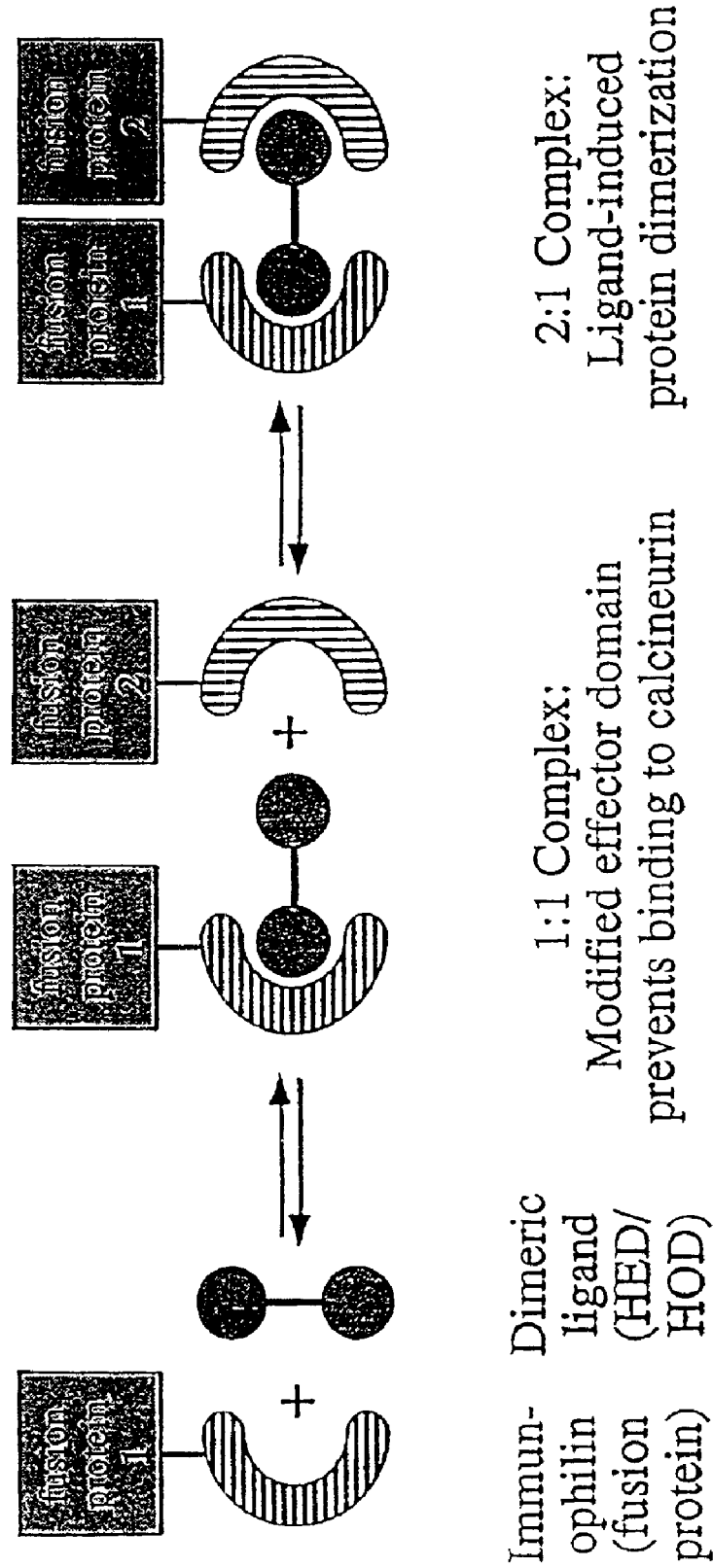
FIG. 14 is a schematic representation of the oligomerization of chimeric proteins, illustrated by chimeric proteins containing an immunophilin moiety as the receptor domain.

The basic concept for inducible protein association is illustrated in FIG. 14. Ligands which can function as heterodimerization (or hetero-oligomerization, "HED") and homodimerization (or homo-oligomerization, "HOD") agents are depicted as dumbell-shaped structures.

(Homodimerization and homo-oligomerization refer to the association of like components to form dimers or oligomers, linked as they are by the ligands of this invention. Heterodimerization and hetero-oligomerization refer to the association of dissimilar components to form dimers or oligomers. Homo-oligomers thus comprise an association of multiple copies of a particular component while hetero-oligomers comprise an association of copies of different components. "Oligomerization", "oligomerize" and "oligomer", as the terms are used herein, with or without prefixes, are intended to encompass "dimerization", "dimerize" and "dimer", absent an explicit indication to the contrary.)

Also depicted in FIG. 14 are fusion protein molecules containing a target protein domain of interest ("action domain") and one or more receptor domains that can bind to the ligands. For intracellular chimeric proteins, i.e., proteins which are located within the cells in which they are produced, a cellular targeting sequence (including organelle targeting amino acid sequences) will preferably also be present. Binding of the ligand to the receptor domains hetero- or homodimerizes the fusion proteins. Oligomerization brings the action domains into close proximity with one another thus triggering cellular processes normally associated with the respective action domain—such as apotosis or TCR-mediated signal transduction, for example.

Cellular processes which can be triggered by oligomerization include a change in state, such as a physical state, e.g. conformational change, change in binding partner, cell death, initiation of transcription, channel opening, ion release, e.g. $Ca^{+2}$ etc. or a chemical state, such as an enzymatically catalyzed chemical reaction, e.g. acylation, methylation, hydrolysis, phosphorylation or dephosphorylation, change in redox state, rearrangement, or the like. Thus, any such process which can be triggered by ligand-mediated oligomerization is included within the scope of this invention, although a primary focus here is apoptosis.

In a central feature of this invention, cells are modified so as to be responsive to ligand molecules which are capable of binding to, and thus oligomerizing the primary chimeras disclosed herein. See e.g. Examples 4(B) and 4(C), infra. Such engineered cells respond to the presence of ligand by undergoing apoptosis and may thus be eliminated in applications of gene therapy and other situations where it is necessary or desirable to ablate the genetically modified cells. For example, the modified cells may become cancerous or otherwise deleterious or superfluous.

The modified cells are characterized by a genome containing a genetic construct (or series thereof encoding a primary chimeric protein of this invention, which permits ligand-regulated apoptosis. The primary chimera contains, e.g., the cytoplasmic domain of the fas antigen or Apo-1 antigen, which when cross-liked, induces apoptosis in most cell types (Trauth et al. (1989) Science 245, 301–305; Watanaba-Fukunaga et al. (1992) Nature 356, 314). In this way one can provide for ligand-inducable cell death for an engineered population of cells.

The cells may be further engineered to produce optional additional chimeric proteins capable of binding with, and being responsive to, selected ligand molecules. Such further optional engineering imparts additional ligand-regulatable functionality on the cells, which can be used in applications involving in vitro cell culture and in gene therapy applications. Preferably, the ligand molecules which are capable of binding to the optional additional chimera(s) and regulating the optional additional cellular processes (such as gene transcription, for example) do not cross react with the primary chimera molecules, and therefore do not trigger apoptosis in the engineered cells.

Such further modified cells can be used in applications in which regulation of cellular processes such as transcription or translation (both are included under the term expression) of a target gene is desired. Such cells are characterized by a genome containing at least a first or first series (the series may include only one construct) of genetic constructs encoding the optional additional chimeras, and desirably a second or second series (the series may include only one construct) of target gene constructs.

The nature and number of such genetic constructs will depend on the nature of the chimeric protein and the role it plays in the cell. For instance, in embodiments where the optional additional chimeric protein is to be associated with expression of a target gene (and which may contain an intracellular targeting sequence or domain which directs the chimeric protein to be associated with the cellular surface membrane or with an organelle e.g. nucleus or vesicle), then there will normally be at least two series of such additional constructs: a first series encoding the chimeric protein(s) which upon ligand-mediated oligomerization initiate a signal directing target gene expression, and desirably a second series which comprise the target gene and/or expression control elements therefor which are responsive to the signal.

Only a single construct in the first series will be required where a homooligomer, usually a homodimer, is involved, while two or more, usually not more than three constructs may be involved, where a heterooligomer is involved. The chimeric proteins encoded by the first series of constructs will be associated with actuation of gene transcription and will normally be directed to the surface membrane or the nucleus, where the oligomerized chimeric protein is able to initiate, directly or indirectly, the transcription of one or more target genes. A second series of additional constructs will be required where an exogenous gene(s) is introduced, or where an exogenous or recombinant expression control sequence is introduced (e.g. by homologous recombination) for expression of an endogenous gene, in either case, whose transcription will be activated by the oligomerizing of the chimeric protein.

A different first series of additional constructs is employed where the chimeric proteins are intracellular and can act directly without initiation of transcription of another gene. For example, proteins associated with exocytosis can be expressed inducibly or constitutively, where the proteins will not normally complex except in the presence of the oligomerizing molecule. By employing proteins which have any or all of these properties which do not complex in the host cell; are inhibited by complexation with other proteins, which inhibition may be overcome by oligomerization with the ligand; require activation through a process which is not available in the host cell, or by modifying the proteins which direct fusion of a vesicle with the plasma membrane to form chimeric proteins, where the extent of complex formation and membrane fusion is enhanced in the presence of the oligomerizing molecule, exocytosis is or has the ability to be induced by the oligomerizing molecule.

Other intracellular proteins, such as kinases, phosphatases and cell cycle control proteins can be similarly modified and used.

Various classes of optional additional genetic constructs useful in the practice of is invention are described as follows:

(1) constructs which encode a chimeric protein comprising a binding domain and an action domain, where the binding domain is extracellular or intracellular and the action domain is intracellular such that ligand-mediated oligomerization of the chimeric protein by itself (to form a homo-oligomer) or with a different fused protein comprising a different action domain (to form a hetero-oligomer), induces a signal which results in a series of events resulting in transcriptional activation of one or more genes;

(2) constructs which encode a chimeric protein having a binding domain and an action domain, where the binding domain and action domain are in the nucleus, such that ligand-mediated oligomerization of the protein, by itself (to form a homo-oligomer) or with a different fused protein comprising a different action domain (to form a heterooligomer), induces initiation of transcription directly via complexation of the oligomer(s) with the DNA transcriptional initiation region;

(3) constructs which encode a chimeric protein containing a binding domain and an action domain, where the binding domain and the action domain are cytoplasmic, such that ligand-mediated oligomerization of the protein, by itself (to form a homo-oligomer) or with a different fused protein comprising a different action domain (to form a hetero-oligomer), results in exocytosis; and (4) constructs which encode a chimeric protein containing a binding domain and an action domain, where the binding domain and action domain are extracellular and the action domain is associated with initiating a biological activity (by way of non-limiting illustration, the action domain can itself bind to a substance, receptor or other membrane protein yielding, upon ligand-mediated oligomerization of the chimeras, the bridging of one or more similar or dissimilar molecules or cells); and, (5) constructs which encode a destabilizing, inactivating or short-lived chimeric protein having a binding domain and an action domain, such that ligand-mediated oligomerization of the protein with a target protein comprising a different action domain leads to the destabilization and/or degradation or inactivation of said oligomerized target protein.

II. Transcription Regulation

The construct(s) of Groups (1) and (2), above, will be considered first. Group (1) constructs differ from group (2) constructs in their effect Group (1) constructs are somewhat pleiotropic, i.e. capable of activating a number of wild-type genes, as well as the target gene(s). In addition, the response of the expression products of group (1) genes to the ligand is relatively slow. Group (2) constructs can be directed to a specific target gene and are capable of limiting the number of genes which will be transcribed. The response of expression products of group (2) constructs to the ligand is very rapid.

The subject system for groups (1) and (2) will include a first series of constructs which comprise DNA sequences encoding the chimeric proteins, usually involving from one to three, usually one to two, different constructs. The system usually will also include a second series of constructs which will provide for expression of one or more genes, usually an exogenous gene. By "exogenous gene" is meant a gene which is not otherwise normally expressed by the cell, e.g. because of the nature of the cell, because of a genetic defect of the cell, because the gene is from a different species or is a mutated or synthetic gene, or the like. Such gene can encode a protein, antisense molecule, ribozyme etc., or can be a DNA sequence comprising an expression control sequence linked or to be linked to an endogenous gene with which the expression control sequence is not normally associated. Thus, as mentioned before, the construct can contain an exogenous or recombinant expression control sequence for ligand-induced expression of an endogenous gene.

The chimeric protein encoded by a construct of groups (1), (2) and (3) can have, as is often preferred, an intracellular targeting domain comprising a sequence which directs the chimeric protein to the desired compartment, e.g. surface membrane, nucleus, vesicular membrane, or other site, where a desired physiological activity can be initiated by the ligand-mediated oligomerization, at least dimerization, of the chimeric protein.

The chimeric protein contains a second ("binding" or "receptor") domain which is capable of binding to at least one ligand molecule. Since the ligand can contain more than one binding site or epitope, it can form dimers or higher order homo- or hetero-oligomers with the chimeric proteins of this invention. The binding domain of the chimeric protein can have one or a plurality of binding sites, so that homooligomers can be formed with a divalent ligand. In this way the ligand can oligomerize the chimeric protein by having two or more epitopes to which the second domain can bind, thus providing for higher order oligomerization of the chimeric protein.

The chimeric protein also contains a third ("action") domain capable of initiating a biological activity upon ligand-mediated oligomerization of chimeric protein molecules via the binding domains. Thus, the action domain may be associated with transduction of a signal as a result of the ligand-mediated oligomerization. Such signal, for instance, could result in the initiation of transcription of one or more genes, depending on the particular intermediate components involved in the signal transduction. See FIG. 15 which depicts an illustrative chimeric protein in which the intracellular targeting domain comprises a myristate moiety; the receptor domain comprises three FKBP12 moieties; and the action domain comprises a zeta subunit. In other chimeric proteins the action domains may comprise transcription factors, which upon oligomerization, result in the initiation of transcription of one or more target genes, endogenous and/or exogenous. The action domains can comprise proteins or portions thereof which are associated with fusion of vesicle membranes with the surface or other membrane, e.g. proteins of the SNAP and SNARE groups (See, Sollner et al., Nature (1993) 362, 318 and 353; Cell (1993) 72, 43).

A. Surface Membrane Receptor

One class of additional optional chimeric proteins of this invention are involved with the surface membrane and are capable of transducing a signal leading to the transcription of one or more genes. The process involves a number of auxiliary proteins in a series of interactions culminating in the binding of transcription factors to promoter regions associated with the target gene(s). In cases in which the transcription factors bind to promoter regions associated with other genes, transcription is initiated there as well. A construct encoding a chimeric protein of this embodiment can encode a signal sequence which can be subject to processing and therefore may not be present in the mature chimeric protein. The chimeric protein will in any event comprise (a) a binding domain capable of binding a predetermined ligand, (b) an optional (although in many embodiments, preferred) membrane binding domain which includes a transmembrane domain or an attached lipid for translocating the fused protein to the cell surface/membrane and retaining the protein bound to the cell surface membrane, and, (c) as the action domain, a cytoplasmic signal initiation domain. The cytoplasmic signal initiation domain is capable of initiating a signal which results in transcription of a gene having a recognition sequence for the initiated signal in the transcriptional initiation region.

Figure 15:
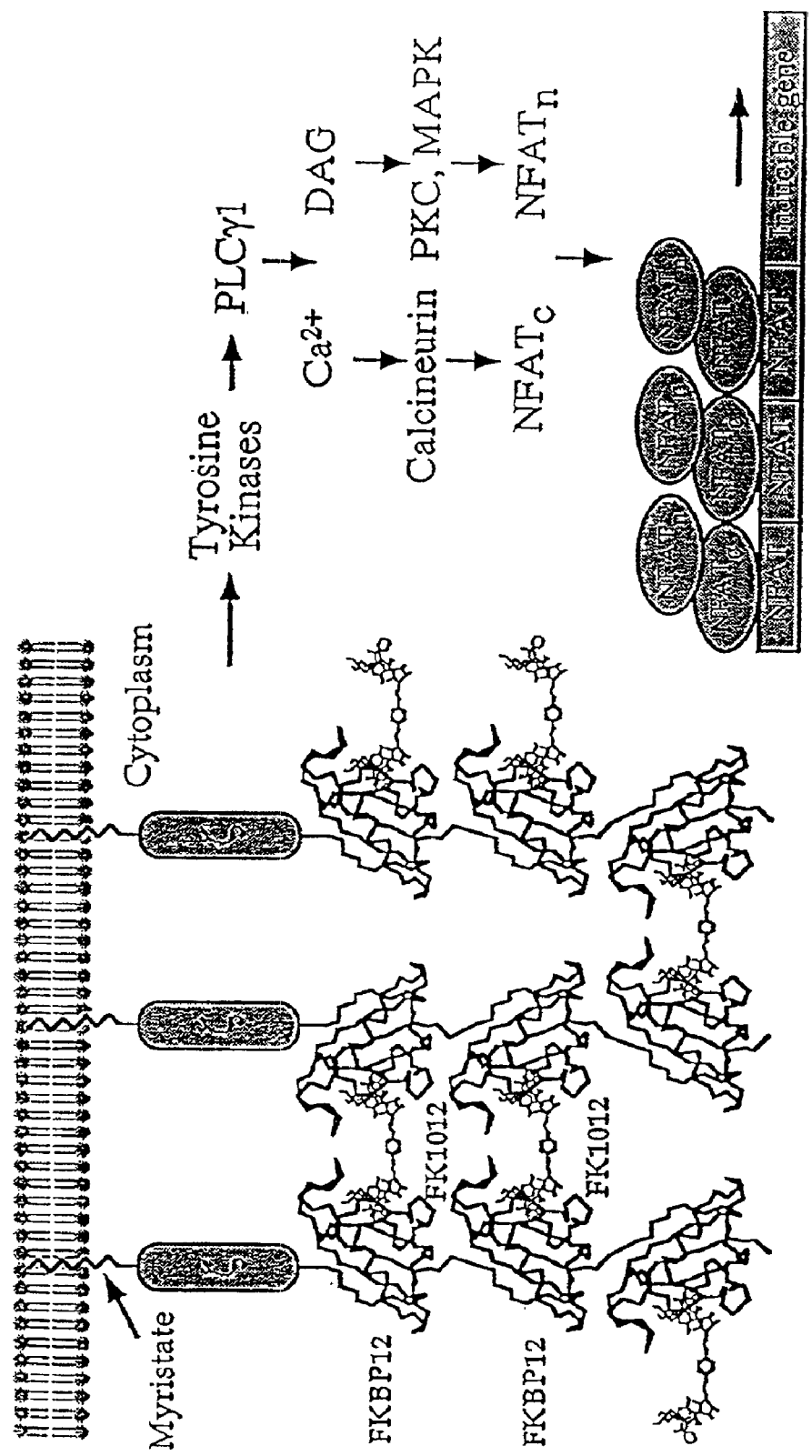
FIG. 15 depicts ligand-mediated oligomerization of chimeric proteins, showing schematically the triggering of a transcriptional initiation signal.

The gene whose expression is regulated by the signal from the chimeric protein is referred to herein as the "target" gene, whether it is an exogenous gene or an endogenous gene under the expression control of an endogenous or exogenous (or hybrid) expression control sequence. The molecular portion of the chimeric protein which provides for binding to a membrane is also referred to as the "retention domain". Suitable retention domains include a moiety which binds directly to the lipid layer of the membrane, such as through lipid participation in the membrane or extending through the membrane, or the like. In such cases the protein becomes translocated to and bound to the membrane, particularly the cellular membrane, as depicted in FIG. 15.

B. Nuclear Transcription Factors

Another optional first construct encodes a chimeric protein containing a cellular targeting sequence which provides for the protein to be translocated to the nucleus. This ("signal consensus") sequence has a plurality of basic amino acids, referred to as a bipartite basic repeat (reviewed in Garcia-Bustos et al, Biochimica et Biophysica Acta (1991) 1071, 83–101). This sequence can appear in any portion of the molecule internal or proximal to the N- or C-terminus and results in the chimeric protein being inside the nucleus. The practice of one embodiment of this invention will involve at least two ("first series") chimeric proteins: (1) one having an action domain which binds to the DNA of the transcription initiation region associated with a target gene and (2) a different chimeric protein containing as an action domain, a transcriptional activation domain capable, in association with the DNA binding domain of the first chimeric protein, of initiating transcription of a target gene. The two action domains or transcription factors can be derived from the same or different protein molecules.

The transcription factors can be endogenous or exogenous to the cellular host. If the transcription factors are exogenous, but functional within the host and can cooperate with the endogenous RNA polymerase (rather than requiring an exogenous RNA polymerase, for which a gene could be introduced), then an exogenous promoter element functional with the fused transcription factors can be provided with a second construct for regulating transcription of the target gene. By this means the initiation of transcription can be restricted to the gene(s) associated with the exogenous promoter region, i.e., the target gene(s).

A large number of transcription factors are known which require two subunits for activity. Alternatively, in cases where a single transcription factor can be divided into two separate functional domains (e.g. a transcriptional activator domain and a DNA-binding domain), so that each domain is inactive by itself, but when brought together in close proximity, transcriptional activity is restored. Transcription factors which can be used include yeast GAL4, which can be divided into two domains as described by Fields and Song, supra. The authors use a fusion of GAL4(1–147)-SNF1 and SNF4-GAL4(768–881), where the SNF1 and -4 may be replaced by the subject binding proteins as binding domains. Combinations of GAL4 and VP16 or HNF-1 can be employed. Other transcription factors are members of the Jun, Fos, and ATF/CREB families, Oct1, Sp1, HNF-3, the steroid receptor superfamily, and the like.

As an alternative to using the combination of a DNA binding domain and a naturally occurring activation domain or modified form thereof, the activation domain may be replaced by one of the binding proteins associated with bridging between a transcriptional activation domain and an RNA polymerase, including but not limited to RNA polymerase II. These proteins include the proteins referred to as TAFs, the TFII proteins, particularly B and D, or the like. Thus, one can use any one or combination of proteins, for example, fused proteins or binding motifs thereof, which serve in the bridge between the DNA binding protein and RNA polymerase and provide for initiation of transcription. Preferably, the protein closest to the RNA polymerase will be employed in conjunction with the DNA binding domain to provide for initiation of transcription. If desired, the subject constructs can provide for three or more, usually not more than about 4, proteins to be brought together to provide the transcription initiation complex.

Rather than have a transcriptional activation domain as an action domain, an inactivation domain, such as ssn-6/TUP-1 or Krüppel-family suppressor domain can be employed. In this manner, regulation results in turning off the transcription of a gene which is constitutively expressed. For example, in the case of gene therapy one can provide for constitutive expression of a hormone, such as growth hormone, blood proteins, immunoglobulins, etc. By employing constructs encoding one chimeric protein containing a DNA binding domain joined to a ligand binding domain and another chimeric protein containing an inactivation domain joined to a ligand binding domain, the expression of the gene can be inhibited via ligand-mediated oligomerization.

Constructs encoding a chimeric protein containing inter alia a ligand-binding domain fused to a transcriptional activating domain or subunit, transcriptional inactivating domain or DNA-binding domain are designed and assembled in the same manner as described for the other constructs. Frequently, the N-terminus of the transcription factor will be bound to the C-terminus of the ligand-binding domain, although in some cases the reverse will be true, for example, where two individual domains of a single transcription factor are divided between two different chimeras.

III. Exocytosis

Another application of the ligand-mediated oligomerization mechanism is exocytosis, where export of a protein rather than transcription is controlled by the ligand. This can be used in conjunction with the expression of one or more proteins of interest, as an alternative to providing for secretion of the protein(s) of interest via a secretory signal sequence. This embodiment involves two different first constructs. One construct encodes a chimeric protein which directs the protein to the vesicle to be integrated into the vesicular membrane as described by Sollner et al., supra. Proteins which may be used as the vesicle binding protein include VAMP (synaptobrevin), SNC2, rab3, SEC4, synaptotagmin, e, individually or in combination. The cellular membrane protein may include syntaxin, SSO1, SSO2, neurexin, etc., individually or in combination. The other construct provides for transport to the surface membrane and employs the myristoyl signal sequence, other plasma membrane targeting sequence (e.g. for prenylation) or transmembrane retention domain, as described above. The encoded proteins are described in the above references and, all or functional part, may serve as the action domains. These constructs could be used in conjunction with the expression of an exogenous protein, properly encoded for transport to a vesicle or for an endocytotic endogenous protein, to enhance export of the endogenous protein.

Various mechanisms can be employed for exocytosis. Depending on the cell type and which protein is limiting for endocytosis in the cell, one or more of the vesicle bound proteins or cellular proteins may be encoded by one or more constructs having a response element which is activated by the ligand. Of particular interest is the combination of VAMP and syntaxin. Alternatively, one can provide for constitutive expression of non-limiting proteins controlling exocytosis and provide for ligand regulated expression of the exocytosis limiting protein. Finally, one can provide for constitutive expression of the chimeric proteins associated with exocytosis, so that exocytosis is controlled by oligomerizing the chimeric proteins with the ligand. By employing appropriate binding domains, one can provide for different chimeric proteins to be oligomerized on the vesicle surface to form an active complex, and/or linking of the vesicle protein(s) with the cell membrane surface protein through the ligand. The chimeric proteins may not provide for exocytosis in the absence of the ligand due to modifications in the ligand which substantially reduce the binding affinity between the proteins governing exoytosis, such as deletions, mutations, etc. These modifications can be readily determined by employing overlapping fragments of the individual proteins and determining which fragments retain activity. The fragments can be further modified by using alanine substitutions to determine the individual amino acids which substantially affect binding (Beohncke et al., J. Immunol. (1993) 150, 331–341; Evavold et al., ibid (1992) 148, 347–353).

The proteins assembled in the lumen of the vesicle, as well as the fused proteins associated with exocytosis can be expressed constitutively or inducibly, as described above. Depending on the purpose of the exocytosis, whether endogenous or exogenous proteins are involved, whether the proteins to be exported are expressed constitutively or inducibly, whether the same ligand can be used for initiating transcription of the fused proteins associated with exocytosis and the proteins to be exported, or whether the different proteins are to be subject to different inducible signals, may determine the manner in which expression is controlled. In one aspect, the exocytosis mechanism would be the only event controlled by the ligand. In other aspects, both expression of at least one protein and exocytosis may be subject to ligand control.

Various proteins may be modified by introduction of a cellular targeting sequence for translocation of the protein to a vesicle without loss of the physiological activity of the protein. By using exocytosis as the delivery mechanism relatively high dosages may be delivered within a short period of time to produce a high localized level of the protein or a high concentration in the vascular system, depending on the nature of the host. Proteins of interest include e.g. insulin, tissue plasminogen activator, cytokines, erythropoietin, colony stimulating factors, growth factors, inflammatory peptides, cell migration factors.

Coding sequences for directing proteins to a vesicle are available from the vesicle binding proteins associated with exocytosis. See, for example, Sollner, et al. supra.

Another use of the oligomerization mechanism is the control of protein degradation or inactivation. For example, a relatively stable or long-lived chimeric protein of this invention can be destabilized or targeted for degradation by ligand-mediated oligomerization with a different chimeric protein of this invention which has a relatively short half-life or which otherwise destabilizes or targets the oligomer for degradation. In this embodiment, ligand-mediated oligomerization regulates biological functioning of a protein by conferring upon it in trans a shortened half-life. The latter chimeric protein may contain a domain targeting the protein to the lysosome or a domain rendering the protein susceptible to proteolytic cleavage in the cytosol or nucleus or non-lysosomal organelle.

The half-life of proteins within cells is determined by a number of factors which include the presence of short amino acid sequences within said protein rich in the amino acid residues proline, glutamic add, serine and threonine, hence "PEST", other sequences with similar function, protease sensitive cleavage sites and the state of ubiquitinization. Ubiquitinization is the modification of a protein by one or more units of the short polypeptide chains ubiquitin, which targets proteins for degradation. The rate of ubiquitinization of proteins is considered to be determined primarily by the identity of the N-terminal amino acid of the processed protein and one or more unique lysine residues near the amino terminus.

IV. Other Regulatory Systems

Other biological functions which can be controlled by oligomerization of particular activities associated with individual proteins are protein kinase or phosphatase activity, reductase activity, cyclooxygenase activity, protease activity or any other enzymatic reaction dependent on subunit association. Also, one may provide for association of G proteins with a receptor protein associated with the cell cycle, e.g. cyclins and cdc kinases, multiunit detoxifying enzymes.

V. Components of Constructs

The second or additional optional constructs (target gene constructs) associated with group (1) and (2) optional additional chimeric proteins comprise a transcriptional initiation region having the indicated target recognition sequence or responsive element, so as to be responsive to signal initiation from the activated receptor or activated transcription factors resulting in at least one gene of interest being transcribed to a sequence(s) of interest, usually mRNA, whose transcription and, as appropriate, translation may result in the expression of a protein and/or the regulation of other genes, e.g. antisense, expression of transcriptional factors, expression of membrane fusion proteins, etc.

For the different purposes and different sites, different binding domains and different cytoplasmic domains will be used. For chimeric protein receptors associated with the surface membrane, if the ligand-binding domain is extracellular, the chimeric protein can be designed to contain an extracellular domain selected from a variety of surface membrane proteins. Similarly, different cytoplasmic or intracellular domains of the surface membrane proteins which are able to transduce a signal can be employed, depending on which endogenous genes are regulated by the cytoplasmic portion. Where the chimeric protein is internal, internal to the surface membrane protein or associated with an organelle, e.g. nucleus, vesicle, etc., the ligand-binding domain protein will be restricted to domains which can bind molecules which can cross the surface membrane or other membrane, as appropriate. Therefore, these binding domains will generally bind to small naturally occurring or synthetic ligand molecules which do not involve proteins or nucleic acids.

A. Cytoplasmic Domains

A chimeric protein receptor of Group (1) can contain a cytoplasmic domain from one of the various cell surface membrane receptors or variants thereof (or other action domains for that matter) for which a corresponding recognition sequence is known or available which is capable of initiating transcription in response to multimerization of the chimeric proteins. Such recognition sequences include those associated with a gene responsive to transcriptional activation triggered by such a receptor. Mutant receptors of interest will dissociate transcriptional activation of a target gene from activation of genes which can be associated with harmful side effects, such as deregulated cell growth or inappropriate release of cytokines. The receptor-associated cytoplasmic domains of particular interest will have the following characteristics: receptor activation leads to initiation of transcription for relatively few (desirably fewer than 100) and generally innocuous genes in the cellular host; the other factors necessary for transcription initiated by receptor activation are present in the cellular host; genes which are activated other than the target genes will not affect the intended purpose for which these cells are to be used; oligomerization of the cytoplasmic domain or other available mechanism results in signal initiation; and joining of the cytoplasmic domain to a desired ligand-binding domain will not interfere with signalling. A number of different cytoplasmic domains are known. Many of these domains are tyrosine kinases or are complexed with tyrosine kinases, e.g. CD3 ζ, IL-2R, IL-3R, etc. For a review see Cantley, et al., *Cell* (1991) 64, 281. Tyrosine kinase receptors which are activated by crosslinking, e.g. dimerization (based on nomenclature first proposed by Yarden and Ulrich, *Annu. Rev. Biochem.* (1988) 57, 443, include subclass I: EGF-R, ATR2/neu, HER2/neu, HER3/c-erbB-3, Xmrk; subclass II: insulin-R, IGF-1-R [insulin-like growth factor receptor], IRR; subclass III: PDGF-R-A, PDGF-R-B, CSF-1-R (M-CSF/c-Fms), c-kit, STK-1/Flk-2; and subclass IV: FGF-R, flg [acidic FGF], bek [basic FGF]); neurotrophic tryosine kinases: Trk family, includes NGF-R, Ror1,2. Receptors which associate with tyrosine kinases upon a cross-linking include the CD3 ζ-family: CD3 ζ and CD3 η (found primarily in T cells, associates with Fyn); β and γ chains of Fc_εRI (found primarily in mast cells and basophils); γ chain of Fc_γRIII/CD16 (found primarily in macrophages, neutrophils and natural killer cells); CD3 γ, -δ, and -ε (found primarily in T cells); Ig-α/MB-1 and Ig-β/B29 (found primarily in B cell). Many cytokine and growth factor receptors associate with common β subunits which interact with tyrosine kinases and/or other signalling molecules and which can be used as cytoplasmic domains in chimeric proteins of this invention. These include (1) the common β subunit shared by the GM-CSF, IL-3 and IL-5 receptors; (2) the β chain gp130 subunit associated with the IL-6, leukemia inhibitory factor (LIF), ciliary neurotrophic factor (CNTF), oncostatin M, and IL-11 receptors; (3) the IL-2 receptor γ subunit associated also with receptors for IL-4, IL-7 and IL-13 (and possibly IL-9); and (4) the β chain of the IL-2 receptor which is homologous to the cytoplasmic domain of the G-CSF receptor.

The interferon family of receptors which include interferons α/β and γ (which can activate one or more members of the JAK, Tyk family of tyrosine kinases) as well as the receptors for growth hormone, erythropoietin and prolactin (which also can activate JAK2) can also be used as sources for cytoplasmic domains.

Other sources of cytoplasmic domains include the TGF-β family of cell surface receptors (reviewed by Kingsley, D., *Genes and Development* 1994 8 133). This family of receptors contains serin/threonine kinase activity in their cytoplasmic domains, which are believed to be actiated by crosslinking.

The tyrosine kinases associated with activation and inactivation of transcription factors are of particular interest in providing specific pathways which can be controlled and can be used to initiate or inhibit expression of an exogenous gene.

The following table provides a number of receptors and characteristics associated with the receptor and their nuclear response elements that activate genes. The list is not exhaustive, but provides exemplary systems for use in the subject invention.

In many situations mutated cytoplasmic domains can be obtained where the signal which is transduced may vary from the wild type, resulting in a restricted or different pathway as compared to the wild-type pathway(s). For example, in the case of growth factors, such as EGF and FGF, mutations have been reported where the signal is uncoupled from cell growth but is still maintained with c-fos (Peters, et al., *Nature* (1992) 358, 678).

The tyrosine kinase receptors can be found on a wide variety of cells throughout the body. In contrast, the CD3 ζ-family, the Ig family and the lymphokine β-chain receptor family are found primarily on hematopoietic cells, particularly T-cells, B-cells, mast cells, basophils, macrophages, neutrophils, and natural killer cells. The signals required for NF-AT transcription come primarily from the zeta (ζ) chain of the antigen receptor and to a lesser extent CD3γ, δ, ε.

The cytoplasmic domain, as it exists naturally or as it may be truncated, modified or mutated will be at least about 10, usually at least about 30 amino acids, more usually at least about 50 amino acids, and generally not more than about 400 amino acids, usually not more than about 200 amino adds. (See Romeo, et al., Cell (1992) 68, 889–893.) While any species can be employed, the species endogenous to the host cell is usually preferred. However, in many cases, the cytoplasmic domain from a different species can be used effectively. Any of the above indicated cytoplasmic domains may be used, as well as others which are presently known or may subsequently be discovered.

TABLE 1

| Ligand | DNA Element | Binding Factor(s) | Gene | Reference |
|---|---|---|---|---|
| Insulin and others | cAMP responsive element (cre) | LRFI | jun-B many genes | Mol. Cell Biol. (1992), 12, 4654, PNAS, 83, 3439 |
| PDGF, FGF, TGF and others | SRE | SRF/SR EBP | c-fos | Mol. Cell Biol. (1992), 12, 4769 |
| EGF | VL30 RSRF | | RVL-3 virus c-jun | Mol. Cell. Biol. (1992), 12, 2793 Mol. Cell. Biol. (1992), 12, 4472 |
| IFN-α | ISRE | ISGF-3 | | Gene Dev. (1989) 3,1362 |
| IFN-γ | GAS | GAF | GBP | Mol. Cell. Biol. (1991) 11, 182 |
| PMA and TCR | | AP-1 | many genes | Cell (1987) 49, 729–739 |
| TNF | | NFκB | many genes | Cell (1990) 62, 1019–1029 |
| Antigen | ARRE-1 | OAP/Oct-1 | many genes | Mol. Cell Biol. (1988) 8, 1715 |
| Antigen | ARRE-2 | NFAT | IL-2 enhancer | Science (1988) 241, 202 |

For the most part, the other chimeric proteins associated with transcription factors, will differ primarily in having a cellular targeting sequence which directs the chimeric protein to the internal side of the nuclear membrane and having transcription factors or portions thereof as the action domains. Usually, the transcription factor action domains can be divided into "DNA binding domains" and "activation domains." One can provide for a DNA binding domain with one or more ligand binding domains and an activation domain with one or more ligand binding domains. In this way the DNA binding domain can be coupled to a plurality of binding domains and/or activation domains. Otherwise, the discussion for the chimeric proteins associated with the surface membrane for signal transduction is applicable to the chimeric proteins for direct binding to genomic DNA. Similarly, the chimeric protein associated with exocytosis will differ primarily as to the proteins associated with fusion of the vesicle membrane with the surface membrane, in place of the transducing cytoplasmic proteins.

B. Cellular Targeting Domains

A signal peptide or sequence provides for transport of a chimeric protein to the cell surface membrane, where the same or other sequences can result in binding of the chimeric protein to the cell surface membrane. While there is a general motif of signal sequences, two or three N-terminal polar amino acids followed by about 15–20 primarily hydrophobic amino adds, the individual amino acids can be widely varied. Therefore, substantially any signal peptide can be employed which is functional in the host and may or may not be associated with one of the other domains of the chimeric protein. Normally, the signal peptide is processed and will not be retained in the mature chimeric protein. The sequence encoding the signal peptide is at the 5'-end of the coding sequence and will include the initiation methionine codon.

The choice of membrane retention domain is not critical to this invention, since it is found that such membrane retention domains are substantially fungible and there is no critical amino acid required for binding or bonding to another membrane region for activation. Thus, the membrane retention domain can be isolated from any convenient surface membrane or cytoplasmic protein, whether endogenous to the host cell or not.

There are at least two different membrane retention domains: a transmerbrane retention domain, which is an amino acid sequence which extends across the membrane, and a lipid membrane retention domains which lipid associates with the lipids of the cell surface membrane.

For the most part, for ease of construction, the transmembrane domain of the cytoplasmic domain or the receptor domain can be employed, which may tend to simplify the construction of the fused protein. However, for the lipid membrane retention domain, the processing signal will usually be added at the 5' end of the coding sequence for N-terminal binding to the membrane and, proximal to the 3' end for C-terminal binding. The lipid membrane retention domain will have a lipid of from about 12 to 24 carbon atoms, particularly 14 carbon atoms, more particularly myristoyl, joined to glycine. The signal sequence for the lipid binding domain is an N-terminal sequence and can be varied widely, usually having glycine at residue 2 and lysine or arginine at residue 7 (Kaplan, et al., Mol. Cell. Biol. (1988) 8, 2435). Peptide sequences involving post-translational processing to provide for lipid membrane binding are described by Carr, et al., PNAS USA (1988) 79, 6128; Aitken, et al., FEBS Lett. (1982) 150, 314; Henderson, et al., PNAS USA (1983) 80, 319; Schulz, et al., Virology (1984), 123, 2131; Deliman, et al., Nature (1985) 314, 374; and reviewed in Ann. Rev. of Biochem. (1988) 57, 69. An amino acid sequence of interest includes the sequence M-G-S-S-K-S-K-P-K-D-P-S-Q-R (SEQ ID NO: 1). Various DNA sequences can be used to encode such sequence in the fused receptor protein.

Generally, the transmembrane domain will have from about 18–30 amino acids, more usually about 20–30 amino acids, where the central portion will be primarily neutral, non-polar amino acids, and the termini of the domain will be polar amino acids, frequently charged amino acids, generally having about 1–2 charged, primarily basic amino acids at the termnini of the transmembrane domain followed by a helical break residue, e.g. pro- or gly-.

C. Ligand Binding Domain

The ligand binding ("dimerization" or "receptor") domain of any of the chimeric proteins of this invention can be any convenient domain which will allow for induction using, or bind to, a natural or unnatural ligand, preferably an unnatural synthetic ligand. The binding domain can be internal or external to the cellular membrane, depending upon the nature of the construct and the choice of ligand. A wide variety of binding proteins, including receptors, are known, including binding proteins associated with the cytoplasmic regions indicated above. Of particular interest are binding proteins for which ligands (preferably small organic ligands) are known or may be readily produced. These receptors or ligand binding domains include the FKBPs and cyclophilin receptors, the steriod receptors, the tetracycline receptor the other receptors indicated above, and the like, as well as "unnatural" receptors, which can be obtained from antibodies, particularly the heavy or light chain subunit, mutated sequences thereof, random amino acid sequences obtained by stochastic procedures, combinatorial syntheses, and the like. For the most part, the receptor domains will be at least about 50 amino acids, and fewer than about 350 amino acids, usually fewer than 200 amino acids, either as the natural domain or truncated active portion thereof. Preferably the binding domain will be small (<25 kDa, to allow efficient transfection in viral vectors), monomeric, nonimmunogenic, and should have synthetically accessible, cell permeable, nontoxic ligands that can be configured for dimerization.

The receptor domain can be intracellular or extracellular depending upon the design of the construct encoding the chimeric protein and the availability of an appropriate ligand. For hydrophobic ligands, the binding domain can be on either side of the membrane but for hydrophilic ligands, particularly protein ligands, the binding domain will usually be external to the bell membrane, unless there is a transport system for internalizing the ligand in a form in which it is available for binding. For an intracellular receptor, the construct can encode a signal peptide and transmerbane domain 5' or 3' of the receptor domain sequence or by having a lipid attachment signal sequence 5' or 3' of the receptor domain sequence. Where the receptor domain is between the signal peptide and the transmembrane domain, the receptor domain will be extracellular.

The portion of the construct encoding the receptor can be subjected to mutagenesis for a variety of reasons. The mutagenized protein can provide for higher binding affinity, allow for discrimination by the ligand of the naturally occurring receptor and the mutagenized receptor, provide opportunities to design a receptor-ligand pair, or the like. The change in the receptor can involve changes in amino acids known to be at the binding site, random mutagenesis using combinatorial techniques, where the codons for the amino acids associated with the binding site or other amino acids associated with conformational changes can be subject to mutagenesis by changing the codon(s) for the particular amino acid either with known changes or randomly, expressing the resulting proteins in an appropriate prokaryotic host and then screening the resulting proteins for binding. Illustrative of this situation is to modify FKBP12's Phe36 to Ala and/or Asp37 to Gly or Ala to accommodate a substituent at positions 9 or 10 of FK506 or FK520. In particular, mutant FKBP12 moieties which contain Val, Ala, Gly, Met or other small amino acids in place of one or more of Tyr26, Phe36, Asp37, Tyr82 and Phe99 are of particular interest as receptor domains for FK506-type and FK520-type ligands containing modifications at C9 and/or C10.

Antibody subunits, e.g. heavy or light chain, particularly fragments, more particularly all or part of the variable region, or fusions of heavy and light chain to create high-affinity binding, can be used as the binding domain. Antibodies can be prepared against haptenic molecules which are physiologically acceptable and the individual antibody subunits screened for binding affinity. The cDNA encoding the subunits can be isolated and modified by deletion of the constant region, portions of the variable region, mutagenesis of the variable region, or the like, to obtain a binding protein domain that has the appropriate affinity for the ligand this way, almost any physiologically acceptable haptenic compound can be employed as the ligand or to provide an epitope for the ligand. Instead of antibody units, natural receptors can be employed, where the binding domain is known and there is a useful ligand for binding.

The ability to employ in vitro mutagenesis or combinatorial modifications of sequences encoding proteins allows for the production of libraries of proteins which can be screened for binding affinity for different ligands. For example, one can totally randomize a sequence of 1 to 5, 10 or more codons, at one or more sites in a DNA sequence encoding a binding protein, make an expression construct and introduce the expression construct into a unicellular microorganism, and develop a library. One can then screen the library for binding affinity to one or desirably a plurality of ligands. The best affinity sequences which are compatible with the cells into which they would be introduced can then be used as the binding domain. The ligand would be screened with the host cells to be used to determine the level of binding of the ligand to endogenous proteins. A binding profile could be defined weighting the ratio of binding affinity to the mutagenized binding domain with the binding affinity to endogenous proteins. Those ligands which have the best binding profile could then be used as the ligand. Phage display techniques, as a non-limiting example, can be used in carrying out the foregoing.

D. Multimerization

The transduced signal will normally result from ligand-mediated oligomerization of the chimeric protein molecules, i.e. as a result of oligomerization following ligand binding, although other binding events, for example allosteric activation, can be employed to initiate the signal. The construct of the chimeric protein will vary as to the order of the various domains and the number of repeats of an individual domain. For the extracellular receptor domain in the 5'-3' direction of transition, the construct will encode a protein comprising the signal peptide, the receptor domain, the transmembrane domain and the signal initiation domain, which last domain will be intracellular (cytoplasmic). However, where the receptor domain is intracellular, different orders may be employed, where the signal peptide can be followed by either the receptor or signal initiation domain, followed by the remaining domain, or with a plurality of receptor domains, the signal initiation domain can be sandwiched between receptor domains. Usually, the active site of the signal initiation domain will be internal to the sequence and not require a free carboxyl terminus. Either of the domains can be multimerized, particularly the receptor domain, usually having not more than about 5 repeats, more usually not more than about 3 repeats.

For multimerizing the receptor, the ligand for the receptor domains of the chimeric surface membrane proteins will usually be multimeric in the sense that it will have at east two binding sites, with each of the binding sites capable of binding to the receptor domain. Desirably, the subject ligands will be a dimer or higher order oligomer, usually not greater than about tetrameric, of small synthetic organic molecules, the individual molecules typically being at least about 150 D and fewer than about 5 kD, usually fewer than about 3 kD. A variety of pairs of synthetic ligands and receptors can be employed. For example, in embodiments involving natural receptors, chimeric FK506 can be used with an FKBP receptor, dimerized cyclosporin A can be used with the cyclophilin receptor, dimerized estrogen with an estrogen receptor, dimerized glucocorticoids with a glucocorticoid receptor, dimerized tetracycline with the tetracycline receptor, dimerized vitamin D with the vitamin D receptor, and the like. Alternatively higher orders of the ligands, e.g. trimeric can be used. For embodiments involving unnatural receptors, e.g. antibody subunits, modified antibody subunits or modified receptors and the like, any of a large variety of compounds can be used. A significant characteristic of these ligand units is that they bind the receptor with high affinity (preferably with a $K_d \leq 10^{-8}$ M) and are able to be dimerized chemically.

The ligand can have different receptor binding molecules with different epitopes (also referred to as "HED" reagents, since they can mediate hetero-dimerization or hetero-oligomerization of chimeric proteins having the same or different binding domains. For example, the ligand may comprise FK506 or an FK506-type moiety and a CsA or a cyclosporin type moiety. Both moieties are covalently attached to a common linker moiety. Such a ligand would be useful for mediating the oligomerization of a first and second chimeric protein where the first chimeric protein contains a receptor domain such as an FKBP12 which is capable of binding to the FK506-type moiety and the second chimeric protein contains a receptor domain such as cyclophilin which is capable of binding to the cyclosporin A-type moiety.

C. Tissue Specific Expression of the Chimeric Proteins

It will be preferred in certain embodiments, that apoptosis and/or optional biological events (e.g. the expression of a target gene) be triggered in a cell-specific or tissue-specific manner. To achieve such specificity, one may render the expression of the chimeric proteins cell-type specific. Such specificity of expression may be achieved by linking one or more of the DNA sequences encoding the chimeric proteins) to a cell-type specific transcriptional regulatory sequence (e.g. promoter/enhancer). Numerous cell-type specific transcriptional regulatory sequences are known. Others may be obtained from genes which are expressed in a cell-specific manner.

For example, constructs for expressing the chimeric proteins may contain regulatory sequences derived from genes known for specific expression in selected tissues. Representative illustrative examples are tabulated below:

| Tissue | Gene | Reference |
|---|---|---|
| lens | γ2-crystallin | Breitman, M. L., Clapoff, S., Rossant, J., Tsui, L. C., Golde, L. M., Maxwell, L. H., Bernstin, A. (1987) Genetic Ablation: targeted expression of a toxin gene causes microphthalmia in transgenic mice. Science 238: 1563–1565 |
| | αA-crystallin | Landel, C. P., Zhao, J., Bok, D., Evans, G. A. (1988) Lens-specific expression of a recombinant ricin induces developmental defects in the eyes of transgenic mice. Genes Dev. 2: 1168–1178 Kaur, S., key, B., Stock, J., McNeish, J. D., Akeson, R., Potter, S. S. (1989) Targeted ablation of alpha-crystallin-synthesizing cells produces lens-deficient eyes in transgenic mice. Development 105: 613–619 |
| pituitary-somatrophic cells | Growth hormone | Behringer, R. R., Mathews, L. S., Palmiter, R. D., Brinster, R. L. (1988) Dwarf mice produced by genetic ablation of growth hormone-expressing cells. Genes Dev. 2: 453–461 |
| pancreas | Insulin-Elastase-acinar cell specific | Ornitz, D. M., Palmiter, R. D., Hammer, R. E., Brinster, R.L, Swift, G. H., MacDonald, R. J. (1985) Specific expression of an elastase-human growth fusion in pancreatic acinar cells of transgeneic mice. Nature 131: 600–603 Palmiter, R. D., Behringer, R. R., Quaife, C. J., Maxwell, F., Maxwell, I. H., Brinster, R. L. (1987) Cell lineage ablation in transgeneic mice by cell-specific expression of a toxin gene. Cell 50: 435–443 |
| T cells | lck promoter | Chaffin, K. E., Beals, C. R., Wilkie, T .M., Forbush, K. A., Simon, M.I., Perlmutter, R.M. (1990) EMBO Journal 9: 3821–3829 |
| B cells | Immunoglobulin kappa light chain | Borelli, E., Heyman, R., Hsi, M., Evans, R. M. (1988) Targeting of an inducible toxic phenotype in animal cells. Proc. Natl. Acad. Sci. USA 85: 7572–7576 Heyman, R. A., Borrelli, E., Lesley, J., Anderson, D., Richmond,, D. D., Baird, S. M., Hyman, R., Evans, R.M. (1989) Thymidine kinase obliteration: creation of transgenic mice with controlled immunodeficiencies. Proc. Natl. Acad. Sci. USA 86: 2698–2702 |
| Schwann cells | $P_0$ promoter | Messing. A., Behringer, R. R., Hammang, J. P. Palmiter, R. D., Brinster, R. L., Lemke, G. ,$P_0$ promoter directs espression of reporter and toxin genes to Schwann cells of transgenic mice. Neuron 8: 507–520 1992 |
| | Myelin basic protein | Miskimins, R. Knapp, L., Dewey, M J, Zhang, X. Cell and tissue-specific expression of a heterologous gene under control of the myelin basic protein gene promoter in trangenic mice. Brain Res Dev Brain Res 1992 Vol 65: 217–21 |
| spermatids | protamine | Breitman, M. L., Rombola, H., Maxwell, I. H., Klintworth, G.K., Bernstein, A. (1990) Genetic ablation in transgenic mice with attenuated diphtheria toxin A gene. Mol. Cell. Biol. 10: 414–479 |
| lung | Lung surfacant gene | Ornitz, D. M., Palmiter, R. D., Hammer, R. E., Brinster, R. L., Swift, G. H., MacDonald, R. J. (1985) Specific expression of an elastase-human growth fusion in pancreatic acinar cells of transgeneic mice. Nature 131: 600–603 |
| adipocyte P2 | | Ross, S. R., Braves, RA, Spiegelman, BM Targeted expression of a toxin gene to adipose tissue: transgenic mice resistant to obesity Genes and Dev 7: 1318–24 1993 |
| muscle | myosin light chain | Lee, KJ, Ross, RS, Rockman, HA, Harris, AN, O'Brien, TX, van-Bilsen, M., Shubeita, HE, Kandolf, R., Brem, G., Prices et alJ. BIol. Chem. 1992 Aug 5, 267: 15875–85 |
| | Alpha actin | Muscat, GE., Peny, S., Prentice, H. Kedes, L. The human skeletal alpha-actin gene is regulated by a muscle-specific enhancer that binds three nuclear factors. Gene Expression 2, 111–26, 1992 |
| neurons | neurofilament proteins | Reeben, M. Halmekyto, M. Alhonen, L. Sinervirta, R. Saarma, M. Janne, J. Tissue-specific expression of rat light neurofilament promoter-driven reporter gene in transgenic mice. BBRC 1993: 192: 465–70 |

-continued

| Tissue | Gene | Reference |
|---|---|---|
| liver | tyrosine aminotransferase, albumin, apolipoproteins | |

Identification of Tissue Specific Promoters

To identify the sequences that control the tissue- or cell-type specific expression of a gene, one isolates a genomic copy of the selected gene including sequences "upstream" from the exons that code for the protein.

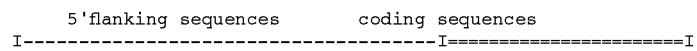

These upstream sequences are then usually fused to an easily detectable reporter gene like beta-galactosidase, in order to be able to follow the expression of the gene under the control of upstream regulatory sequences.

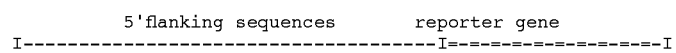

To establish which upstream sequences are necessary and sufficient to control gene expression in a cell-type specific manner, the complete upstream sequences are introduced into the cells of interest to determine whether the initial done contains the control sequences. Reporter gene expressor is monitored as evidence of expression.

If these sequences contain the necessary sequences for cell-type specific expression, deletions may be made in the 5' flanking sequences to determine which sequences are minimally required for cell-type specific expression. This can be done by making transgenic mice with each construct and monitoring beta gal expression, or by first examining the expression in specific culture cells, with comparison to expression in non-specific cultured cells.

Several successive rounds of deletion analysis normally pinpoint the minimal sequences required for tissue specific expression. Ultimately, these sequences are then introduced into transgenic mice to confirm that the expression is only detectable in the cells of interest.

VI. Cells

The cells may be procaryotic, but are preferably eucaryotic, including plant, yeast, worm, insect and mammalian. At present it is especially preferred that the cells be mammalian, particularly primate, more particularly human, but can be associated with any animal of interest, particularly domesticated animals, such as equine, bovine, murine, ovine, canine, feline, etc. Among these species, various types of cells can be involved such as hematopoietic, neural, mesenchymal, cutaneous, mucosal, stromal, muscle, spleen, reticuloendothelial, epithelial, endothelial, hepatic, kidney, gastrointestinal, pulmonary, etc. Of particular interest are hematopoietic cells, which include any of the nucleated cells which may be involved with the lymphoid or myelomonocytic lineages. Of particular interest are members of the T- and B-cell lineages, macrophages and monocytes, myoblasts and fibroblasts. Also of particular interest are stem and progenitor cells, such as hematopoietic neural, stromal, muscle, hepatic, pulmonary, gastrointestinal, etc.

The cells can be autologous cells, syngeneic cells, allogenic cells and even in some cases, xenogeneic cells. The cells may be modified by changing the major histocompatibility complex ("MHC") profile, by inactivating $\beta_2$-microglobulin to prevent the formation of functional Cass I MHC molecules, inactivation of Class II molecules, providing for expression of one or more MHC molecules, enhancing or inactivating cytotoxic capabilities by enhancing or inhibiting the expression of genes associated with the cytotoxic activity, or the like.

In some instances specific clones or oligoclonal cells may be of interest, where the cells have a particular specificity, such as T cells and B cells having a specific antigen specificity or homing target site specificity.

VII. Ligands

A wide variety of ligands, including both naturally occurring and synthetic substances, can be used in this invention to effect oligomerization of the chimeric protein molecules. Applicable and readily observable or measurable criteria for selecting a ligand are: (A) the ligand is physiologically acceptable (i.e., lacks undue toxicity towards the cell or animal for which it is to be used), (B) it has a reasonable therapeutic dosage range, (C) desirably (for applications in whole animals, including gene therapy applications), it can be taken orally (is stable in the gastrointestinal system and absorbed into the vascular system), (D) it can cross the cellular and other membranes, as necessary, and (E) binds to the receptor domain with reasonable affinity for the desired application. A first desirable criterion is that the compound is relatively physiologically inert, but for its activating capability with the receptors. The less the ligand binds to native receptors and the lower the proportion of total ligand which binds to native receptors, the better the response will normally be. Particularly, the ligand should not have a strong biological effect on native proteins. For the most part, the ligands will be non-peptide and non-nucleic acid.

The subject compounds will for the most part have two or more units, where the units can be the same or different, joined together through a central linking group. The "units" will be individual moieties (e.g., FK506, FK520, cyclosporin A, a steroid, etc.) capable of binding the receptor domain. Each of the units will usually be joined to the linking group through the same reactive moieties, at least in homodimers or higher order homo-oligomers.

As indicated above, there are a variety of naturally-occurring receptors for small non-proteinaceous organic molecules, which small organic molecules fulfill the above criteria, and can be dimerized at various sites to provide a ligand according to the subject invention. Substantial modifications of these compounds are permitted so long as the binding capability is retained and with the desired specificity. Many of the compounds will be macrocyclics, e.g. macrolides. Suitable binding affinities will be reflected in Kd values well below $10^{-4}$, preferably below $10^{-6}$, more preferably below about $10^{-7}$, although binding affinities below $10^{-9}$ or $10^{-10}$ are possible, and in some cases will be most desirable.

Currently preferred ligands comprise oligomers, usually dimers, of compounds capable of binding to an FKBP protein and/or to a cyclophilin protein. Such ligands includes homo- and heteromultimers (usually 2–4, more usually 2–3 units) of cyclosporin A, FK506, FK520, and rapamycin, and derivatives thereof, which retain their binding capability to the natural or mutagenized binding domain. Many derivatives of such compounds are already known, including synthetic high affinity FKBP ligands, which can be used in the practice of this invention. See e.g. Holt et al, J Am Chem Soc 1993, 115, 9925–9935. Sites of interest for linking of FK506 and analogs thereof include positions involving annular carbon atoms from about 17 to 24 and substituent positions bound to those annular atoms, e.g. 21 (allyl), 22, 37, 38, 39 and 40, or 32 (cyclohexyl), while the same positions except for 21 are of interest for FK520. For cyclosporin, sites of interest include MeBmt, position 3 and position 8.

Of particular interest are modifications to the ligand which change its binding characteristics, particularly with respect to the ligand's naturally occurring receptor. Concomitantly, one would change the binding protein to accommodate the change in the ligand. For example one can modify the groups at position 9 or 10 of FK506(see Van Duyne et al (1991) *Science* 252, 839), so as to increase their steric requirement, by replacing the hydroxyl with a group having greater steric requirements, or by modifying the carbonyl at position 10, replacing the carbonyl with a group having greater steric requirements or functionalizing the carbonyl, e.g. forming an N-substituted Schiff's base or imine, to enhance the bulk at that position. Various functionalities which can be conveniently introduced at those sites are all groups to form ethers, acylamido groups, N-alkylated amines, where a 2-hydroxyethylimine can also form a 1,3-oxazoline, or the like. Generally, the substituents will be from about 1 to 6, usually 1 to 4, and more usually 1 to 3 carbon atoms, with from 1 to 3, usually 1 to 2 heteroatoms, which will usually be oxygen, sulfur, nitrogen, or the like. By using different derivatives of the basic structure, one can create different ligands with different conformational requirements for binding. By mutagenizing receptors, one can have different receptors of substantially the same sequence having different affinities for modified ligands not differing significantly in structure.

Other ligands which can be used are steroids. The steroids can be oligomerized, so that their natural biological activity is substantially diminished without loss of their binding capability with respect to a chimeric protein containing one or more steroid receptor domains. By way of non-limiting example, glucocorticoids and estrogens can be so used. Various drugs can also be used, where the drug is known to bind to a particular receptor with high affinity. This is particularly so where the binding domain of the receptor is known, thus permitting the use in chimeric proteins of this invention of only the binding domain, rather than the entire native receptor protein. For this purpose, enzymes and enzyme inhibitors can be used.

A. Linkers

Various functionalities can be involved in the linking, such as amide groups, including carbonic add derivatives, ethers, esters, including organic and inorganic esters, amino, or the like. To provide for linking, the particular monomer can be modified by oxidation, hydroxylation, substitution, reduction, etc., to provide a site for coupling. Depending on the monomer, various sites can be selected as the site of coupling.

The multimeric ligands can be synthesized by any convenient means, where the linking group will be at a site which does not interfere with the binding of the binding site of a ligand to the receptor. Where the active site for physiological activity and binding site of a ligand to the receptor domain are different, it will usually be desirable to link at the active site to inactivate the ligand. Various linking groups can be employed, usually of from 1–30, more usually from about 1–20 atoms in the chain between the two molecules (other than hydrogen), where the linking groups will be primarily composed of carbon, hydrogen, nitrogen, oxygen, sulphur and phosphorous. The linking groups can involve a wide variety of functionalities, such as amides and esters, both organic and inorganic, amines, ethers, thioters, disulfides, quaternary ammonium salts, hydrazines, etc. The chain can include alphatic, alicyclic, aromatic or heterocyclic groups. The chain will be selected based on ease of synthesis and the stability of the multimeric ligand. Thus, if one wishes to maintain long-term activity, a relatively inert chain will be used, so that the multimeric ligand link will not be cleaved. Alternatively, if one wishes only a short half-life in the blood stream, then various groups can be employed which are readily cleaved, such as esters and amides, particularly peptides, where circulating and/or intracellular proteases can cleave the linking group.

Various groups can be employed as the lining group between ligands, such as alkylene, usually of from 2 to 20 carbon atoms, azalkylene (where the nitrogen will usually be between two carbon atoms), usually of from 4 to 18 carbon atoms), N-alkylene azalkylene (see above), usually of from 6 to 24 carbon atoms, arylene, usually of from 6 to 18 carbon atoms, ardialkylene, usually of from 8 to 24 carbon atoms, bis-carboxamido alkylene of from about 8 to 36 carbon atoms, etc. Illustrative groups include decylene, octadecylene, 3-azapentylene, 5-azadecylene, N-butylene 5-azanonylene, phenylene, xylylene, p-dipropylenebenzene, bis-benzoyl 1,8-diaminooctane and the like. Multivalent or other (see below) ligand molecules containing linker moieties as described above can be evaluated with chimeric proteins of this invention bearing corresponding receptor domains using materials and methods described in the examples which follow.

B. Ligand Characteristics

For intracellular binding domains, the ligand will be selected to be able to be transferred across the membrane in a bioactive forms that is, it will be membrane permeable. Various ligands are hydrophobic or can be made so by appropriate modification with lipophilic groups. Particularly, the linking bridge can serve to enhance the lipophilicity of the ligand by providing aliphatic side chains of from about 12 to 24 carbon atoms. Alternatively, one or more groups can be provided which will enhance transport across the membrane, desirably without endosome formation.

In some instances, multimeric ligands need not be employed. For example, molecules can be employed where two different binding sites provide for dimerization of the receptor. In other instances, binding of the ligand can result in a conformational change of the receptor domain, resulting in activation, e.g. oligomerization, of the receptor. Other mechanisms may also be operative for inducing the signal, such as binding a single receptor with a change in conformation resulting in activation of the cytoplasmic domain.

As discussed elsewhere, ligands capable of initiating any of the optional additional cellular processes, such as transcription of a target gene, should preferably be selected so as not to cross react with the primary chimeric proteins in the engineered cells to initiate apoptosis.

C. Ligand Antagonists

Monomeric ligands can be used for reversing the effect of the multimeric ligand, i.e., for preventing, inhibiting or disrupting oligomer formation or maintenance. Thus, if one wishes to rapidly terminate the effect of cellular activation, a monomeric ligand can be used. Conveniently, the parent ligand moiety on be modified at the same site as the multimer using the same procedure, except substituting a monofunctional compound for the polyfunctional compound. Instead of the polyamines, monoamines, particularly of from 2 to 20 (although they can be longer), and usually 2 to 12, carbon atoms can be used, such as ethylamine, hexylamine, benzylamine, etc. Alternatively, the monovalent parent compound can be used, in cases (or at dosage levels) in which the parent compound does not have undue undesirable physiological activity (e.g. immunosuppression, mitogenesis, toxicity, etc.)

D. Illustrative Hetero-Oligomerizing (HED) and Homo-Oligomerizing (HOD) Reagents with "Bumps" that can Bind to Mutant Receptors Containing Compensatory Mutations As discussed above, one can prepare modified HED/HOD reagents that will fail to bind appreciably to their wild type receptors (e.g., FKBP12) due to the presence of substituents ("bumps") on the reagents that sterically clash with sidechain residues in the receptor's binding pocket. One may also make corresponding receptors that contain mutations at the interfering residues ("compensatory mutations") and therefore gain the ability to bind ligands with bumps. Using "bumped" ligand moieties and receptor domains bearing "compensatory mutations" should enhance the specificity and thus the potency of our reagents. Bumped reagents should not bind to the endogenous, wild type receptors, which can otherwise act as a "buffer" toward dimerizers based on natural ligand moieties. In addition, the generation of novel receptor-ligand pairs should simultaneously yield the HED reagents that will be used when heterodimerization is required. For example, regulated vesicle fusion may be achieved by inducing the heterodimerization of syntaxin (a plasma membrane fusion protein) and synaptobrevin (a vesicle membrane fusion protein) using a HED reagent. This would not only provide a research tool, but could also serve as the basis of a gene therapy treatment for diabetes, using appropriately modified secretory cells.

As an illustration of "Bumped FK1012s" we prepared C10 acetamide and formamide derivatives of FK506. See FIG. 16 and our report, Spencer et al, "Controlling Signal Transduction with Synthetic Ligands," Science 262(1993): 1019–1024 for additional details concerning the syntheses of FK1012s A–C and FK506M. We chose to create two classes of bumped K1012s: one with a bump at C10 and one at C9. The R- and S-isomers of the C10 acetamide and formamide of FK506 have been synthesized according to the reaction sequence in FIG. 16B. These bumped derivatives have lost at least three orders of magnitude in their binding affinity towards FKBP12 (FIG. 16B). The affinities were determined by measuring the ability of the derivatives to inhibit FKBP12's rotamase activity.

An illustrative member of a second class of C9-bumped derivatives is the spiro-epoxide (depicted in FIG. 16C), which has been prepared by adaptation of known procedures. See e.g. Fisher et al, *J Org Chem* 56 8(1991): 2900–7 and Edmunds et al, *Tet Lett* 32 48 (1991):819–820. A particularly interesting series of C9 derivatives are characterized by their $sp^3$ hybridization and reduced oxidation state at C9. Several such compounds have been synthesized according to the reactions shown in FIG. 16C.

It should be appreciated that heterodimers (and other hetero-oligomerizers) must be constructed differently than the homodimers, at least for applications where homodimer contamination could adversely affect their successful use. One illustrative synthetic strategy developed to overcome this problem is outlined in FIG. 16D. Coupling of mono alloc-protected 1,6-hexanediamine (Stahl et al, *J Org Chem* 43 11 (1978): 2285–6) with a derivatized form of FK506 in methylene chloride with an excess of triethylamine gave an alloc-amine-substituted FK506 in 44% yield. This intermediate can now be used in the coupling with any activated FK506 (or bumped-FK506) molecule. Deprotection with catalytic tetrakis-triphenylphosphine palladium in the presence of dimedone at room temperature in THF removes the amine protecting group. Immediate treatment with an activated FK506 derivative, followed by desilylation leads to a chimeric product. This technique has been used to synthesize the illustrated HOD and HED reagents.

E. Illustrative Cyclosporin-Based Reagents

Figure 17:
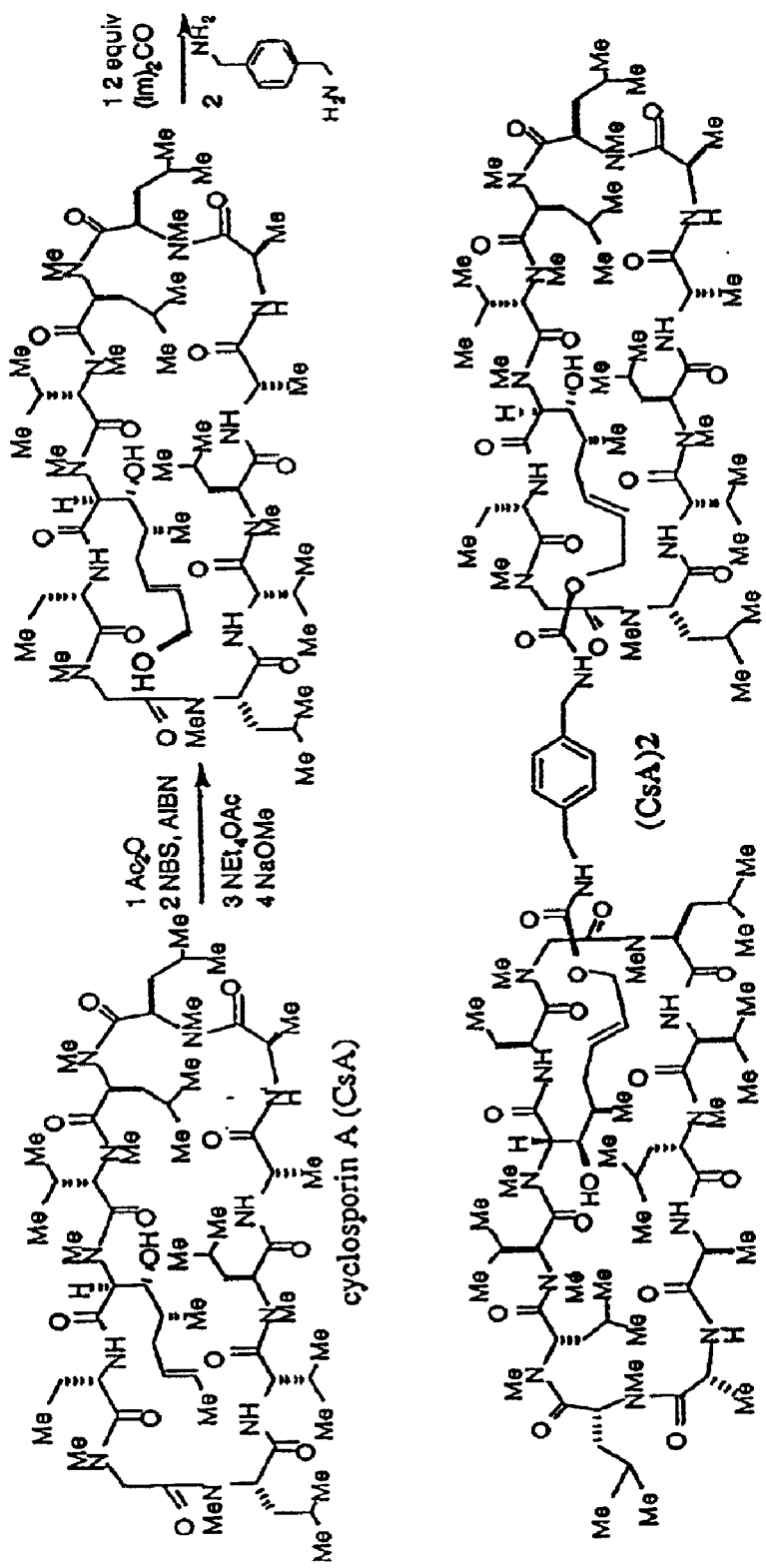
FIG. 17 depicts the synthesis of (CsA)2 beginning with CsA.

Cyclosporin A (CsA) is a cyclic undecapeptide that binds with high affinity (6 nM) to its intracellular receptor cyclophilin, an 18 kDa monomeric protein. The resulting complex, like the FKBP12-FK506 complex, binds to and inactivates the protein phosphatase calcineurin resulting in the immunosuppressive properties of the drug. As a further illustration of this invention, we have dimerized CsA via its MeBmt1 sidechain in 6 steps and 35% overall yield to give (CsA)2 (FIG. 17, steps 1–4 were conducted as reported in Eberle et al, *J Org Chem* 57 9 (1992): 2689–91). As with FK1012s, the site for dimerization was chosen such that the resulting dimer can bind to two molecules of cyclophilin yet cannot bind to calcineurin following cyclophilin binding.

We have demonstrated that (CsA)2 binds to cyclophilin A with 1:2 stoichiometry. Hence, (CsA)2, like FK1012s, does not inhibit signaling pathways and is thus neither immunosuppressive nor toxic at concentrations useful for practicing this invention.

VIII. Target Gene

A. Transcription Initiation Region

Target gene constructs will have a responsive element in the 5' region, which responds to ligand-mediated oligomerization of the chimeric receptor protein, presumably via the generation and transduction of a transcription initiation signal as discussed infra. Therefore, it will be necessary to select at least one transcription initiation system, e.g. transcription factor, which is activated either directly or indirectly, by the cytoplasmic domain or can be activated by association of two domains. It will also be necessary to select at least one promoter region which is responsive to the resulting transcription initiation system. Either the promoter region or the gene under its transcriptional control need be selected. In other words, an action domain can be selected for the chimeric proteins (encoded by a firsts series construct) based on the role of that action domain in initiating transcription via a given promoter or responsive element. See e.g. Section V(A) "Cytoplasmic domains", above.

Where the responsive element is known, it can be included in the target gene construct to provide an expression cassette for integration into the genome (whether episomally or by chromosomal incorporation). It is not necessary to have isolated the particular sequence of the responsive element, so long as a gene is known which is transcriptionally activated by the cytoplasmic domain upon natural ligand binding to the protein comprising the cytoplasmic domain. Homologous recombination could then be used for insertion of the gene of interest downstream from the promoter region to be under the transcriptional regulation of the endogenous promoter region. Where the specific responsive element sequence is known, that can be used in conjunction with a different transcription initiation region, which can have other aspects such as a high or low activity as to the rate of transcription, binding of particular transcription factors and the like.

The expression construct will therefore have at its 5' end in the direction of transcription, the responsive element and the promoter sequence which allows for induced transcription initiation of a target gene of interest, usually a therapeutic gene. The transcriptional termination region is not as important, and can be used to enhance the lifetime of or make short half-lived mRNA by inserting AU sequences which serve to reduce the stability of the mRNA and, therefore, limit the period of action of the protein. Any region can be employed which provides for the necessary transcriptional termination, and as appropriate, translational termination.

The responsive element can be a single sequence or can be oligomerized, usually having not more than about 5 repeats, usually having about 3 repeats.

Homologous recombination can also be used to remove or inactivate endogenous transcriptional control sequences, including promoter and/or responsive elements, which are responsive to the oligomerization event, and/or to insert such responsive transcriptional control sequences upstream of a desired endogenous gene.

B. Product

A wide variety of genes can be employed as the target gene, including genes that encode a protein of interest or an antisense sequence of interest or a ribozyme of interest. The target gene can be any sequence of interest which provides a desired phenotype. The target gene can express a surface membrane protein a secreted protein, a cytoplasmic protein, or there can be a plurality of target genes which can express different types of products. The target gene may be an antisense sequence which can modulate a particular pathway by inhibiting a transcriptional regulation protein or turn on a particular pathway by inhibiting the translation of an inhibitor of the pathway. The target gene can encode a ribozyme which may modulate a particular pathway by interfering, at the RNA level, with the expression of a relevant transcriptional regulator or with the expression of an inhibitor of a particular pathway. The proteins which are expressed, singly or in combination can involve homing, cytotoxicity, proliferation, immune response, inflammatory response, clotting or dissolving of clots, hormonal regulation, or the like. The proteins expressed could be naturally-occurring, mutants of naturally-occurring proteins, unique sequences, or combinations thereof.

The gene can be any gene which is secreted by a so that the encoded product can be made available at will, whenever desired or needed by the host. Various secreted products include hormones, such as insulin, human growth hormone, glucagon, pituitary releasing factor, ACTH, melanotropin, relaxin, etc.; growth factors, such as EGF, IGF-1, TGF-$\alpha$, -$\beta$, PDGF, G-CSF, M-CSF, GM-CSF, FGF, erythropoietin, megakaryocytic stimulating and growth factors, etc.; interleukins, such as IL-1 to -13; TNF-$\alpha$ and -$\beta$, etc.; and enzymes, such as tissue plasminogen activator, members of the complement cascade, perforins, superoxide dismutase, coagulation factors, antithrombin-III, Factor VIIc, Factor VIIIvW, $\alpha$-anti-trypsin, protein C, protein S, endorphins, dynorphin, bone morphogenetic protein, CFTR, etc.

The gene can be any gene which is naturally a surface membrane protein or made so by introducing an appropriate signal peptide and transmembrane sequence. Various proteins include homing receptors, e.g. L-selectin (Mel-14), blood-related proteins, particularly having a kringle structure, e.g. Factor VIIIc, Factor VIIIvW, hematopoietic cell markers, e.g. CD3, CD4, CD8, B cell receptor, TCR subunits $\alpha$, $\beta$, $\gamma$, $\delta$, CD10, CD19, CD28, CD33, CD38, CD41, etc., receptors, such as the interleukin receptors IL-2R, IL-4R, etc., channel proteins, for influx or efflux of ions, e.g. $H^+$, $Ca^{+2}$, $K^+$, $Na^+$, $Cl^-$, etc., and the like; CFTR, tyrosine activation motif, $\zeta$ activation protein, etc.

Proteins may be modified for transport to a vesicle for exocytosis. By adding the sequence from a protein which is directed to vesicles, where the sequence is modified proximal to one or the other terminus, or situated in an analogous position to the protein source, the modified protein will be directed to the Golgi apparatus for packaging in a vesicle. This process in conjunction with the presence of the chimeric proteins for exocytosis allows for rapid transfer of the proteins to the extracellular medium and a relatively high localized concentration.

Also, intracellular proteins can be of interest, such as proteins in metabolic pathways, regulatory proteins, steroid receptors, transcription factors, etc., particularly depending upon the nature of the host cell. Some of the proteins indicated above can also serve as intracellular proteins.

The following are a few illustrations of different genes. In T-cells, one may wish to introduce genes encoding one or both chains of a T-cell receptor. For B-cells, one could provide the heavy and light chains for an immunoglobulin for secretion. For cutaneous cells, e.g. keratinocytes, particularly stem cells keratinocytes, one could provide for infectious protection by secreting $\alpha$-, $\beta$- or -$\gamma$ interferon, antichemotactic factors, proteases specific for bacterial cell wall proteins, etc.

In addition to providing for expression of a gene having therapeutic value, there will be many situations where one may wish to direct a cell to a particular site. The site can include anatomical sites, such as lymph nodes, mucosal tissue, skin, synovium, lung or other internal organs or functional sites, such as clots, injured sites, sites of surgical manipulation, inflammation, infection, etc. By providing for expression of surface membrane proteins which will direct the host cell to the particular site by providing for binding at the host target site to a naturally-occurring epitope, localized concentrations of a secreted product can be achieved. Proteins of interest include homing receptors, e.g. L-selectin, GMP140, CLAM-1, etc., or addressins, e.g. ELAM-1, PNAd, LNAd, etc., clot binding proteins, or cell surface proteins that respond to localized gradients of chemotactic factors. There are numerous situations where one would wish to direct cells to a particular site, where release of a therapeutic product could be of great value.

In many situations one may wish to be able to kill the modified cells, e.g. where one wishes to terminate treatment with the cells, where the cells have become undesirable e.g. neoplastic, or where the purpose served by the cells has already been served and their continued presence is undesirable. Modified cells of this invention, which are capable of expressing a primary chimeric protein containing a domain such as the cytoplasmic domain of the Fas antigen or TNF receptor (Watanable-Fukunaga et al. Nature (1992) 356, 314–317), are readily eliminated through apoptosis following exposure of the cells to a ligand capable of oligomerizing the primary chimeras. Constructs encoding the primary chimera may be designed for constitutive expression using conventional materials and methods, so that the modified cells have such proteins on their surface or present in their cytoplasm. Alternatively, one can provide for controlled expression, where the same or different oligomerizing ligand can initiate expression of the primary chimera and initiate apoptosis. By providing for the cytoplasmic portions of the Fas antigen or TNF receptor in the cytoplasm joined to binding regions different from the binding regions associated with expression of a target gene of interest, one can kill the modified cells under controlled conditions.

C. Illustrative Exemplifications

By way of illustration, cardiac patients or patients susceptible to stroke may be treated as follows. Cells modified as described herein may be administered to the patient and retained for extended periods of time. Illustrative cells include plasma cells, B-cells, T-cells, or other hematopoietic cells. The cell would be modified to express a protein which binds to a blood clot, e.g. having a kringle domain structure or an adhesive interactive protein, e.g. CD41, and to express a clot dissolving protein e.g. tissue plasminogen activator, streptokinase, etc. In this way, upon ligand-mediated oligomerization, the cells would accumulate at the site of the dot and provide for a high localized concentration of the thrombolytic protein.

Another example is reperfusion injury. Cells of limited lifetime could be employed, e.g. macrophages or polymorphonuclear leukocytes ("neutrophils"). The cells would have a neutrophil homing receptor to direct the cells to a site of reperfusion injury. The cell would also express superoxide dismutase, to destroy singlet oxygen and inhibit radical attack on the tissue.

A third example is autoimmune disease. Cells of extended lifetime, e.g. T cells could be employed. The constructs would provide for a homing receptor for homing to the site of autoimmune injury and for cytotoxic attack on cells causing the injury. The therapy would then be directed against cells causing the injury. Alternatively, one could provide for secretion of soluble receptors or other peptide or protein, where the secretion product would inhibit activation of the injury causing cells or induce anergy. Another alternative would be to secrete an antiinflammatory product, which could serve to diminish the degenerative effects.

A fourth example involves treatment of chronic pain with endorphin via encapsulation. A stock of human fibroblasts is transfected with a construct in which the chimeric transcriptional regulatory protein controls the transcription of human endorphin. The DNA construct consists of three copies of the binding site for the HNF-1* transcription factor GTTAAGTTAAC (SEQ ID NO: 2), upstream of a TATAAA site and a transcriptional initiation site. The endorphin cDNA would be inserted downstream of the initiation site and upstream of a polyadenylation and termination sequences. Optionally, the endorphin cDNA is outfitted with "PEST" sequences to make the protein unstable or AUUA sequences in the 3' nontranslated region of the mRNA to allow it to be degraded quickly.

The fibroblasts are also transfected with a construct having two transition units, one of which would encode the HNF-1* cDNA truncated to encode lust the DNA binding sequences from amino acids 1 to 250 coupled to a trimeric FKBP binding domain under the transcriptional and translational control of regulatory initiation and termination regions functional in the fibroblasts. The construct would include an additional transcription unit driven by the same regulatory regions directing the production of a transitional activation domain derived from HNF-4 coupled to trimeric FKBP'. (The prime intends an altered FKBP that binds at nM concentration to a modified FK506. The modification inhibits binding to the endogenous FKBP.)

These genetically modified cells would be encapsulated to inhibit immune recognition and placed under the patient's skin or other convenient internal site. When the patient requires pain medication, the patient administers a dimeric ligand FK506-FK506', where about 1 $\mu$g to 1 mg would suffice. In this manner one could provide pain relief without injections or the danger of addiction.

A fifth example is the treatment of osteoporosis. Lymphocytes can be clonally developed or skin fibroblasts grown in culture from the patient to be treated. The cells would be transfected as described above, where a bone morphogenic factor cDNA gene would replace the endorphin gene. For lymphocytes, antigen specific clones could be used which would allow their destruction with antibodies to the idiotype of the sIg. In addition, administration of the antigen for the sIg would expand the cell population to increase the amount of the protein which could be delivered. The lymphocyte clones would be infused and the ligand administered as required for production of the bone morphogenic factor. By monitoring the response to the ligand, one could adjust the amount of bone morphogenic factor which is produced, so as to adjust the dosage to the required level.

Another situation is to modify antigen specific T cells, where one can activate expression of a protein product to activate the cells. The T cell receptor could be directed against tumor cells, pathogens, cells mediating autoimmunity, and the like. By providing for activation of the cells, for example, an interleukin such as IL-2, one could provide for expansion of the modified T cells in response to a ligand. Other uses of the modified T cells would include expression of homing receptors for directing the T cells to specific sites, where cytotoxicity, upregulation of a surface membrane protein of target cells, e.g. endothelial cells, or other biological event would be desired.

Alternatively one may want to deliver high doses of cytotoxic factors to the target site. For example, upon recognition of tumor antigens via a homing receptor, tumor-infiltrating lymphocytes (TILs) may be triggered to deliver toxic concentrations of TNF or other similar product.

Another alternative is to export hormones or factors which are exocytosed. By providing for enhanced exocytosis, a greater amount of the hormone or factor will be exported; in addition, if there is a feedback mechanism based on the amount of the hormone or factor in the cytoplasm, increased production of the hormone or factor will result. Or, one may provide for induced expression of the hormone or factor, so that expression and export may be induced concomitantly.

One may also provide for proteins in retained body fluids, e.g. vascular system, lymph system, cerebrospinal fluid, etc. By modifying cells which can have an extended lifetime in the host, e.g. hematopoietic cells, keratinocytes, muscle cells, etc. particularly, stem cells, the proteins can be maintained in the fluids for extended periods of time. The cells may be modified with constructs which provide for secretion or endocytosis. The constructs for secretion would have as the translocation domain, a signal peptide, and then as in the case of the other chimeric proteins, a binding domain and an action domain. The action domains may be derived from the same or different proteins. For example, with tissue plasminogen activator, one could have the clot binding region as one action domain and the plasminogen active site as a different action domain. Alternatively, one could provide enhanced blockage of homing, by having a binding protein, such as LFA-1 as one action domain and a selection as a second action domain. By modifying subunits of proteins, e.g. integrins, T-cell receptor, sIg, or the like, one could provide soluble forms of surface membrane proteins which could be brought together to bind to a molecule. Other opportunities are complement proteins, platelet membrane proteins involved in clotting, autoantigens on the surface of cells, and pathogenic molecules on the surface of infectious agents.

IX. Introduction of Constructs into Cells

The constructs described herein can be introduced as one or more DNA molecules or constructs, where there will usually be at least one marker and there may be two or more markers, which will allow for selection of host cells which contain the construct(s). The constructs can be prepared in conventional ways, where the genes and regulatory regions may be isolated, as appropriate, ligated, cloned in an appropriate cloning host, analyzed by restriction or sequencing, or other convenient means. Particularly, using PCR, individual fragments including all or portions of a functional unit may be isolated, where one or more mutations may be introduced using "primer repair", ligation, in vitro mutagenesis, etc. as appropriate. The construct(s) once completed and demonstrated to have the appropriate sequences may then be introduced into the host cell by any convenient means. The constructs may be integrated and packaged into non-replicating, defective viral genomes like Adenovirus, Adeno-associated virus (AAV), or Herpes simplex virus (HSV) or others, including retroviral vectors, for infection or transduction into cells. The constructs may include viral sequences for transfection, if desired. Alternatively, the construct may be introduced by fusion, electroporation, biolistics, transfection, lipofection, or the like. The host cells will usually be grown and expanded in culture before introduction of the construct(s), followed by the appropriate treatment for introduction of the construct(s) and integration of the construct(s). The cells will then be expanded and screened by virtue of a marker present in the construct. Various markers which may be used successfully include hprt, neomycin resistance, thyridine kinase, hygromycin resistance, etc.

In some instances, one may have a target site for homologous recombination, where it is desired that a construct be integrated at a particular locus. For example, can eliminate an endogenous gene and replace it (at the same locus or elsewhere) with the gene encoded for by the construct using materials and methods as are known in the art for homologous recombination. Alternatively, instead of providing a gene, one may modify the transcriptional initiation region of an endogenous gene to be responsive to the signal initiating domain. In such embodiments, transcription of an endogenous gene such as EPO, tPA, SOD, or the like, would be controlled by administration of the ligand. For homologous recombination one may use either Ω or O-vectors. See, for example, Thomas and Capecchi, *Cell* (1987) 51, 503–512; Mansour, et al., *Nature* (1988) 336, 348–352; and Joyner, et al., *Nature* (1989) 338, 153–156.

The constructs may be introduced as a single DNA molecule encoding all of the genes, or different DNA molecules having one or more genes. The constructs may be introduced simultaneously or consecutively, each with the same or different markers. In an illustrative example, one construct would contain a therapeutic gene under the control of a specific responsive element (e.g. NFAT), another encoding the receptor fusion protein comprising the signaling region fused to the ligand receptor domain (e.g. as in MZF3E). A third DNA molecule encoding a homing receptor or other product that increases the efficiency of delivery of the therapeutic product may also be introduced.

Vectors containing useful elements such as bacterial or yeast origins of replication, selectable and/or amplifiable markers, promoter/enhancer elements for expression in procaryotes or eucaryotes, etc. which may be used to prepare stocks of construct DNAs and for carrying out transfections are well known in the art, and many are commercially available.

X. Administration of Cells and Ligands

The cells which have been modified with the DNA constructs are then grown in culture under selective conditions and cells which are selected as having the construct may then be expanded and further analyzed, using, for example, the polymerase chain reaction for determining the presence of the construct in the host cells. Once the modified host cells have been identified, they may then be used as planned, e.g. grown in culture or introduced into a host organism.

Depending upon the nature of the cells, the cells may be introduced into a host organism, e.g. a mammal, in a wide variety of ways. Hematopoietic cells may be administered by injection into the vascular system, there being usually at least about $10^4$ cells and generally not more than about $10^{10}$, more usually not more than about $10^8$ cells. The number of cells which are employed will depend upon a number of circumstances, the purpose for the introduction, the lifetime of the cells, the protocol to be used, for example, the number of administrations, the ability of the cells to multiply, the stability of the therapeutic agent, the physiologic need for the therapeutic agent, and the like. Alternatively, with skin cells which may be used as a graft, the number of cells would depend upon the size of the layer to be applied to the burn or other lesion. Generally, for myoblasts or fibroblasts, the number of cells will be at least about $10^4$ and not more than about $10^8$ and may be applied as a dispersion, generally being injected at or near the site of interest. The cells will usually be in a physiologically-acceptable medium.

Instead of ex vivo modification of the cells, in many situations one may wish to modify cells in vivo. For this purpose, various techniques have been developed for modification of target tissue and cells in vivo. A number of virus vectors have been developed, such as adenovirus and retroviruses, which allow for transfection and random integration of the virus into the host. See, for example, Dubensky et al. (1984) Proc. Natl. Acad. Sci. USA 81, 7529–7533; Kaneda et al., (1989) Science 243, 375–378; Hiebert et al. (1989) Proc. Natl. Acad. Sci. USA 86, 3594–3598; Hatzoglu et al. (1990) J. Biol. Chem. 265, 17285–17293 and Ferry, et al. (1991) Proc. Natl. Acad. Sci. USA 88, 8377–8381. The vector may be administered by injection, e.g. intravascularly or intramuscularly, inhalation, or other parenteral mode.

In accordance with in vivo genetic modification, the manner of the modification will depend on the nature of the tissue, the efficiency of cellular modification required, the number of opportunities to modify the particular cells, the accessibility of the tissue to the DNA composition to be introduced, and the like. By employing an attenuated or modified retrovirus carrying a target transcriptional initiation region it desired, one can activate the virus using one of the subject transcription factor constructs, so that the virus may be produced and transfect adjacent cells.

The DNA introduction need not result in integration in every case. In some situations, transient maintenance of the DNA introduced may be sufficient. In this way, one could have a short term effect, where cells could be introduced into the host and then turned on after a predetermined time, for example, after the cells have been able to home to a particular site.

The ligand providing for activation of the cytoplasmic domain may then be administered as desired. Depending upon the binding affinity of the ligand, the response desired, the manner of administration, the half-life, the number of cells present, various protocols may be employed. The ligand may be administered parenterally or orally. The number of administrations will depend upon the factors described above. The ligand may be taken orally as a pill, powder, or dispersion; bucally, sublingually, injected intravascularly, intraperitoneally, subcutaneously; by inhalation or the like. The ligand (and monomeric compound) may be formulated using conventional methods and materials well known in the art for the various routes of administration. The precise close and particular method of administration will depend upon the above factors and be determined by the attending physician or human or animal healthcare provider. For the most part, the manner of administration will be determined empirically.

In the event that the activation by the ligand is to be reversed, the monomeric compound may be administered or other single binding site compound which can compete with the ligand. Thus, in the case of an adverse reaction or the desire to terminate the therapeutic effect, the monomeric binding compound can be administered in any convenient way, particularly intravascularly, if a rapid reversal is desired. Alternatively, one may provide for the presence of an inactivation domain (or transcriptional silencer) with a DNA binding domain. In another approach, cells may be eliminated through apoptosis via signalling through Fas or TNF receptor as described elsewhere.

The particular dosage of the ligand for any application may be determined in accordance with the procedures used for therapeutic dosage monitoring, where maintenance of a particular level of expression is desired over an extended period of times, for example, greater than about two weeks, or where there is repetitive therapy, with individual or repeated doses of ligand over short periods of time, with extended intervals, for example, two weeks or more. A dose of the ligand within a predetermined range would be given and monitored for response, so as to obtain a time-expression level relationship, as well as observing therapeutic response. Depending on the levels observed during the time period and the therapeutic response, one could provide a larger or smaller dose the next time, following the response. This process would be iteratively repeated until one obtained a dosage within the therapeutic range. Where the ligand is chronically administered, once the maintenance dosage of the ligand is determined, one could then do assays at extended intervals to be assured that the cellular system is providing the appropriate response and level of the expression product.

It should be appreciated that the system is subject to many variables, such as the cellular response to the ligand, the efficiency of expression and, as appropriate, the level of secretion, the activity of the expression product, the particular need of the patient, which may vary with time and circumstances, the rate of loss of the cellular activity as a result of loss of cells or expression activity of individual cells, and the like. Therefore, it is expected that for each individual patient, even if there were universal cells which could be administered to the population at large, each patient would be monitored for the proper dosage for the individual.

The subject methodology and compositions may be used for the treatment of a wide variety of conditions and indications. For example, B- and T-cells may be used in the treatment of cancer, infectious diseases, metabolic deficiencies, cardiovascular disease, hereditary coagulation deficiencies, autoimmune diseases, joint degenerative diseases, e.g. arthritis, pulmonary disease, kidney disease, endocrine abnormalities, etc. Various cells involved with structure, such as fibroblasts and myoblasts, may be used in the treatment of genetic deficiencies, such as connective tissue deficiencies, arthritis, hepatic disease, etc. Hepatocytes could be used in cases where large amounts of a protein must be made to complement a deficiency or to deliver a therapeutic product to the liver or portal circulation.

The following examples are offered by way illustration and not by way limitation.

EXAMPLES

Cellular Transformations and Evaluation

Example 1

Figure 1:
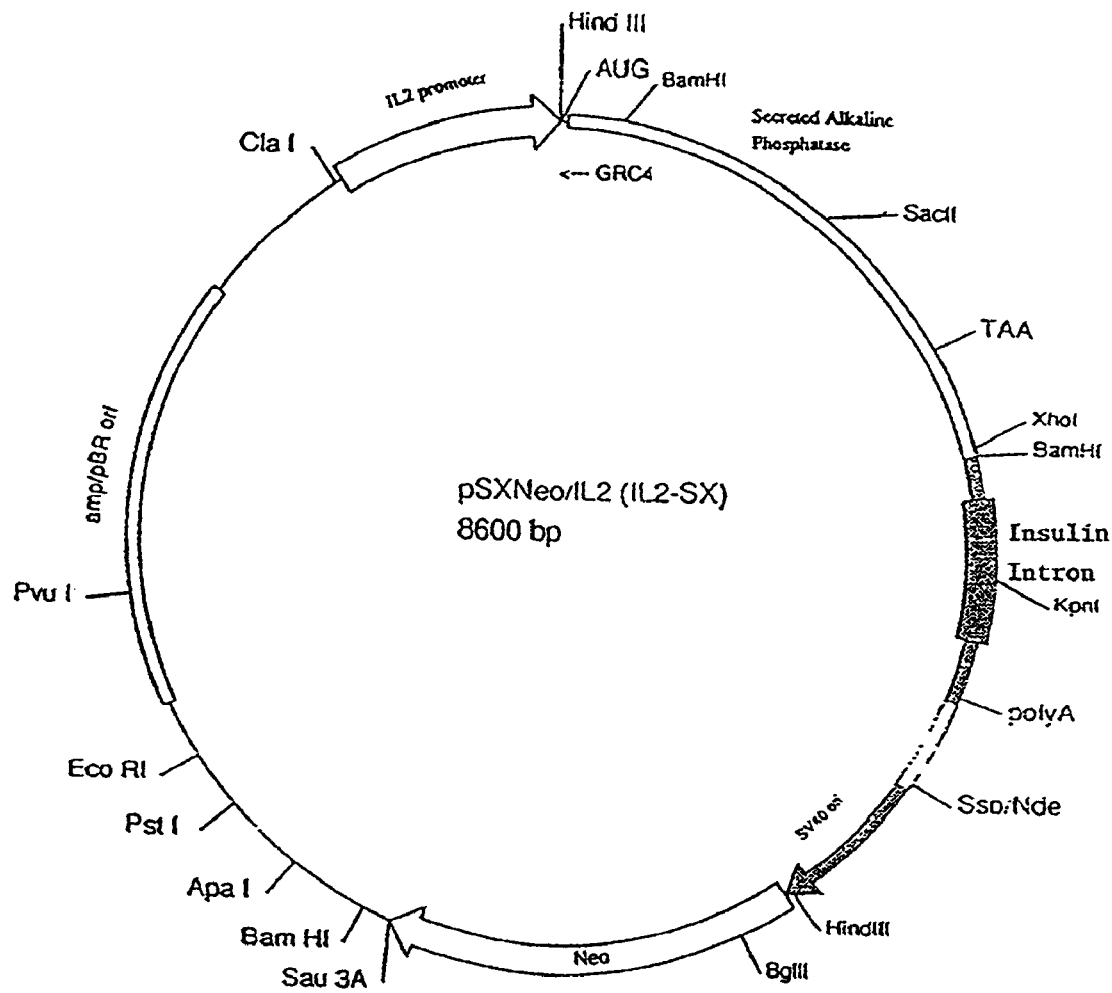
FIG. 1 is a diagram of the plasmid pSXNeo/IL2 (IL2-SX). In NF-AT-SX, the HindIII-ClaI DNA fragment from IL2-SX containing the IL2 enhancer/promoter, is replaced by a minimal IL-2 promoter conferring basal transition and an inducible element containing three tandem NFAT-binding sites (described below).

Induction of Isolated IL-2 Enhancer-Binding Transcription Factors by Cross-Linking the CD3 Chain of the T-Cell Receptor The plasmid pSXNeo/IL2 (IL2-SX) (FIG. 1), which contains the placental secreted alkaline phosphatase gene under the control of human IL-2 promoter (−325 to +47; MCB(86) 6, 3042), and related plasmid variants (i.e. NFAT-SX, NF B-SX, OAP/Oct1-SX, and AP-1-SX) in which the reporter gene is under the transcriptional control of the minimal IL-2 promoter (−325 to −294 and −72 to −47) combined with synthetic oligomers containing various promoter elements (i.e. NFAT, NK B, OAP/Oct-1, and AP1, respectively), were made by three piece ligations of 1) pPL/SEAP (Berger, et al., Gene (1988) 66,1) cut with SspI and HinIII; 2) pSV2/Neo (Southern and Berg, J. Mol. Appl. Genet. (1982) 1, 332) cut with NdeI, blunted with Klenow, then cut with PvuI; and 3) various promoter-containing plasmids (i.e. NFAT-CD8, B-CD8, cx12lacZ-Oct-1, AP1-LUCIF3H, or cx15IL2) described below) cut with PvuI and HindIII, NFAT-CD8 contains 3 copies of the NFAT-binding site (−286 to 31 257; Genes and Dev. (1990)4, 1823) and cx12lacZ-Oct contains 4 copies of the QAP/Oct-1(ARRE-1) binding site (MCB, (1988) 8, 1715) from the human IL-2 enhancer; B-CD8 contains 3 copies of the NFB binding site from the murine light chain (EMBO (1990) 9, 4425) and AP1-LUCIF3H contains 5 copies of the AP-1 site (5'-TGA-CTCAGCGC-3' [SEQ ID NO:3]) from the metallothionen promoter.

Figure 5:
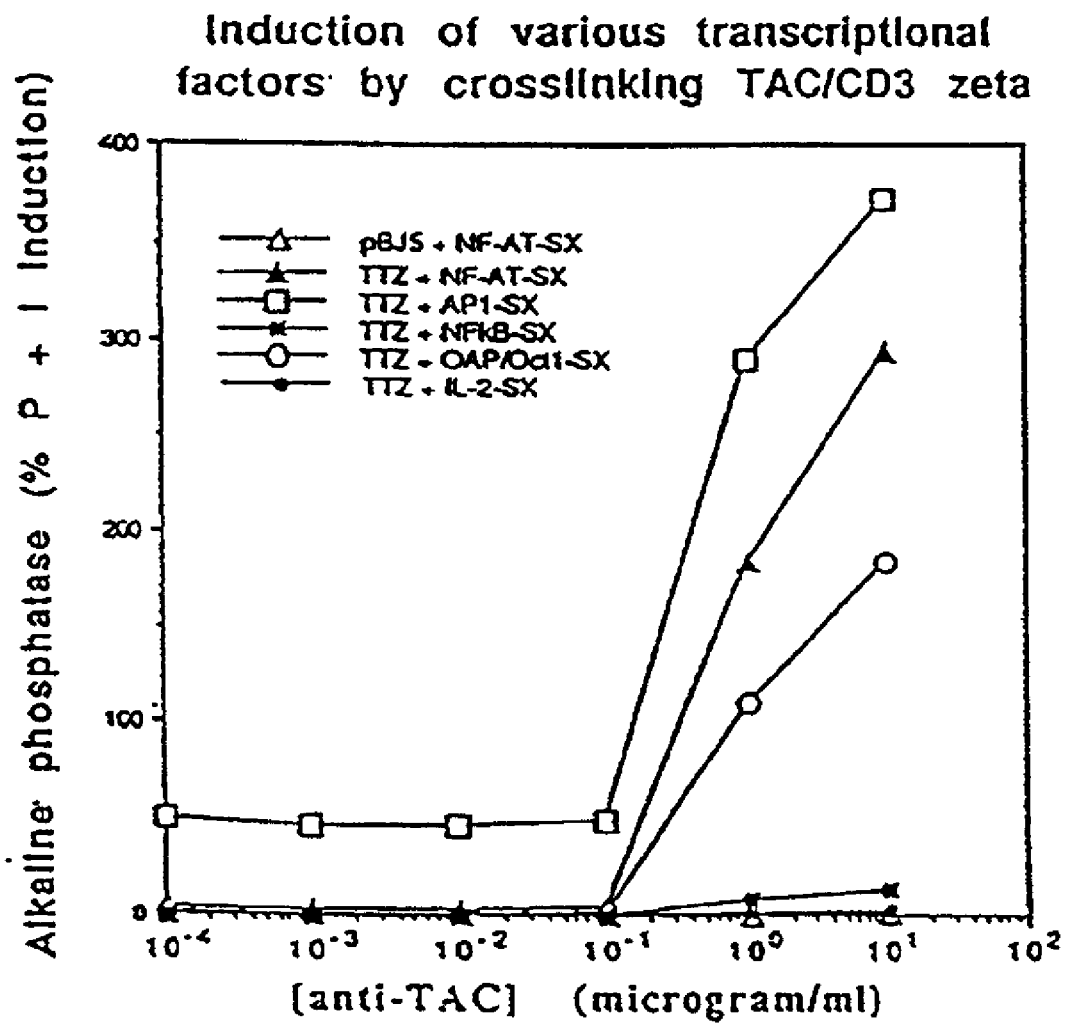
FIG. 5 is a chart of the response of reporter constructs having different enhancer groups to reaction of the receptor TAC/CD3 ζ with a ligand.

In each transfection, 5 µg of expression vector, pCDL-SR (MCB 8, 466–72) (Tac-IL2 receptor-chain), encoding the chimeric receptor TAC/TAC/Z (TTZ) (*PNAS* 88, 8905–8909), was co-transfected along with various secreted alkaline phosphatase-based reporter plasmids (see map of pSXNeo/IL2 in FIG. 1) in TAg Jurkat cells (a derivative of the human T-cell leukemia line Jurkat stably transfected with the SV40 large T antigen (Northrup, et al., *J. Biol. Chem.* [1993]). Each reporter plasmid contains a multimerized oligonucleotide of the binding site for a distinct IL-2 enhancer-binding transcription factor within the context of the minimal IL-2 promoter or, alternatively, the intact IL-2 enhancer/promoter upstream of the reporter gene. After 24 hours, aliquots of cells (approximately $10^5$) were placed in microtiter wells containing log dilutions of bound anti-TAC (CD25) mAb (33B3.1; AMAC, Westbrook, Me.). As a positive control and to control for transfection efficiency, ionomycin (1 µm) and PMA (25 ng/ml) were added to aliquots from each transfection. After an additional 14 hour incubation, the supernatants were assayed for the alkaline phosphatase activity and these activities were expressed relative to that of the positive control samples. The addition of 1 ng/ml FK506 dropped all activity due to NFAT to background levels, demonstrating that deactivations are in the same pathway as that blocked by FK506. Each data point obtained was the average of two samples and the experiment was performed several times with similar results. See FIG. 5. The data show that with a known extracellular receptor, one obtains an appropriate response with a reporter gene and different enhancers. Similar results were obtained when a MAb against the TcR complex (i.e. OKT3) was employed.

Example 2

Inhibitory Activity of the Immunosuppressant Drugs FK506 and Cyclosporin A (CsA) or the Dimeric Derivative Compounds FK1012A (8), FK1012B (5), and CsA dimer (PB-1-218)

Figure 6A:
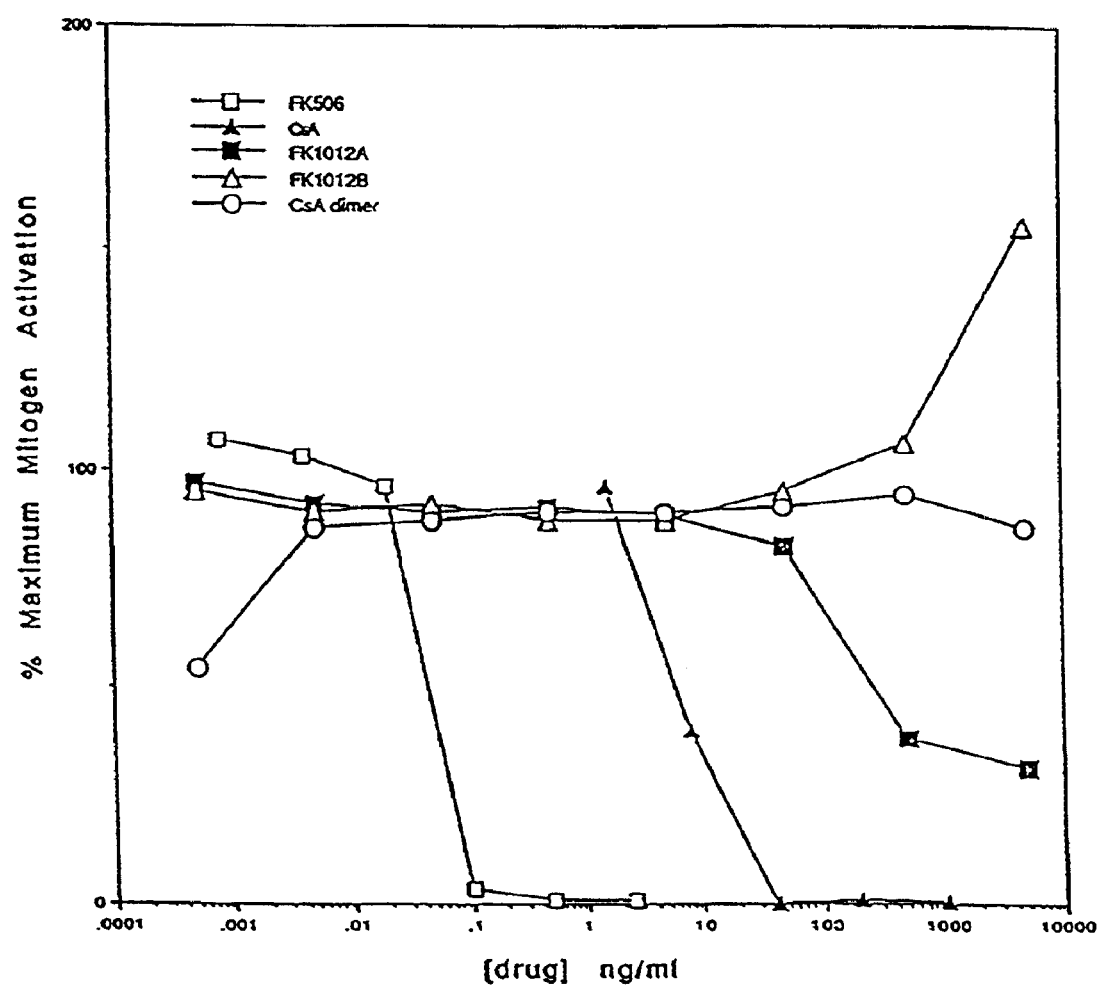

Ionomycin (1 µm) and PMA (25 ng/ml) were added to $10^5$ TAg-Jurkat cells. In addition, titrations of the various drugs were added. After 5 hours the cells were lysed in mild detergent (i.e. Triton X-100) and the extracts were incubated with the β-galactosidase substrate, MUG (methyl galactosidyl umbelliferone) for 1 hour. A glycine/EDTA stop buffer was added and the extracts assayed for fluoresces. Each data point obtained was the average of two samples and the experiment was performed several times with similar results. Curiously, FK1012B appears to augment mitogen activity slightly at the highest concentration (i.e. 5 µg/ml); however, a control experiment shows that FK1012B is not stimulatory by itself. See FIG. 6.

Example 3

Figure 7:
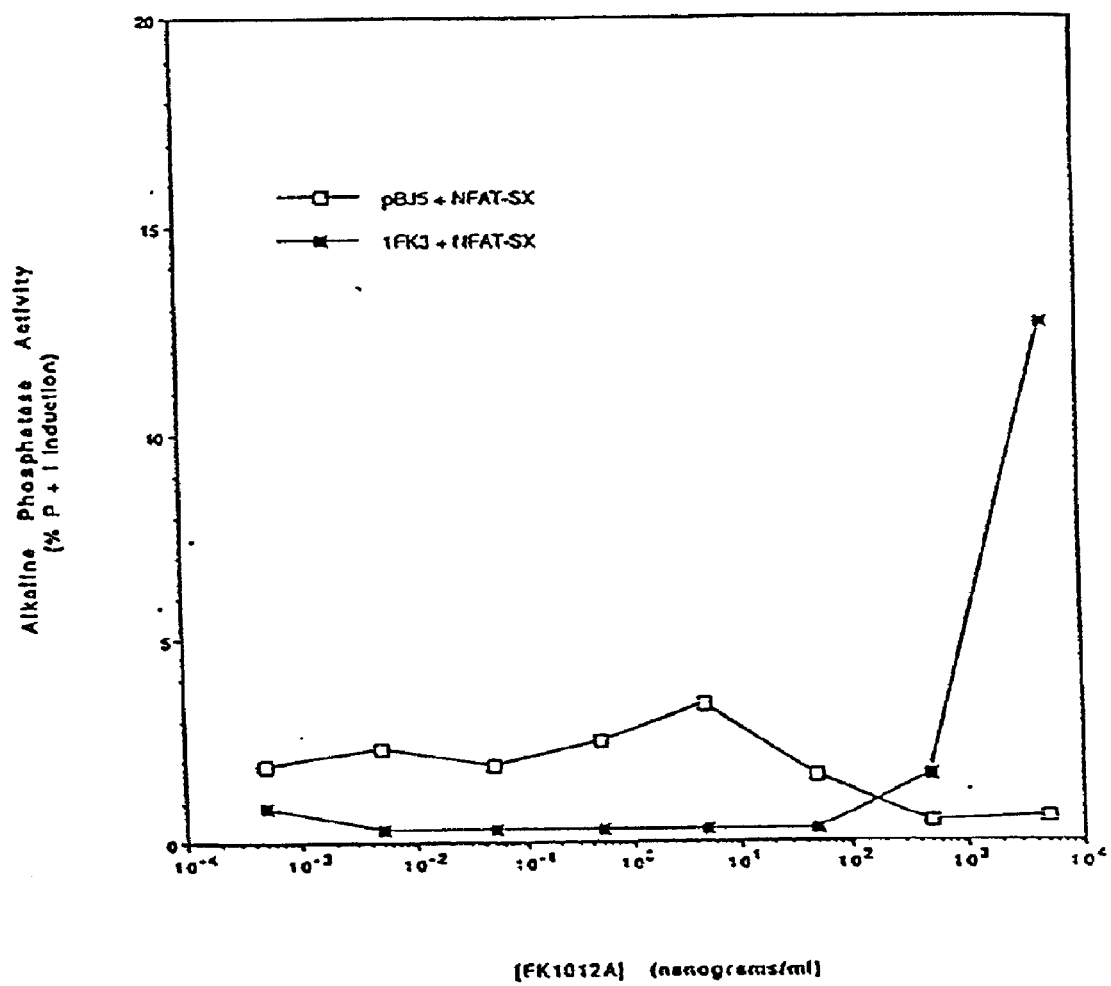
FIG. 7 is a chart of the activity of the ligand FK1012A (8 FIG. 9B) with the extracellular receptor 1FK3 (FKBPx3/CD3 ζ).

Activity of the Dimeric FK506 Derivative FK1012A on the Chimeric FKBP12/CD3 (1FK3) Receptor 5 µg of the eukaryotic expression vector, pBJ5, (based on pCDL-SR with a polylinker inserted between the 16S splice site and the poly A site), containing the chimeric receptor (1FK3), was co-transfected with 4 µg of the NFAT-inducible secreted alkaline phosphatase reporter plasmid, NFAT-SX. As a control, 5 µg of pBJ5 was used, instead of 1FK3/pBJ5, in a parallel transfection. After 24 hours, aliquots of each transfection containing approximately $10^5$ cells were incubated with log dilutions of the drug, FK1012A, as indicated. As a positive control and to control for transfection efficiency, ionomycin (1 µm) and PMA (25 ng/ml) were added to aliquots from each transfection. After an additional 14 hour incubation, the supernatants were assayed for alkaline phosphatase activity and these activities were expressed relative to that of the positive control samples. The addition of 2 ng/ml FK506 dropped all stimulations to background levels, demonstrating that the activations are in the same pathway as that blocked by FK506. Hence, FK506 or cyclosporin will serve as effective antidotes to the use of these compounds. Each data point obtained was the average of two samples and the experiment was performed several times with similar results. See FIG. 7.

Example 4A

Activity of the Dimeric FK506 Derivative, FK1012B, on the Myristoylated Chimeric CD3/ FKBP12 (MZF3E) Receptor We have successfully demonstrated a number of approaches to ligand design and syntheses, including positive results with FK506-based HOD reagents named "FK1012"s. We have found that FK1012s achieve high affinity, 2:1 binding stoichiometry ($K_d(1)$=0.1 nM; $K_d(2)$= 0.8 nM) and do not inhibit calcineurin-mediated TCR signaling. The ligands are neither "immunosuppressive" nor toxic (up to 0.1 mM in cell culture). Similarly, we have prepared a cyclosporin A-based homodimerizing agent, "(CsA)2" which binds to the CsA receptor, cyclophilin, with 1:2 stoichiometry, but which does not bind to calcineurin. Thus, like FK1012s, (CsA)2 does not inhibit signalling pathways and is thus neither immunosuppressive nor toxic.

Figure 18A:
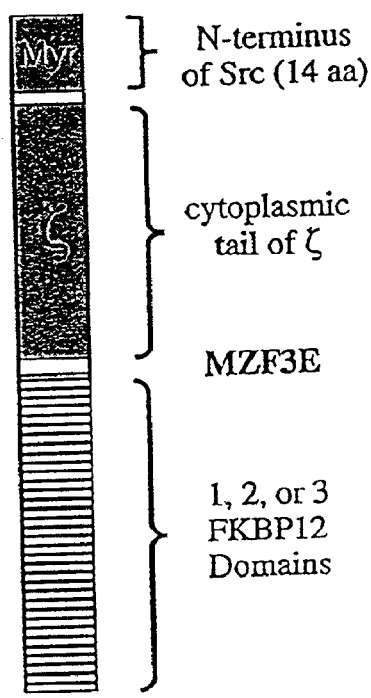
FIGS. 18A and 18B is an overview of the fusion cDNA construct and protein MZF3E.
Figure 18B:
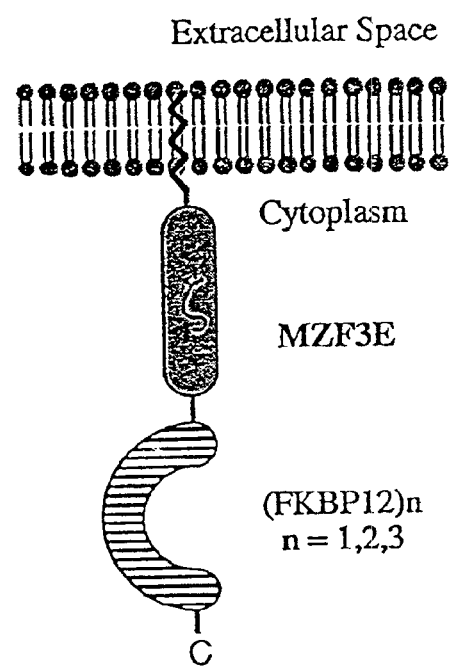

These and other of our examples of ligand-mediated protein association resulted in the control of a signal transduction pathway. In an illustrative case, this was accomplished by creating an intracellular receptor comprised of a small fragment of Src sufficient for posttranslational myristoylation (M), the cytoplasmic tail of zeta (Z; a component of the B cell receptor was also used), three consecutive FKBP12M (F3) and a flu epitope tag (E). Upon expressing the construct MZF3E (FIG. 18) in human (Jurkat) T cells, we confirmed that the encoded chimeric protein underwent FK1012-mediated oligomerization. The attendant aggregation of the zeta chains led to signaling via the endogenous TCR-signaling pathway (FIG. 15), as evidenced by secretion of alkaline phosphatase (SEAP) in response to an FK1012 ($EC_{50}$=50 nM). The promoter of the SEAP reporter gene was constructed to be transcriptionally activated by nuclear factor of activated T cells (NFAT), which is assembled in the nucleus following TCR-signaling. FK1012-induced signaling can be terminated by a deaggregation process induced by a nontoxic, monomeric version of the ligand called FK506-M.

Figure 8:
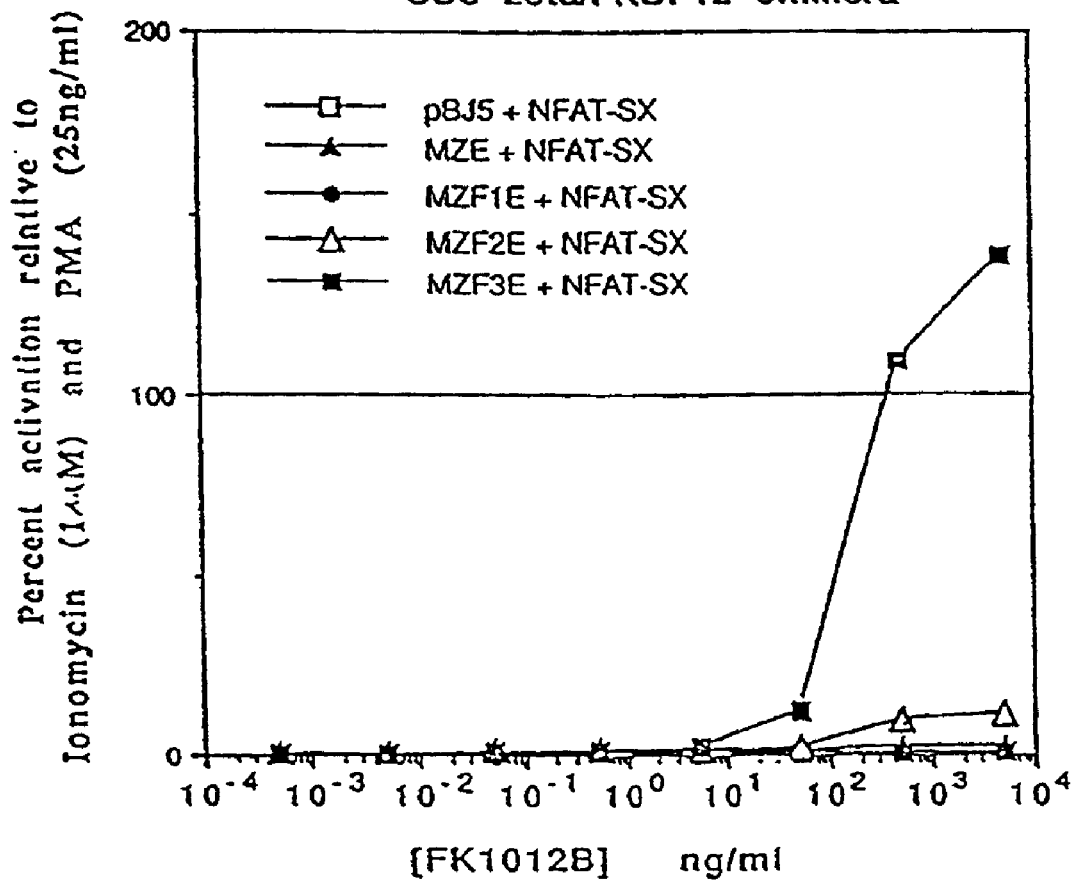
FIG. 8 is a chart of the activation of an NFAT reporter via signalling through a myristoylated CD3 ζ/FKBP12 chimera.

Specifically, 5 µg of the eukaryotic expression vector, pBJ5, containing a myristoylated chimeric receptor was transfected with 4 µg NFAT-SX MZE, MZF1E, MZF2E and MZF3E contain 0, 1, 2, or 3 copies of FKBP12, respectively, downstream of a myristoylated CD3 cytoplasmic domain (see FIG. 2). As a control, 5 µg of pBJ5 was used in a parallel transfection. After 24 hours, aliquots of each transfection containing approximately $10^5$ cells were incubated with log dilutions of the drug, FK1012B, as indicated. As a positive control and to control for transfection efficiency, ionomycin (1 μm) and PMA (25 ng/ml) were added to aliquots from each transfection. After an additional 12 hour incubation, the supernatants were assayed for alkaline phosphatase activity and these activities were expressed relative to that of the positive control samples. The addition of 1 ng/ml FK506 dropped all stimulations to near background levels, demonstrating that the activations are in the same pathway as that blocked by FK506. This result is further evidence of the reversibility of the subject cell activation. Each data point obtained was the average of two samples and the experiment was performed several times with similar results. See FIG. 8. The myristoylated derivatives respond to lower concentrations of the ligand by about an order of magnitude and activate NF-AT dependent transcription to comparable levels, but it should be noted that the ligands are different Compare FIGS. 7 and 8.

In vivo FK1012-induced protein dimerization. We next wanted to confirm that intracellular aggregation of the MZF3E receptor is indeed induced by the FK1012. The influenza haemagglutinin epitope-tag (flu) of the MZF3E-construct was therefore exchanged with a different epitope-tag (flag-M2). The closely related chimeras, MZF3E$_{flu}$ and MZF3E$_{flag}$, were coexpressed in Jurkat T cells. Immunoprecipitation experiments using anti-Flag-antibodies coupled to agarose beads were performed after the cells were treated with FK1012A. In the presence of FK1012A (1 μM) the protein chimera MZF3E$_{flag}$ interacts with MZEF3E$_{flu}$ and is coimmunoprecipitated with MZF3E$_{flag}$. In absence of FK1012A, no coimmunoprecipitation of MZF3E$_{flu}$ is observed. Related experiments with FKBP monomer constructs MZF3E$_{flu}$ and MZF3E$_{flag}$, which do not signal, revealed that they are also dimerized by FK1012A. This reflects the requirement for aggregation observed with both the endogenous T cell receptor and our artificial receptor MZF3E.

FK1012-induced protein-tyrosine phosphorylation. The intracellular domains of the TCR, CD3 and zeta-chains interact with cytoplasmic protein tyrosine kinases following antigen stimulation. Specific members of the Src family (lck and/or fyn) phosphorylate one or more tyrosine residues of activation motifs within these intracellular domains (tyrosine activation motif, TAM). The tyrosine kinase ZAP-70 is recruited (via its two SH2 domains) to the tyrosine phosphorylated T-cell-receptor, activated, and is likely to be involved in the further downstream activation of phospholipase C. Addition of either anti-CD3 MAb or FK1012A to Jurkat cells stably transfected with MZF3E resulted in the recruitment of kinase activity to the zeta-chain as measured by an in vitro kinase assay following immunoprecipitation of the endogenous T cell receptor zeta chain and the MZF3E-construct, respectively. Tyrosine phosphorylation after treatment of cells with either anti-CD3 MAb or FK1012 was detected using monoclonal alpha-phosphotyrosine antibodies. Whole cell lysates were analysed at varying times after stimulation. A similar pattern of tyrosine-phosphorylated proteins was observed after stimulation with either anti-CD3 MAb or FK1012. The pattern consisted of a major band of 70 kDa, probably ZAP-70, and minor bands of 120 kDa, 62 kDa, 55 kDa and 42 kDa.

Example 4(B)

Regulation of Programmed Cell Death with Immunophilin-Fas Antigen Chimeras

The Fas antigen is a member of the nerve growth factor (NGF)/tumor necrosis factor (TNF) receptor superfamily of cell surface receptors. Crosslinking of the Fas antigen with antibodies to its extracellular domain activates a poorly understood signaling pathway that results in programmed cell death or apoptosis. The Fas antigen and its associated apoptotic signaling pathway are present in most cells including possibly all tumor cells. The pathway leads to a rapid and unique cell death (2 h) that is characterized by condensed cytoplasm, the absence of an inflammatory response and fragmentation of nucleosomal DNA, none of which are seen in necrotic cell death.

We have also developed a second, inducible signaling system that leads to apoptotic cell death. Like the MZF3E pathway, this one is initiated by activating an artificial receptor that is the product of a constitutively expressed "responder" gene. However, the new pathway differs from the first in that our HOD reagents induce the synthesis of products of an endogenous pathway rather than of the product of a transfected, inducible (e.g., reporter) gene.

Gaining control over the Fas pathway presents significant opportunities for biological research and medicine. Transgenic animals can be designed with "death" responder genes under the control of cell-specific promoters. Target cells may then be chemically ablated in the adult animal by administering a HOD reagent to the animal. In this way, the role of specific brain cells in memory or cognition or immune cells in the induction and maintenance of autoimmune disorders could be assessed. Death responder genes may also be introduced into tumors using the human gene therapy technique developed by M. Blaese and co-workers (Culver et al, Science 256 5063 (1992): 1550–2) and then subsequently activated by treating the patient with a HOD reagent (in analogy to the "gancyclovir" gene therapy clinical trials recently reported for the treatment of brain tumors). Finally, we contemplate the coadministration of a death-responder gene together with the therapeutic gene in the practice of gene therapy. This would provide a "failsafe" component to gene therapy. If something were to go awry (a commonly discussed concern is an integration-induced loss of a tumor suppressor gene leading to cancer), the gene therapy patient could take a "failsafe" pill that would kill all transfected cells. We have therefore designed a system of orthogonal oligomerizing reagents for such purposes. Thus we provide for the use of one set of ligands and chimeric responder proteins for regulating apoptosis in the host cells, and another set for regulating the transcription of therapeutic genes. The ligands used for regulating transcription of a therapeutic or desired gene are designed (or selected) to not cross-react and initiate apoptosis.

Figure 19:
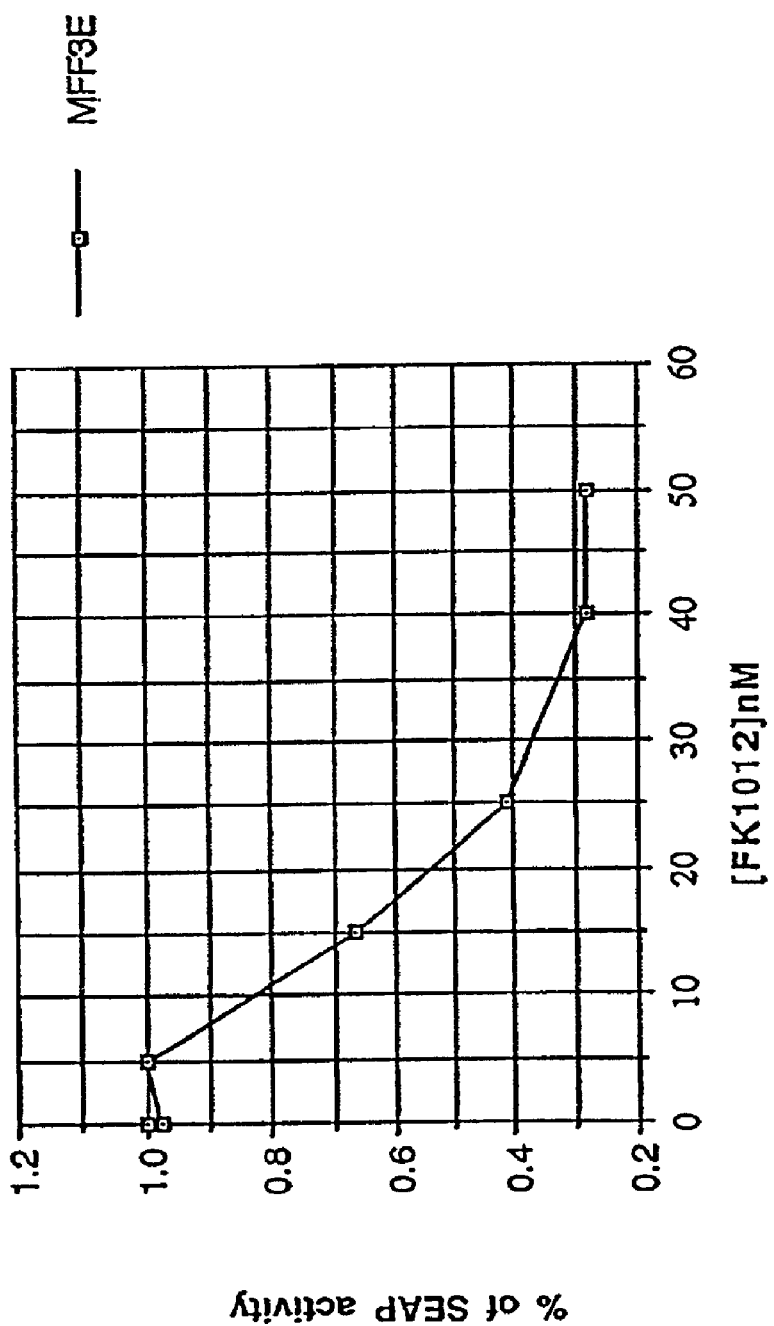
FIG. 19 shows FK1012-induced cell death of the Jurkat T-cell line transfected with a myristoylated Fas-FKBP12 fusion protein (MFF3E), as indicated by the decreased transcriptional activity of the cells.

An exemplary chimeric cDNA has been constructed consisting of three FKBP12 domains fused to the cytoplasmic signaling domain of the Fas antigen (FIG. 19). This construct, when expressed in human Jurkat and murine D10 T cells, can be induced to dimerize by an FK1012 reagent and initiate a signaling cascade resulting in FK1012-dependent apoptosis. The LD$_{50}$ for FK1012A-mediated death of cells transiently transfected with MFF3E is 15 nM as determined by a loss of reporter gene activity (FIG. 19; for a discussion of the assay, see legend to FIG. 20). These data coincide with measurements of cell death in stably transfected cell lines. Since the stable tansfectants represent a homogeneous population of cells, they have been used to ascertain that death is due to apoptosis rather than necrosis (membrane blebbing, nucleosomal DNA fragmentation). However, the transient transfection protocol is more convenient and has therefore been used as an initial assay system, as described below.

Example 4(C)

Regulation of Programmed Cell Death with Cyclophilin-Fas Antigen Chimeras

We have also prepared a series of cyclophilin C-Fas antigen constructs and assayed their ability to induce (CsA)

Figure 20A:
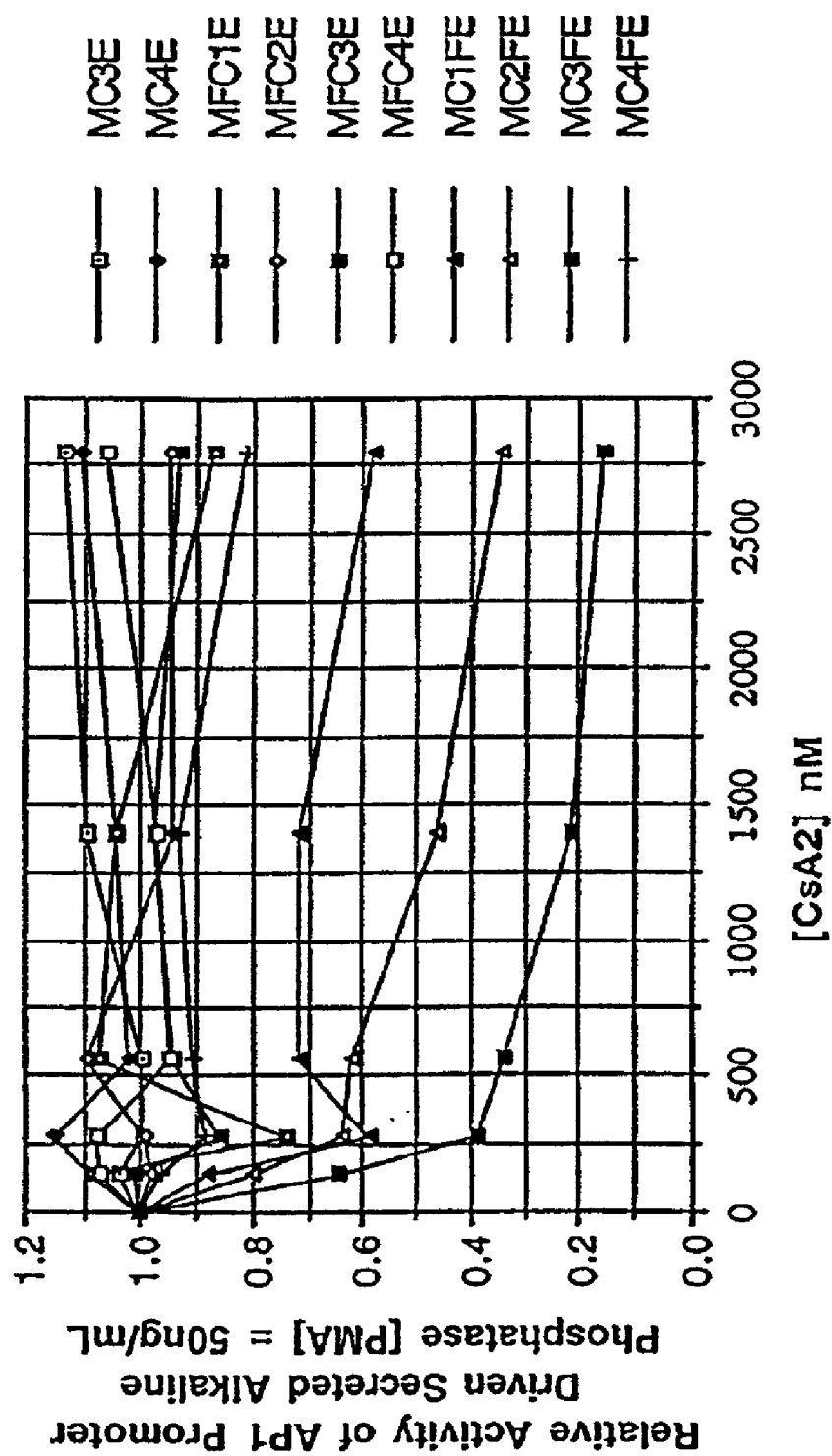
FIG. 20A is an analysis of cyclophilin-Fas (and Fas-cyclophilin) fusion constructs in the transient transfection assay. MC3FE was shown to be the most effective in this series.
Figure 20B:
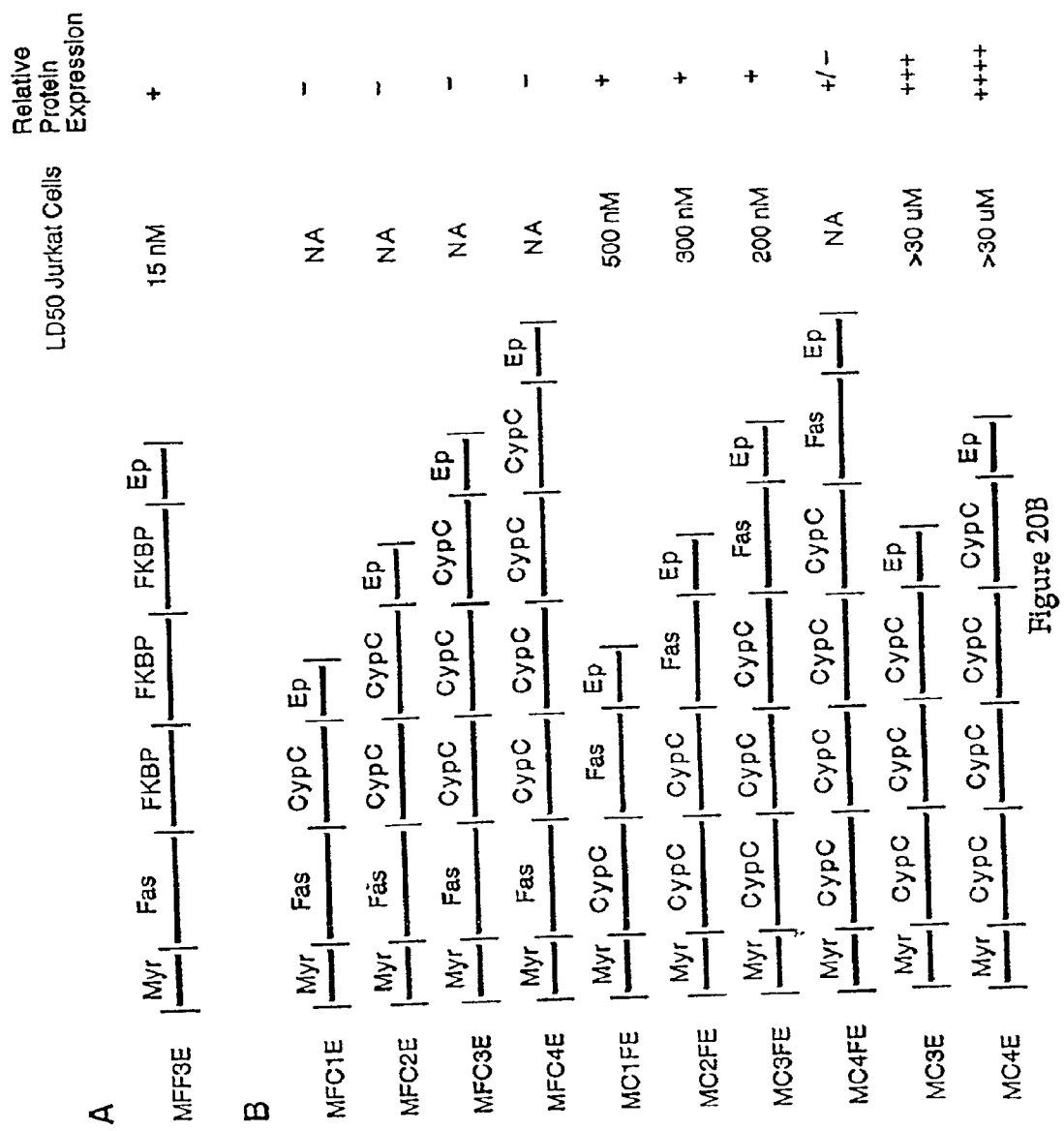
FIG. 20B depicts Immunophilin-Fas antigen chimeras and results of transient expression experiments in Jurkat T cells stably transformed with large T-antigen. Myr: the myristylaion sequence taken from $pp60^{c-src}$ encoding residues 1–14 (Wilson et al. *Mol & Cell Biol* 9 4 (1989): 1536–44); FKBP: human FKBP12; CypC: murine cyclophilin C sequence encoding residues 36–212 (Freidman et al, *Cell* 66 4 (1991): 799–806); Fas: intracellular domain of human Fas antigen encoding residues 179–319 (Oehm et al, *J Biol Chem* 267 15 (1992): 10709–15). Cells were electroporated with a plasmid encoding a secreted alkaline phosphatase reporter gene under the control of 3 tandem AP1 promoters along with a six fold molar excess of the immunophilin fusion construct. After 24 h the cells were stimulated with PMA (50 ng/mL), which stimulates the synthesis of the reporter gene, and (CsA)2. At 48 h the cells were assayed for reporter gene activity. Western blots were performed at 24 h using anti-HA epitope antibodies.

2-dependent apoptosis in transient expression assays (FIG. 20A). In addition, (CsA)2-dependent apoptosis has been demonstrated with human Jurkat T cells stably transfected with the most active construct in the series, MC3FE (M=myristoylation domain of Src, C=cyclophilin domain, F=cytoplasmic tail of Fas, E=flu epitope tag). The cytoplasmic tail of Fas was fused either before of after 1, 2, 3, or 4 consecutive cyclophilin domains. Two control constructs were also prepared that lack the Fas domain. In this case we observed that the signaling domain functions only when placed after the dimerization domains. (The zeta chain constructs signal when placed either before or after the dimerization domains.) Both the expression levels of the eight signaling constructs, as ascertained by Western blotting, and their activities differed quantitatively (FIG. 20B). The optional system has thus far proved to be MC3FE. The $LF_{50}$ for (CsA)2-mediated cell death with MC3FE is ~200 nM. These data demonstrate the utility of the cyclophilin-cyclosporin interactions for regulating intracellular protein association and illustrate an orthogonal reagent system that will not cross-react with the FKBP12-FK1012 system. Further, in this case, the data show that only dimerization and not aggregation is required for initiation of signal transduction by the Fas cytoplasmic tail.

Mutation of the N-terminal glycine of the myristoylation signal to an alanine prevents myristoylation and hence membrane localization. We have also observed that the mutated construct (ΔMFF3E) was equally potent as an inducer of FK1012-dependent apoptosis, indicating that membrane localization is not necessary for Fas-mediated cell death.

Example 5

Construction of Murine Signalling Chimeric Protein

Figure 4A:
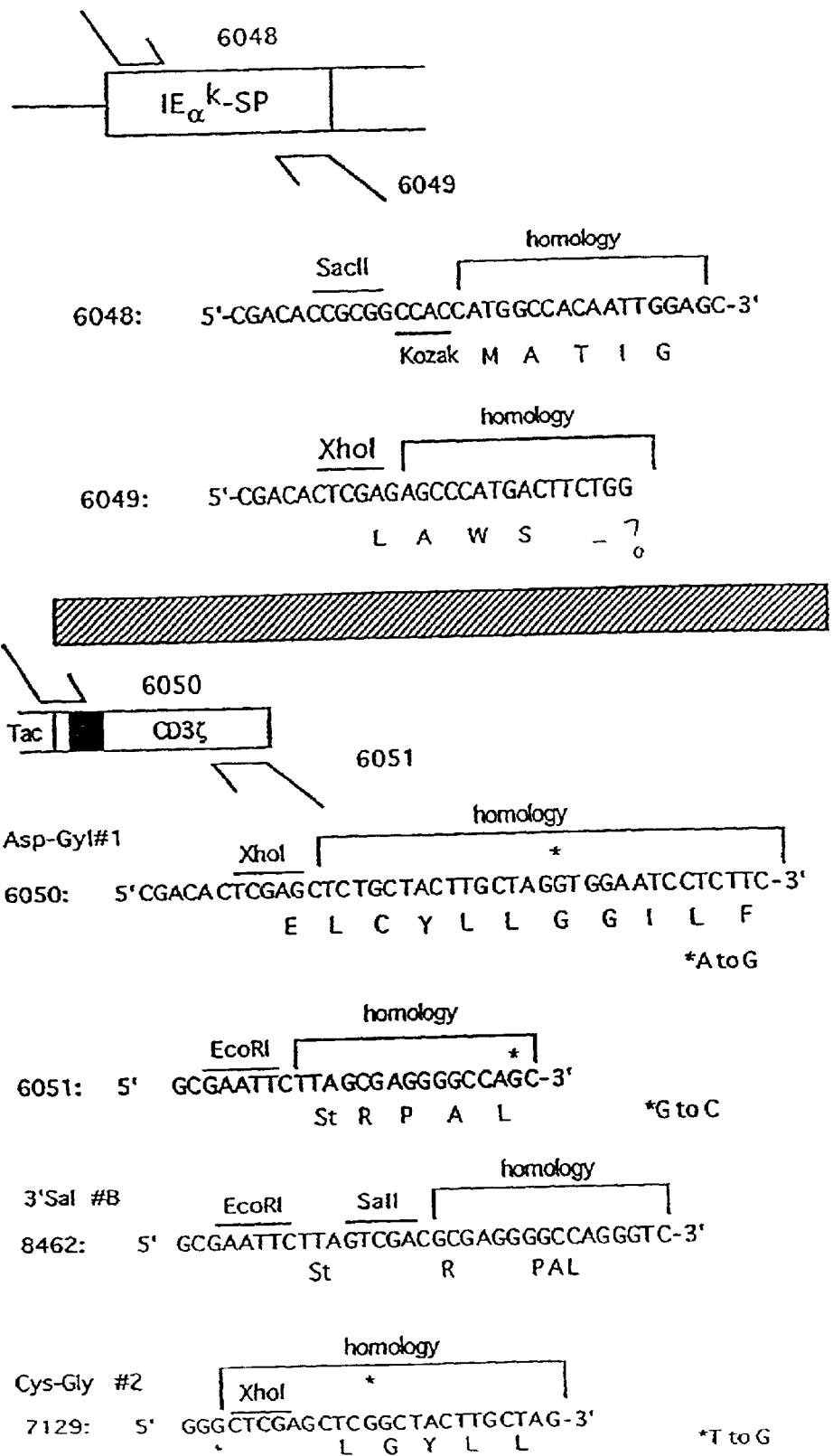

The various fragments were obtained by using primers described in FIG. 4. In referring to primer numbers, reference should be made to FIG. 4.

An approximately 1.2 kb cDNA fragment comprising the I-E chain of the murine class II MHC receptor (*Cell*, 32, 745) was used as a source of the signal peptide, employing P#6048 and P#6049 to give a 70 bp SacII-XhoI fragment using PCR as described by the supplier (Promega). A second fragment was obtained using a plasmid comprising Tac (IL2 receptor chain) joined to the transmembrane and cytoplasmic domains of CD3 (*PNAS*, 88, 8905). Using P#6050/and P#6051, a 320 bp XhoI-EcoRI fragment was obtained by PCR comprising the transmembrane and cytoplasmic domains of CD3. These two fragments were ligated and inserted into a SacII-EoRI digested pBluescript (Stratagene) to provide plasmid, SPZ/KS.

Figure 3B:
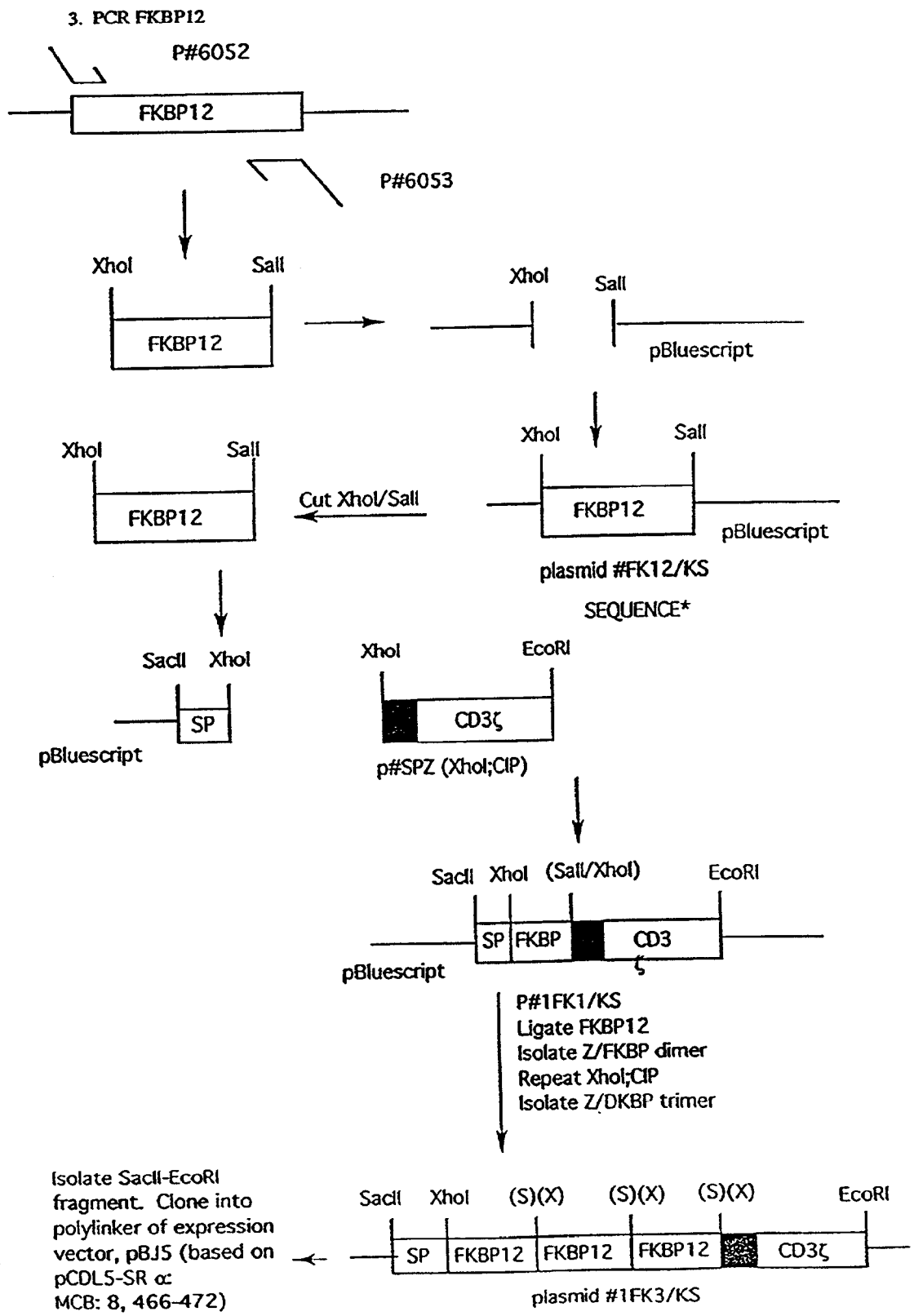

To obtain the binding domain for FK506, plasmid rhEKBP (provided by S. Schreiber, Nature (1990) 346, 674) was used with P#6052 (SEQ ID NO:33) and P#6053 (SEQ ID NO:35) to obtain a 340 bp XhoI-SalI fragment containing human FKBP12. This fragment was inserted into pBluescript digested with XHoI and SalI to provide plasmid FK12/KS, which was the source for the FKBP12 binding domain. SPZ/KS was digested with XhoI, phosphatased (cell intestinal alkaline phosphatase; CIP) to prevent self-annealing, and combined with a 10-fold molar excess of the XhoI-SalI FKBP12-containing fragment from FK12/KS. Clones were isolated that contained monomers, dimers, and timers of FKBP12 in the correct orientation. The clones 1FK1/KS, 1FK2/KS, and 1FK3/KS are comprised of in the direction of transcription; the signal from the murine MHC class II gene I-E, a monomer, dimer of trimer, respectively, of human FKBP12, and the transmembrane and cytoplasmic portions of CD3. Lastly, the SacII-EcoRI fragments were excised from pBluescript using restriction enzymes and ligated into the polylinker of pBJ5 digested with SacII and EcoRI to create plasmids 1FK1/pBJ5, 1FK2/pBJ5, and 1FK3/pBJ5, respectively. See FIGS. 3 and 4 (SEQ ID NOs: 4–6, 8–10, 12, 14–35, 37–40).

Example 6

A. Construction of Intracellular Signaling Chimera

A myristoylation sequence from c-src was obtained from Pellman, et al., Nature 314, 374, and joined to a complementary sequence of CD3 to provide a primer which was complementary to a sequence 3' of the transmembrane domain namely P#8908 (SEQ ID NO: 23). This primer has a SacII site adjacent to the 5' terminus and a XhoI sequence adjacent to the 3' terminus of the myristoylation sequence. The other primer P#8462 (SEQ ID NO:21) has a SalI recognition site 3' of the sequence complementary to the 3' terminus of CD3, a stop codon and an EcoRI recognition site. Using PCR, a 450 bp SacII-EcoRI fragment was obtained, which was comprised of the myristoylation sequence and the CD3 sequence fused in the 5' to 3' direction. This fragment was ligated into SacII/EcoRI-digested pBJ5(XhoI)(SalI) and cloned, resulting in plasmid MZ/pBJ5. Lastly, MZ/pBJ5 was digested with SalI, phosphatased, and combined with a 10-fold molar excess of the XhoI-SalI FKBP12-containing fragment from FK12/KS and ligated. After cloning, the plasmids comprising the desired constructs having the myristoylation sequence, CD3 and FKBP12 multimers in the 5'-3'-direction were isolated and verified as having the correct structure. See FIGS. 2 and 4 (SEQ ID NOs: 4–6, 8–10, 12, 14–35, 37–40).

B. Construction of Expression Cassettes for Intracellular Signal Chimeras

The construct MZ/pBJ5 (MZE/pBJ5) is digested with restriction enzymes XhoI and SalI the TCR ζ fragment is removed and the resulting vector is ligated with a 10 fold excess of a monomer, dimer, trimer or higher order multimer of FKBP12 to make MF1E, MF2E, MF3E or $MF_nE$/pBJ5. Active domains designed to contain compatible flanking restriction sites (i.e. XhoI and SalI) can then be cloned into the unique XhoI or SalI restriction sites of $MF_nE$/pBJ5.

Example 7

Construction of Nuclear Chimera

A. GAL4 DNA Binding Domain-FKBP Domain(s)-Epitope Tag. The GAL4 DNA binding domain (amino acids 1–147) was amplified by PCR using a 5' primer (#37) that contains a SacII site upstream of a Kozak sequence and a translational start site, and a 3' primer (#38) that contains a SalI site. The PCR product was isolated, digested with SacII and SalI and ligated into pBluescript II KS(+) at the SacII and SalI Sites, generating the construct pBS-GAL4. The construct was verified by sequencing. The SacII/SalI fragment from pBS-GAL4 was isolated and ligated into the IFK1/pBJ5 and IFK3/pBJ5 constructs (containing the myristoylation sequence, see Example 6) at the SacII and XhoI sites, generating constructs GF1E, GF2E and GE3E.

5'end of PCR amplified product:
```
              |----GAL4 (I-147)--->>
                                              (SEQ ID NO: 44)
     Sac II        M  K  L  S  S  I
                                              (SEQ ID NO: 41)
5' CGACACCGCGGCCACCATGAAGCTACTGTCTTCTATCG
            Kozak 3'end of PCR amplified product:
     <<----GAL4 (1-147----) |
      R  Q  L  T  V  S                         (SEQ ID NO: 46)
5' GACAGTTGACTGTATCGGTCGACTGTCG               (SEQ ID NO: 45)

3' CTGTCAACTGACATAGCCAGCTGACAGC                (SEQ ID NO: 77)
              SalI
```

B. HNF1 dimerization/DNA binding domain-FKBP domain(s)-tag. The HNF1a dimerization/DNA binding domain (amino acids 1–282) was amplified by PCR using a 5' primer (#39) that contains a SacII site upstream of a Kozak sequence and a translational start site, and a 3' primer (#40) that contains a SalI site. The PCR product was isolated, digested with SacII and SalI, and ligated into pBluescript II KS(+) at the SacII and SalI sites, generating the construct pBS-HNF. The construct was verified by sequencing. The SacII/SalI fragment from pBS-HNF was isolated and ligated into the IFK1/pBJ5 and IFK/pBJ5 constructs at the SacII and XhoI sites, generating constructs HF1E, HF2E and HF3E.

```
5' end of PCR amplified product:
SacII              |--HNF1(1-281)-->>
                                              (SEQ ID NO: 50)
                 M  V  S  K  L  S
                                              (SEQ ID NO: 49)
5' CGACACCGCGGCCACCATGGTTTCTAAGCTGAGC
            Kozak 3'end of PCR amplified product:
     <<------HNF1 (1-282)-----|
     A  F  R  H  K  L                          (SEQ ID NO: 52)
5' CCTCCGGCACAAGTTGGTCGACTGTCG                (SEQ ID NO: 51)

3' GGAAGGCCGTGTTCAACCAGCTGACAGC                (SEQ ID NO: 78)
              SalI
```

C. FKBP Domain(s)-VP16 Transcrip. Activation Domain (s)-Epitope Tag.

These constructs were made in three steps: (i) a construct was created from IFK3/pBJ5 in which the myristoylation sequence was replaced by a start site immediately upstream of an XhoI site, generating construct SF3E; (ii) a nuclear localization sequence was inserted into the XhoI site, generating construct NF3E; (iii) the VP16 activation domain was cloned into the SalI site of NF3E, generating construct NF3V1E.

(i). Complementary oligonucleotides (#45 and #46) encoding a Kozak sequence and start site flanked by SacII and XhoI sites were annealed, phosphorylated and ligated into the SacII and XhoI site of MF3E, generating construct SF3E.

Insertion of generic start site.

```
            Kozak
            M  L  E                            (SEQ ID NO: 54)
     5' GGCCACCATGC                            (SEQ ID NO: 53)

3' CGCCGGTGGTACGAGCT                      (SEQ ID NO: 79)
        SacII        XhoI
``` overhang   overhang
—continued (ii). Complementary oligonucleotides (#47 and #48) encoding the SV40 T antigen nuclear localization sequence flanked by a 5' SalI site and a 3' XhoI site were annealed, phosphorylated and ligated into the XhoI site of SF1E, generating the construct NF1E. The construct was verified by DNA sequencing. A construct containing the mutant or defective form of the nuclear localization sequence, in which a threonine is substituted for the lysine at position 128, was also isolated. This is designated NF1E-M. Multimers of the FKBP12 domain were obtained by isolating the FKBP12 sequence as an XhoI/SalI fragment from pBS-FKBP12 and ligating this fragment into NF1E linearized with XhoI. This resulted in the generation of the constructs NF2E and NF3E.

Insertion of NLS into generic start site

```
              T (ACN)
          126              132                 (SEQ ID NO: 59)
        L  D  P  K  K  K  R  K  V  L  E
     5' TCGACCCTAAGAAGAAGAGAAAGGTAC            (SEQ ID NO: 58)

(SEQ ID NO: 80)
     3'      GGGATTCTTCTTCTCTTTCCATGAGCT
         Sal I                         XhoI
```

Threonine at position 128 results in a defective NLS.

(iii). The VP16 transcriptional activation domain (amino acids 413–490) was amplified by PCR using a 5' primer (#43) that contains SalI site and a 3' primer (#44) that contains an XhoI site. The PCR product was isolated, digested with SalI and XhoI, and ligated into MF3E at the XhoI and SalI sites, generating the construct MV1E. The construct was verified by sequencing. Multimerized VP16 domains were created by isolating the single VP16 sequence as a XhoI/SalI fragment from MV1E and ligating this fragment into MV1E linearized with XhoI. Constructs MV2E, MV3E and MV4E were generated in this manner. DNA fragments encoding one or more multiple VP16 domains were isolated as XhoI/SalI fragments from MV1E or MV2E and ligated into NF1E linearized with SalI, generating the constructs NF1V1E and NF1V3E. Multimers of the FKBP12 domain were obtained by isolating the FKBP12 sequence as an XhoI/SalI fragment from pBS-FKBP12 and ligating this fragment into NF1V1E linearized with XhoI. This resulted in the generation of the constructs NF2V1E and NF3V1E.

```
5'end of PCR amplified product:
     SalI    |--VP16(413-490)--->>
             A  P  P  T  D  V                  (SEQ ID NO: 64)
     5' CGACAGTCGACGCCCCCCCGACCGATGTC          (SEQ ID NO: 61)

3'end of PCR amplified product:
     <<-- VP16(413-490)----|
         D  E  Y  G  G                         (SEQ ID NO: 66)
     5' GACGAGTACGGTGGGCTCGAGTGTCG             (SEQ ID NO: 65)

3' CTGCTCATGCCACCCGAGCTCACAGC             (SEQ ID NO: 81)
                       XhoI
```

Oligonucleotides:

```
#37  38mer/0.2 um/OFF  5'CGACACCGCGGCCACCATGAAGCTACTGTCTTCTATCG   (SEQ ID NO: 41)

#38  28mer/0.2 um/OFF  5'CGACAGTCGACCGATACAGTCAACTGTC             (SEQ ID NO: 42)

#39  34mer/0.2 um/OFF  5'CGACACCGCGGCCACCATGGTTTCTAAGCTGAC        (SEQ ID NO: 49)

#40  28mer/0.2 um/OFF  5'CGACAGTCGACCAACTTGTGCCGGAAGG             (SEQ ID NO: 48)

#43  29mer/0.2 um/OFF  5'CGACAGTCGACGCCCCCCCGACCGATGTC            (SEQ ID NO: 61)

#44  26mer/0.2 um/OFF  5'CGACACTCGAGCCCACCGTACTCGTC               (SEQ ID NO: 62)

#45  26mer/0.2 um/OFF  5'GGCCACCATGC                              (SEQ ID NO: 53)

#46  18mer/0.2 um/OFF  5'TCGAGCATGGTGGCCGC                        (SEQ ID NO: 55)

#47  27mer/0.2 um/OFF  5'TCGACCCTAAGA-(C/A)-GAAGAGAAAGGTAC        (SEQ ID NO: 56)

#48  27mer/0.2 um/OFF  5'TCGAGTACCTTTCTCTTC-(G/T)-TCTTAGGG        (SEQ ID NO: 57)
```

Example 8

Demonstration of Transcriptional Induction

Jurkat TAg cells were transfected with the indicated constructs (5 µg of each construct) by electroporation (960 µF, 250 v). After 24 hours, the cells were resuspended in fresh media and aliquoted. Half of each transfection was incubated with the dimeric FK506 derivative, (Example 14) at a final concentration of 1 µM. After 12 hours, the cells were washed and cellular extracts were prepared by repeated freeze-thaw. Chloramphenicol acetyltransferase (CAT) activity was measured by standard protocols. Molecular Cloning: A Laboratory Manual, Sambrook et al. eds. (1989) CSH Laboratory, pp. 16–59 ff. The data demonstrated CAT activity present as expected (in sample 2, with or without ligand; and in samples 5 and 6 in the presence of ligand) in 70 µL of extract (total extract volume was 120 µL) after incubation at 37° C. for 18 hours. The samples employed in the assays are as follows:

1. G5E4TCAT (GAL4-CAT reporter plasmid)
2. G5F4TCAT, GAL4-VP16
3. G5E4TCAT, NF3V1E
4. G5E4TCAT, GF2E
5. G5E4TCAT, GF2E, NF3V1E
6. G5E4TCAT, GE3E, NF3V1E Synthetic Chemistry Examples As indicated elsewhere, compounds of particular interest at present as oligomerization agents have the following structure:

linker-{rbm$_1$, rbm$_2$, . . . rbm$_n$} wherein "linker" is a linker moiety such as described herein which is covalently linked to "n" (an integer from 2 to about 5, usually 2 or 3) receptor binding moieties ("rbm"'s) which may be the same or different. As discussed elsewhere herein, the receptor binding moiety is a ligand (or analog thereof) for a known receptor, such as are enumerated in Section V(C), and including FK506, FK520, rapamycin and analogs thereof which are capable of binding to an FKBP; as well as cyclosporins, tetracyclines, other antibiotics and macrolides and steroids which are capable of binding to respective receptors.

The linker is a bi- or multi-functional molecule capable of being covalently linked ("-") to two or more receptor binding moieties. Typically the linker would comprise up to about 40 atoms and may include nitrogen, oxygen and sulfur in addition to carbon and hydrogen. Illustrative linker moieties are disclosed in Section VI(A) and in the various Examples and include among others C1–C30 alkyl, alkylene, or arylalkyl groups which may be substituted or unsubstituted and may be straight-chain, branched or cyclic. For example, alkyl substituents are saturated straight-chain, cyclic or branched hydrocarbon moieties, preferably of one to about twelve carbon atoms, including methyl, ethyl, n-propyl, i-propyl, cyclopropyl, n-butyl, i-butyl, t-butyl, cyclobutyl, cyclopropylmethylene, pentyl, hexyl, heptyl, octyl and so forth, and may be optionally substituted with one or more substituents such as lower alkoxy, carboxy, amino (substituted or unsubstituted), phenyl, aryl, mercapto, halo (fluoro, chloro, bromo or iodo), azido or cyano.

These compounds may be prepared using commercially available materials and/or procedures known in the art. Engineered receptors for these compounds may be obtained as described infra. Compounds of particular interest are those which bind to a receptor with a Kd of less than $10^{-6}$, preferably less than about $10^{-7}$ and even more preferably, less than $10^{-8}$ M.

One subclass of oligomerizing agents of interest are those in which one or more of the receptor binding moieties is FK506, an FK506-type compound or a derivative thereof, wherein the receptor binding moieties are covalently attached to the linker moiety through the allyl group at C21 (using FK6 numbering) as per compound 5 or 13 in FIG. 9A, or through the cyclohexyl ring (C29–C34), e.g. through the C32 hydroxyl as per compounds 8, 16, 17 in FIG. 9B. Compounds of this class may be prepared by adaptation of methods disclosed herein, including in the examples which follow.

Figure 10:
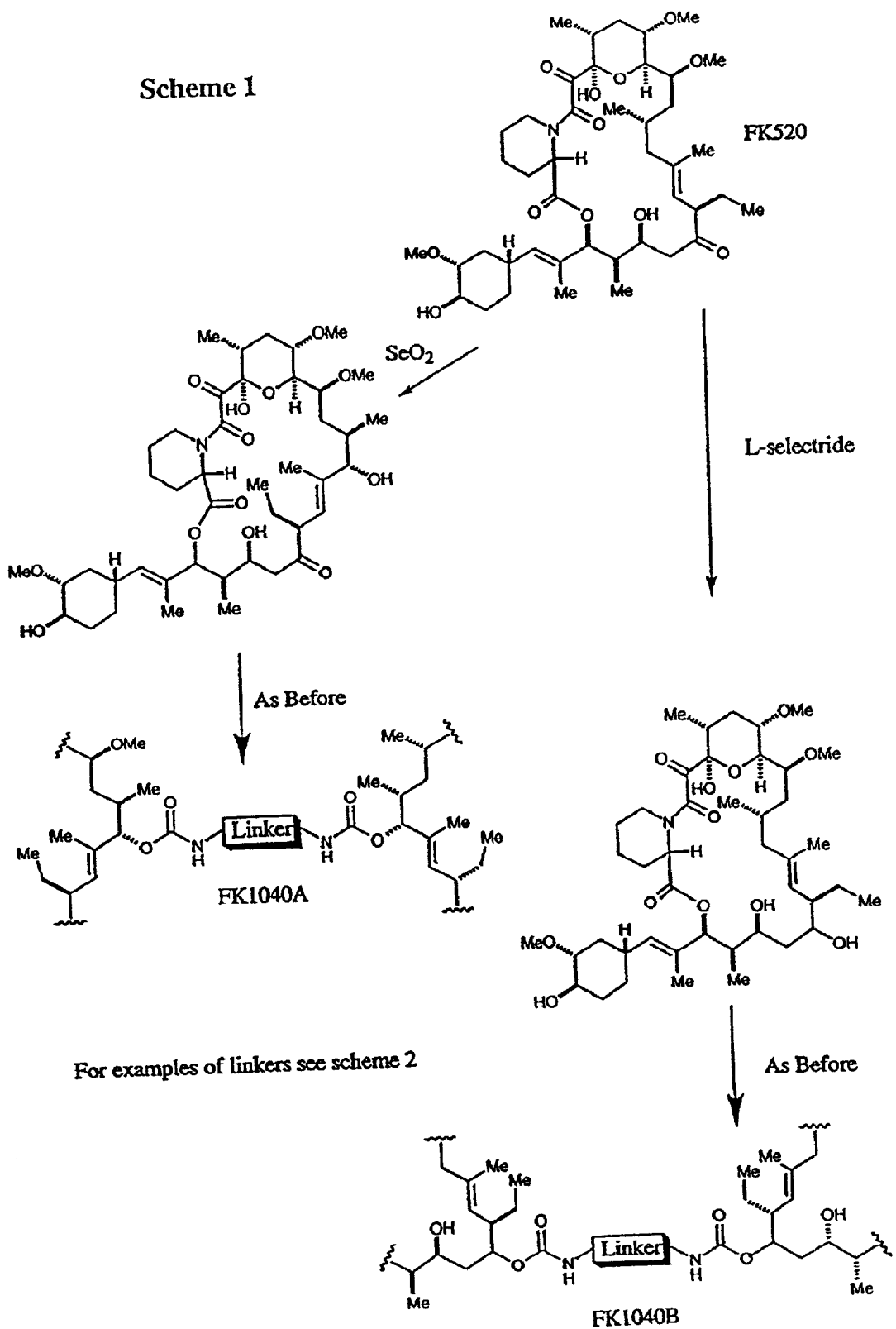
FIG. 10 is a flow diagram of the synthesis of derivatives of FK520.
Figure 12:
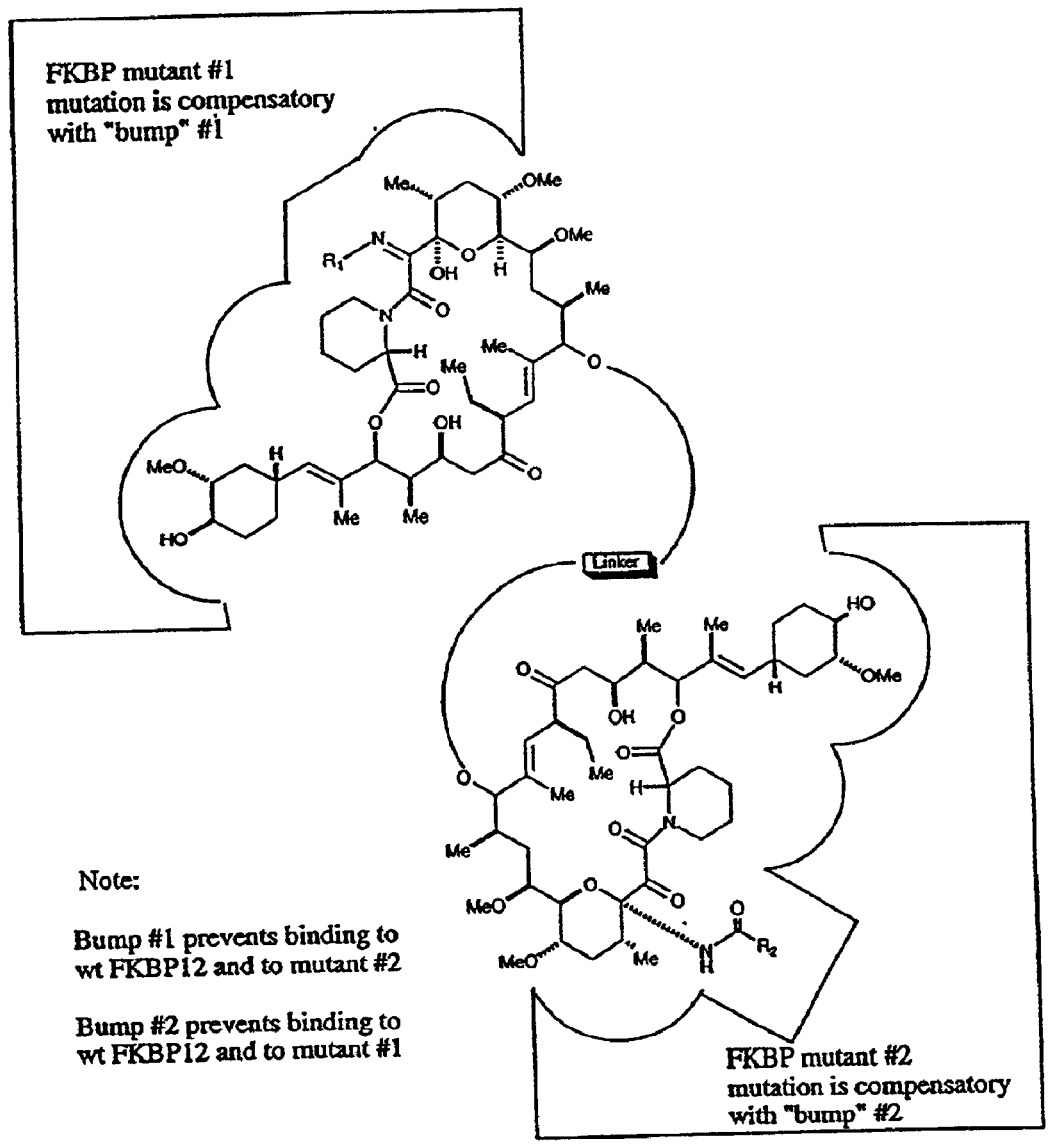
FIG. 12 is a diagrammatic depiction of mutant FKBP with a modified FK520 in the putative deft.

Another subclass of oligomerizing agents of interest are those in which at least one of the receptor binding moieties is FK520 or a derivative thereof, wherein the molecules of FK520 or derivatives thereof are covalently attached to the linker moiety as in FK1040A or FK1040B in FIG. 10. Compounds of this class may be prepared by adaptation of Scheme 1 in FIG. 10, Scheme 2 in FIGS. 11A and 11B or Scheme 3 in FIG. 12 and FIG. 13.

A further subclass of oligomerizing agents of interest are those in which at least one of the receptor binding moieties is cyclosporin A or a derivative.

It should be appreciated that these and other oligomerizing agents of this invention maybe homo-oligomerizing reagents (where the rbm's are the same) or hetero-oligomerizing agents (where the rbm's are different).

Figure 13:
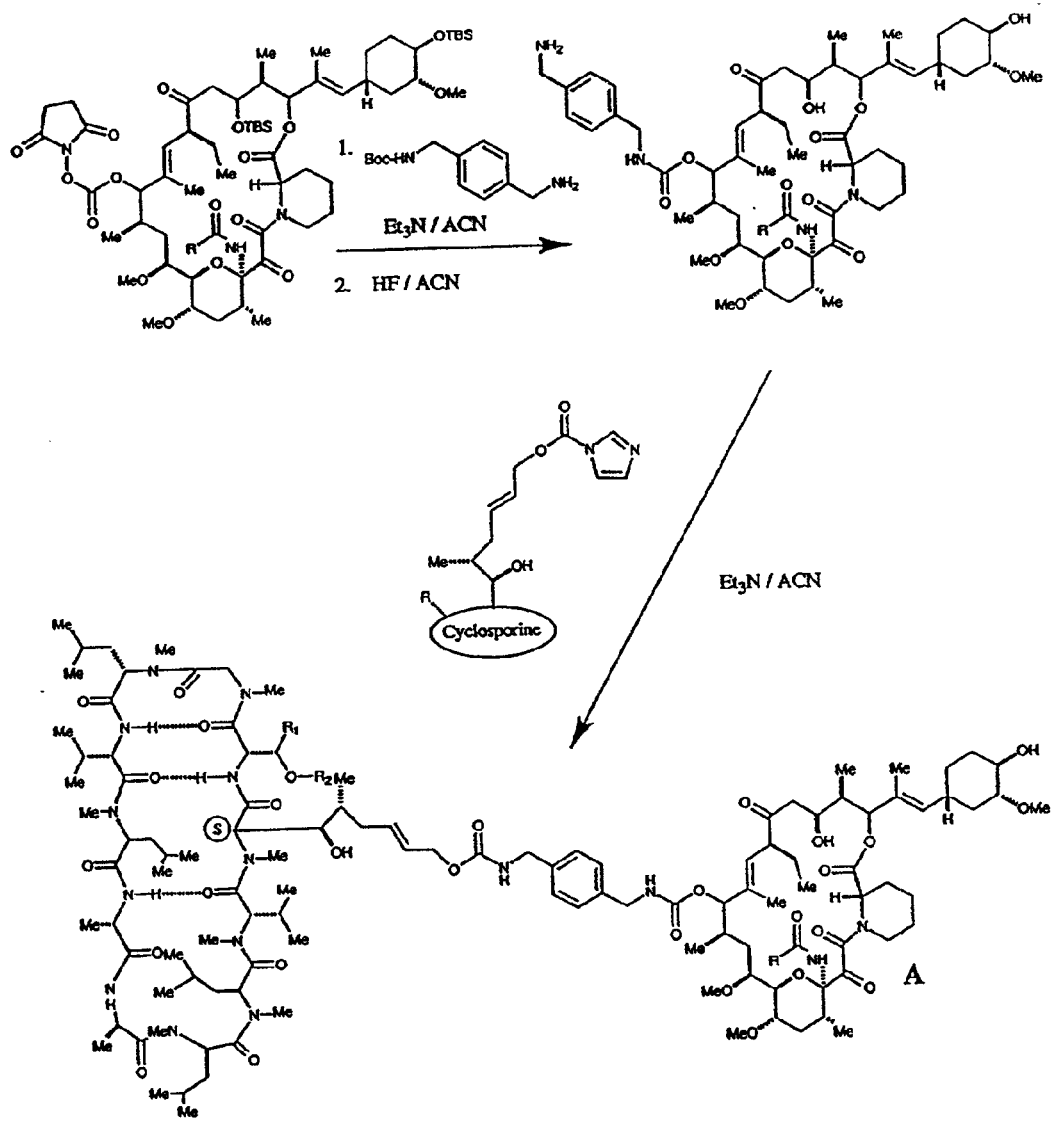
FIG. 13 is a flow diagram of the synthesis of heterodimers of FK520 and cyclosporin.

Hetero-oligomerizing agents may be prepared by analogy to the procedures presented herein, including Scheme 3 in FIG. 13 and as discussed elsewhere herein.

The following synthetic examples are intended to be illustrative.

A. General Procedures. All reactions were performed in oven-dried glassware under a positive pressure of nitrogen or argon. Air and moisture sensitive compounds were introduced via syringe or cannula through a rubber septum.

B. Physical Data. Proton magnetic resonance spectra ($^1$H NMR) were recorded on Bruker AM-500 (500 MHz), and AM-400 (400 MHz) spectrometers. Chemical shifts are reported in ppm from tetramethylsilane using the solvent resonance as an internal standard (chloroform, 727 ppm). Data are reported as follows: chemical shift, multiplicity (s=singlet, d=doublet, t=triplet, q=quartet, br=broadened, m=multiplet), coupling constants (Hz), integration. Low and high-resolution mass spectra were obtained.

C. Chromatography. Reactions were monitored by thin layer chromatography (TLC) using E. Merck silica gel 60F glass plates (0.25 mm). Components were visualized by illumination with long wave ultraviolet light, exposed to iodine vapor, and/or by dipping in an aqueous ceric ammonium molybdate solution followed by heating. Solvents for chromatography were HPLC grade. Liquid chromatography was performed using forced flow (flash chromatography) of the indicated solvent system on E. Merck silica gel 60 (230–400 mesh).

D. Solvents and Reagents. All reagents and solvents were analytical grade and were used as received with the following exceptions. Tetrahydrofuran (THF), benzene, toluene, and diethyl ether were distilled from sodium metal benzophenone ketyl. Triethylamine and acetonitrile were distilled from calcium hydride. Dichloromethane was distilled from phosphorous pentoxide. Dimethylformamide (DMF) was distilled from calcium hydride at reduced pressure and stored over 4A molecular sieves.

Preparation of FK506 Derivatives

Example 9

Hydroboration/Oxidation of FK506-TBS$_2$ (1 to 2).

The hydroboration was performed according to the procedure of Evans (Evans, et al., *JACS* (1992) 114, 6679; ibid. (1992) 6679–6685. (See Harding, et al., *Nature* (1989) 341, 758 for numbering.) A 10-ml flask was charged with 24,32-bis[(tert-butyldimethylsilyl)oxy]-FK506 (33.8 mg, 0.033 mmol) and [Rh(nbd)(diphos-4)]BF$_4$(3.1 mg, 0.004 mmol, 13 mol %). The orange mixture was dissolved in toluene (2.0 mL) and the solvent was removed under reduced pressure over four hours. The flask was carefully purged with nitrogen and the orangish oil was dissolved in THF (3.0 mL, 10 mM final concentration) and cooled to 0° C. with an ice water bath. Catecholborane (98 µL, 0.098 mmol, 1.0 M solution in THF, 3.0 equiv.) was added via syringe and the resulting solution was stirred at 0° C. for 45 min. The reaction was quenched at 0° C. with 0.2 mL of THF/EtOH (1:1) followed by 0.2 mL of pH 7.0 buffer (Fisher; 0.05 M phosphate) then 0.2 mL of 30% H$_2$O$_2$. The solution was stirred at room temperature for at least 12 h. The solvent was removed under reduced pressure and the remaining oil was dissolved in benzene (10 mL) and washed with saturated aqueous sodium bicarbonate solution (10 mL). The phases were separated and the aqueous phase was back-extracted with benzene (2×10 mL). The organic phases were combined and washed once with saturated aqueous sodium bicarbonate solution (10 mL). The benzene phase was dried with MgSO$_4$, concentrated, and subjected to flash chromatography (2.1 hexane:ethyl acetate) providing the desired primary alcohol as a clear, colorless oil (12.8 mg, 0.012 mmol, 37%).

Preparation of Mixed Carbonate (2 to 3). The preparation of the mixed carbonate was accomplished by the method of Ghosh (Ghosh, et al., *Tetrahedron Lett.* (1992) 33, 2781–2784). A 10-mL flask was charged with the primary alcohol (29.2 mg, 0.0278 mmol) and benzene (4 mL). The solvent was removed under reduced pressure over 60 min. The oil was dissolved in acetonitrile (2.0 mL, 14 mM final concentration) and stirred at 20° C. as triethylamine (77 µL, 0.56 mmol) was added. N,N'-disuccinimidyl carbonate (36 mg, 0.14 mmol) was added in one portion and the solution was stirred at 20° C. for 46 h. The reaction mixture was diluted with dichloromethane and washed with saturated aqueous sodium bicarbonate solution (10 mL). The phases were separated and the aqueous layer was back extracted with dichloromethane (2×10 mL). The organic phases were combined and dried (MgSO$_4$, concentrated, and subjected to flash chromatography (3:1 to 2:1 to 1:1 hexane:ethyl acetate). The desired mixed carbonate was isolated as a clear, colorless oil (16.8 mg, 0.014 mmol, 51%).

Dimerization of FK506 (3 to 4). A dry, 1-mL conical glass vial (Kontes Scientific Glassware) was charged with the mixed carbonate (7.3 mg, 0.0061 mmol) and acetonitrile (250 µL, 25 mM final concentration). Triethylamine (10 µL, 0.075 mmol) was added followed by p-xylylenediamine (83 µL, 0.0027 mmol, 0.32 M solution in DMF). The reaction stirred 22 h at 20° C. and was quenched by dilution with dichloromethane (10 mL). The solution was washed with saturated aqueous sodium bicarbonate solution (10 ml). The phases were separated and the aqueous layer was back-extracted with dichloromethane (2×10 mL). The organic phases were combined and dried (MgSO$_4$), concentrated, and subjected to flash chromatography (3:1 to 2:1 to 1:1 hexane:ethyl acetate) providing the desired protected dimer as a clear, colorless oil (4.3 mg, 1.9 µmol, 70%).

Deprotection of the FK506 Dimer (4 to 5). The protected dimer (33 mg, 1.4 µmol) was placed in a 1.5-mL polypropylene tube fitted with a spin vane. Acetonitrile (0.5 mL, 3 mM final concentration) was added and the solution stirred at 20° C. as HF (55 µL, 48% aqueous solution; Fisher) was added. The solution was stirred 18 h at room temperature. The deprotected FK506 derivative was then partitioned between dichloromethane and saturated aqueous sodium bicarbonate in a 15-mL test tube. The tube was vortexed extensively to mix the phases and, after separation, the organic phase was removed with a pipet. The aqueous phase was back-extracted with dichloro-methane (4×2 mL), and the combined organic phases were dried (MgSO$_4$), concentrated and subjected to flash chromatography (1:1:1 hexane:THF:ether to 1:1 THF:ether) providing the desired dimer as a clear, colorless oil (1.7 mg, 0.93 µmol, 65%).

Following the above procedure, other monoamines and diamines may be used, such as benzylamine (14) octamethylenediamine, decamethylenediamine, etc.

Example 10

Reduction of FKS506 with L-Selectride (FK506 to 6)

Danishefsky and coworkers have shown that the treatment of FK506 with L-Selectride provides 22-dihydro-FK506 with a boronate ester engaging the C24 and C22 hydroxyl groups (Coleman and Danishefsky, *Heterocycles* (1989) 28, 157–161; Fisher, et al., *J. Org. Chem.* (1991) 56, 2900–2907).

Preparation of the Mixed Carbonate (6 to 7). A 10-mL flask was charged with 22-dihydro-FK506-sec-butylboronate (1253 mg, 0.144 mmol) and acetonitrile (3.0 mL, 50 mM final concentration) and stirred at room temperature as triethylamine (200 µL, 1.44 mmol, 10 equiv.) was added to the clear solution. N,N'-disuccinimidyl carbonate (184.0 mg, 0.719 mmol) was added in one portion, and the clear solution was stirred at room temperature for 44 h. The solution was diluted with ethyl acetate (20 mL) and washed with saturated aqueous sodium bicarbonate (10 mL) and the phases were separated. The aqueous phase was then back extracted with ethyl acetate (2×10 mL), and the organic phases were combined, dried ($MgSO_4$), and the resulting oil was subjected to flash chromatography (1:1 to 1:2 hexane:ethyl acetate) providing the desired mixed carbonate as a clear, colorless oil (89.0 mg, 0.088 mmol, 61%).

Dimerization of FK506 Mixed Carbonate (7 to 8). A dry, 1-mL conical glass vial (Kontes Scientific Glassware) was charged with the mixed carbonate (15.0 mg, 0.0148 mmol) and dichloromethane (500 µL, 30 mM final concentration). The solution was stirred at room temperature as triethylamine (9 µL, 0.067 mmol, 10 equiv.) was added followed by p-xylylenediamine (0.8 mg, 0.0059 mmol). The reaction stirred 16 h at 20° C. and was quenched by dilution with dichloromethane (5 mL). The solution was washed with saturated aqueous sodium bicarbonate solution (5 mL). The phases were separated and the aqueous layer was back extracted with dichloromethane (2×5 mL). The organic phases were combined and dried ($MgSO_4$), concentration, and subjected to flash chromatography (1:1 to 1:2 hexane:ethyl acetate) providing the desired dimer as a clear, colorless oil (7.4 mg, 3.8 µmol, 65%).

Following the above procedure, other, monoamines, diamines or triamines may be used in place of the xylylenediamine, such as benzylamine (15), octylenediamine, decamethylenediamine (16), bis-p-dibenzylamine, N-methyl diethyleneamine, tris-aminoethylamine (17), tris-aminopropylamine, 1,3,5-triaminomethylcyclohexane, etc.

Example 11

Oxidative Cleavage and Reduction of FK506 (1 to 9)

The osmylation was performed according to the procedure of Kelly (VanRheenen, et al., Tetrahedron Lett. (1976) 17, 1973–1976). The cleavage was performed according to the procedure of Danishefsky (Zell, et al., J. Org. Chem. (1986) 51, 5032–5036). The aldehyde reduction was performed according to the procedure of Krishnamurthy (J. Org. Chem., (1981) 46, 4628–4691). A 10 mL flask was charged with 24,32-bis[tert-butyldimethylsilyl)oxy]-FK506 (84.4 mg, 0.082 mmol), 4-methylmorpholine N-oxide (48 mg, 0.41 mmol, 5 equiv), and THF (2.0 mL, 41 mM final concentration). Osmium tetroxide (45 µL, 0.008 mmol 0.1 equiv) was added via syringe. The clear, colorless solution was stirred at room temperature for 5 hr. The reaction was then diluted with 50% aqueous methanol (1.0 mL) and sodium periodate (175 mg, 0.82 mmol, 10 equiv) was added in one portion. The cloudy mixture was stirred 40 min at room temperature, diluted with ether (10 mL), and washed with saturated aqueous sodium bicarbonate solution (5 mL). The phases were separated and the aqueous layer was back-extracted with ether (2×5 mL). The combined organic layers were dried ($MgSO_4$) and treated with solid sodium sulfite (50 mg). The organic phase was then filtered and concentrated and the oil was subjected to flash chromatography (3:1 to 2:1 hexane:ethyl acetate) providing the intermediate, unstable aldehyde (53.6 mg) as a clear, colorless oil. The aldehyde was immediately dissolved in THF (4.0 mL) and cooled to −78° C. under an atmosphere of nitrogen, and treated with lithium tris[(3-ethyl-3-pentyl)oxy]aluminium hydride (0.60 mL, 0.082 mmol, 0.14 M solution in THF, 1.0 equiv). The clear solution was allowed to stir for 10 nun at −78° C. then quenched by dilution with ether (4 mL) and addition of saturated aqueous ammonium chloride (0.3 mL). The mixture was allowed to warm to room temperature and solid sodium sulfate was added to dry the solution. The mixture was then filtered and concentrated and the resulting oil was subjected to flash chromatography (2:1 hexane:ethyl acetate) giving the desired alcohol as a clear, colorless oil (39.5 mg, 0.038 mmol, 47%).

Preparation of Mixed Carbonate (9 to 10). The preparation of the mixed carbonate was accomplished by the method of Ghosh, et al., Tetrahedron Lett. (1992) 33, 2781–2784). A 10 mL flask was charged with the primary alcohol (38.2 mg, 0.0369 mmol) and acetonitrile (2.0 mL, 10 mM final concentration) and stirred at room temperature as 2,6-lutidine (43 µL, 0.37 mmol, 10 equiv) was added. N,N'-disuccinimidyl carbonate (48 mg, 0.18 mmol) was added in one portion and the solution was stirred at room temperature for 24 h. The reaction mixture was diluted with ether (10 mL) and washed with saturated aqueous sodium bicarbonate solution (10 mL). The phases were separated and the aqueous layer was back-extracted with ether (2×10 mL). The organic phases were combined and dried ($MgSO_4$), concentrated, and subjected to flash chromatography (2:1 to 1:1 hexane:ethyl acetate). The desired mixed carbonate was isolated as a clear, colorless oil (32.6 mg, 0.028 mmol, 75%).

Preparation of Benzyl Carbamate (10 to 11). A dry, 1 mL conical glass vial (Kontes Scientific Glassware) was charged with the mixed carbonate 10 (8.7 mg, 0.0074 mmol) and acetonitrile (500 µL, 15 mM final concentration). The solution was stirred at room temperature as triethylamine (10 µL, 0.074 mmol, 10 equiv) was added followed by benzylamine (1.6 µL, 0.015 mmol 2 equiv). The reaction stirred 4 h at room temperature. The solvent was removed with a stream of dry nitrogen and the oil was directly subjected to flash chromatography (3:1 to 2:1 hexane:ethyl acetate) providing the desired protected monomer as a clear, colorless oil (6.2 mg, 5.3 µmol, 72%).

The protected monomer (6.2 mg, 5.3 µmol) was placed in a 1.5 mL polypropylene tube fitted with a spin vane. Acetonitrile (0.5 mL, 11 mM final concentration) was added and the solution stirred at room temperature as HF (55 µL, 48% aqueous solution; Fisher, 3.0 N final concentration) was added. The solution was stirred 18 h at room temperature. The deprotected FK506 derivative was then partitioned between dichloromethane and saturated aqueous sodium bicarbonate in a 15 mL test tube. The tube was vortexed extensively to mix the phases and, after separation, the organic phase was removed with a pipes. The aqueous phase was back-extracted with dichloromethane (4×2 mL), and the combined organic phases were dried ($MgSO_4$), concentrated and subjected to flash chromatography (1:1 to 0:1 hexane:ethyl acetate) providing the desired deprotected benzylcarbamate as a clear, colorless oil (3.9 mg, 4.1 µmol, 78%).

By replacing the benzylamine with a diamine such as xylylenediamine (12), hexamethylenediamine, octamethylenediamine, decamethylenediamine (13) or other diamines, dimeric compounds of the subject invention are prepared.

Example 12

Preparation of the Mixed Carbonate of FK506 (12)

A 10-mL flask was charged with 24,32-bis [(tert-butyldimethylsilyl)oxy]-FK506 (339.5 mg., 0.329 mmol), 4-methylmorpholine N-oxide (193 mg, 1.64 mmol, 5 equiv), water (0.20 mL) and THF (8.0 mL, 41 mN final concentration). Osmium tetroxide (0.183 mL, 0.033 mmol, 0.1 equiv, 0.18 M soln in water) was added via syringe. The clear, colorless solution was stirred at room temperature for 4.5 h. The reaction was diluted with 50% aqueous methonol (4.0 mL) and sodium periodate (700 mg, 3.29 mmol, 10 equiv) was added in one portion. The cloudy mixture was stirred 25 min at room temperature, diluted with ether (20 mL), and washed with saturated aqueous sodium bicarbonate solution (10 mL). The phases were separated and the aqueous layer was back extracted with ether (2×10 mL). The combined organic layers were dried over $MgSO_4$ and solid sodium sulfite (50 mg). The organic phase was then filtered and concentrated and the resulting aldehyde was immediately dissolved in THF (8.0 mL) and cooled to −78° C. under an atmosphere of nitrogen, and treated with lithium tris [(3-ethyl-3-pentyl)oxy]aluminum hydride (2.35 mL, 0.329 mmol, 0.14 M solution of THF, 1.0 equiv). The clear solution was allowed to stir for 60 min at −78° C. (monitored closely by TLC) then quenched at −78° C. by dilution with ether (5 mL) and addition of saturated aqueous ammonium chloride (0.3 mL). The mixture was allowed to warm to room temperature and solid sodium sulfate was added to dry the solution. The mixture was stirred 20 min, filtered, concentrated, and the resulting oil was immediately dissolved in acetonitrile (10 mL). To the solution of the resulting primary alcohol in $CH_3CN$ was added 2,6-lutidine (0.380 mL, 3.3 mmol, 10 equiv) and N,N'-disuccinimidyl carbonate (420 mg, 1.65 mmol, 5 equiv). The heterogenous mixture was stirred at room temperature for 19 h, at which time the solution was diluted with ether (30 mL) and washed with saturated aqueous sodium bicarbonate (20 mL). The aqueous phase was back-extracted with ether (2×10 mL). The organic phases were combined and dried ($MgSO_4$), concentrated, and subjected to flash chromatography (3:1 to 2:1 to 1:1 hexane/ethyl acetate). The desired mixed carbonate 12 was isolated as a clear, colorless oil (217 mg, 0.184 mmol, 56% overall for 4 steps).

Example 13

Preparation of 24,24',32,32'-tetrakis [(tert-butyldimethylsilyl)oxy]-FK1012-A (p-xylylenediamine bridge)

A dry, 1-mL conical glass vial was charged with the mixed carbonate (23.9 mg, 0.0203 mmol) and acetonitile (500 µL, 41 mM final concentration). Triethylamine (28 µL, 0.20 mmol, 10 equiv) was added followed by p-xylylenediamine (46 µL, 0.0101 mmol, 0.22 M solution in DMF). The reaction stirred 18 h at room temperature, the solvent was removed with a stream of dry nitrogen, and the oil was directly subjected to flash chromatography (3:1 to 2:1 to 1:1 hexane/ethyl acetate) affording the desired protected dimer as a clear, colorless oil (11.9 mg, 53 µmol, 52%).

Example 14

Preparation of FK1012-A (p-xylylenediamine bridge) (13)

The protected dimer (11.0 mg, 4.9 µmol) was placed in a 1.5-mL polypropylene tube fitted with a spin vane. Acetonitrile (0.50 mL, 10 mM final concentration) was added, and the solution stirred at 20° C. as HF (55 µL, 48% aqueous solution; Fisher, 3.0 N final concentration) was added. The solution was stirred 16 h at room temperature. The deprotected FK506 derivative was then partitioned between dichloromethane and saturated aqueous sodium bicarbonate in a 15-mL test tube. The tube was vortexed extensively to mix the phases and, after separation, the organic phase was removed with a pipet. The aqueous phase was back-extracted with dichloromethane (4×2 mL), and the combined organic phases were dried ($MgSO_4$), concentrated and subjected to flash chromatography (1:1:1 hexane/THF/ether to 1:1 THF/ether) providing FK1012-A as a clear, colorless oil (5.5 mg, 3.0 µmol, 63%).

Example 15

Preparation of 24,24',32,32'-tetrakis[(terbutyldimethylsilyl)oxy]-FK1012-B (diaminodecane bridge)

A dry, 1-mL conical glass vial was charged with the mixed carbonate (53.3 mg, 0.0453 mmol) and acetonitrile (2.0 mL, 11 m M final concentration). Triethylamine (16 µL, 0.11 mmol, 5 equiv) was added followed by diaminodecane (61 µL, 0.0226 mmol, 0.37 M solution in DMF). The reaction stirred 12 h at room temperature, the solvent was removed with a stream of dry nitrogen, and the oil was directly subjected to flash chromatography (3:1 to 2:1 to 1:1 hexane/ethyl acetate) affording the desired protected dimer as a clear, colorless oil (18.0 mg, 7.8 µmol, 35%).

Example 16

Preparation of FK1012-B (diaminodecane-1,10 bridge) (14)

The protected dimer (180 mg, 7.8 µmol) was placed in a 1.5-mL polypropylene tube fitted with a stirring flea. Acetonitrile (0.45 mL, 16 mM final concentration) was added, and the solution stirred at room temperature as HF (55 µL, 48% aqueous solution; Fisher, 3.6 N final concentration) was added. The solution was stirred 17 h at 23° C. The product FK1012-B was then partitioned between dichloromethane and saturated aqueous sodium bicarbonate in a 15-mL test tube. The tube was vortexed extensively to mix the phases and, after separation, the organic phase was removed with a pipet. The aqueous phase was back-extracted with dichloromethane (4×2 mL), and the combined organic phases were dried ($MgSO_4$, concentrated and subjected to flash chromatography (100% ethyl acetate to 20:1 ethyl acetate/methanol) affording FK1012-B as a clear, colorless oil (5.3 mg, 2.9 µmol 37%).

Example 17

Preparation of 24,24',32,32'-tetrakis[(tert-butyldimethylsilyl)oxy]-FK1012-C (bis-p-aminomethylbenzoyl diaminodecane bridge)

A dry 25-mL tear-shaped flask was charged with the diamine linker (15.1 mg, 0.0344 mmol) and 1.0 mL of DMF. In a separate flask, the mixed carbonate and triethylamine (0.100 mL, 0.700 mmol, 20 equiv) were dissolved in 2.0 mL of dichloromethane then added slowly (4×0.5 mL) to the stirring solution of bis-p-aminomethylbenzoyl, diaminodecane-1,10. The flask containing the mixed carbonate 12 was washed with dichloromethane (2×0.50 mL) to ensure complete transfer of the mixed carbonate 12. The reaction stirred 16 h at 23° C., the solvent was removed with a stream of dry nitrogen, and the oil was directly subjected to flash chromatography (1:1 to 1:2 hexane/ethyl acetate) to afford the desired protected dimer as a clear, colorless oil (29.6 mg, 11.5 µmol, 34%).

Example 18

Preparation of FK1012-C (15)

The protected dimer (29.6 mg, 11.5 μmol) (17) was placed in a 1.5-mL polypropylene tube fitted with a stirring flea. Acetonitrile (0.45 mL, 23 mM final concentration) was added, and the solution stirred at room temperature as HF (55 μL, 48% aqueous solution; Fisher, 3.6 N final concentration) was added. The solution was stirred 17 h at room temperature. The desired symmetrical dimer was then partitioned between dichloromethane and saturated aqueous sodium bicarbonate in a 15-mL test tube. The tube was vortexed extensively to mix the phases and, after separation, the organic phase was removed with a pipet. The aqueous phase was back-extracted with dichloromethane (4×2 mL), and the combined organic phases were dried ($MgSO_4$), concentrated and subjected to flash chromatography (100% ethyl acetate to 15:1 ethyl acetate/methanol) affording FK1012-C as a clear, colorless oil (11.5 mg, 5.5 μmol, 47%).
Preparation of CsA Derivatives

Example 19

MeBmt(OAc)--$OH^1$CsA (2)

MeBmt(OAc)--$OAc^1$-CsA (1) (161 mg, 124 mmol) (see Eberle and Nuninger, *J. Org. Chem.* (1992) 57, 2689) was dissolved in Methanol (10 mL). KOH (196 mg) was dissolved in water (8 mL). 297 μL of the KOH solution (0.130 mmol, 1.05 eq.) was added to the solution of (1) in MeOH. This new solution was stirred at room temperature under an inert atmosphere for 4 hours at which time the reaction was quenched with acetic acid (2 mL). The reaction mixture was purified by reversed phase HPLC using a 5 cm×25 cm, 12μ, 100 A, C18 column at 70° C. eluting with 70% acetonitrile/$H_2O$ containing 0.1% (v/v) Trifluoroacetic add to give 112 mg (72%) of the desired monoacetate (2).

MeBmt(OAc)--$OCl-m^1$CsA (3). MeBmt(OAc)--$OH^1$-CsA (2) (57 mg, 45.5 μmol) and carbonyldiimidazole (15 mg, 2 eq., 91 μmol) were transferred into a 50 mL round bottom flask and dissolved in dry THF (6 mL). Diisopropylethylamine (32 μL, 4 eq., 182 μmol) was added and then the solvent was removed on a rotary evaporator at room temperatures. The residue was purified by flash chromatography on silica gel using ethylacetate as eluent to give 45 mg (73%) of the desired carbamate (3).

Tris-(2-aminoethyl)amine CsA Triacetate (6). MeBmt (OAc)--$OCOIm^1$-CsA (3) (7.5 mg, 5.54 μmol, 3.1 eq.) was dissolved in THF (100 μL). Diisopropylethylamine (62 μL, 5 eq., 8.93 μmol of a solution containing 100 μL of amine in 4 mL THF) was added followed by tris(2-aminoethyl)amine (26 μL, 1.79 μmol, 1 eq. of a solution containing 101 mg of tris-amine in 10 mL THF). This solution was allowed to stir under $N_2$ atmosphere for 5 days. The reaction mix was evaporated and then purified by flash chromatography on silica gel using 0–5% methanol in chloroform to give 4.1 mg of desired product (6).

Example 20

Diaminodecane CsA Dimer (8)

Solid Na metal (200 mg excess) was reacted with dry methanol (10 mL) at 0° C. Diaminodecane CsA Dimer Diacetate (5) (4.0 mg) was dissolved in MeOH (5 mL). 2.5 mL of the NaOMe solution was added to the solution of (5). After 2.5 hours of stirring at room temperature under an inert atmosphere, the solution was quenched with acetic acid (2 mL) and the product was purified by reversed phase HPLC using a 5 mm×25 mm, 12μ, 100 A, C18 column at 70° C. eluting with 70–95% acetonitrile/$H_2O$ over 20 minutes containing 0.1% (v/v) Trifluoroacetic add to give 2.5 mg (60%) of the desired diol.

The diaminodecane CsA Dimer Diacetate (5) was prepared by replacing the tris(2-aminoethyl)amine with 0.45 eq. of 1,10-diaminodecane.

Example 21 p-Xylylenediamine CsA Dimer (4)

The p-xylene diamine CsA Dimer (4) was prepared by replacing the tris(2-aminoethyl)amino with 0.45 eq. of p-xylylene diamine.

Following procedures described in the literature other derivatives of cyclophilin are prepared by linking at a site other than the 1(MeBmt 1) site.

Position 8 D-isomer analogues are produced by feeding the producing organism with the D-amino analogue to obtain incorporation specifically at that site. See Patchett et al., *J. Antibiotics* (1992) 45, 943 (β-MeSO)D-$Ala^8$-CsA); Traber, et al., ibid. (1989) 42, 591). The position 3 analogues are prepared by poly-lithiation/alkylation of CsA, specifically at the carbon of Sac3. See Wenger, *Transplant Proceeding* (1986) 18, 213, supp. 5 (for cyclophilin binding and activity profiles, particularly D-$MePhe^3$-CsA); Seebach, U.S. Pat. No. 4,703,033, issued Oct. 27, 1987 (for preparation of derivatives).

Instead of cyclosporin A, following the above-described procedures, other naturally-occurring variants of CsA may be multimerized for use in the subject invention.

Example 21A

Alternative Synthesis for CsA Dimer

MeBmt(OH)-η-$OCOIm^1$-CsA

MeBmt(OH)-η-$OH^1$-CsA (38 mg, 31 μmol, 1218.6 g/mol) and carbonyldiimidazole (20 mg, 4 eq., 124 μmol, 162.15 g/mol) were transferred into a 10 mL round bottom flask and dissolved in dry THF (2 mL). Diisopropylethylamine (22 μL, 4 eq., 125 μmol, 129.25 g/mol) was added and then the solvent was removed on a rotary evaporator at room temperature. The residue was purified by flash chromatography on silica gel using 0–20% acetone in ethyl acetate as eluent to give 32 mg (78% yield) of a white solid.

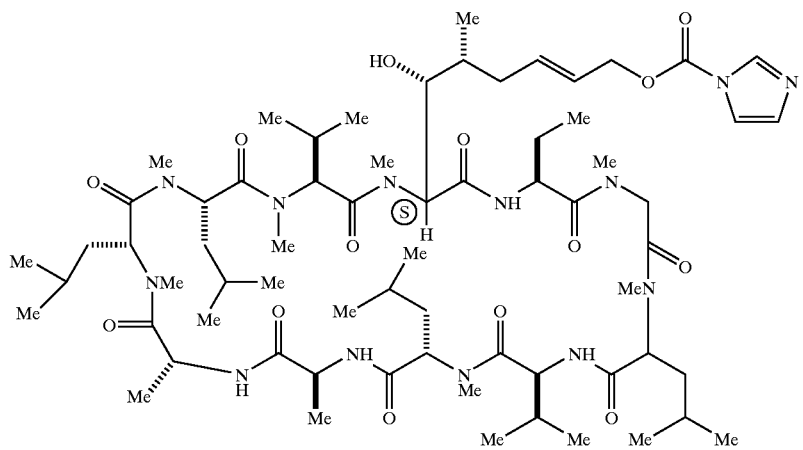

(CsA)2 Xylylenediamine CsA Dimer

MeBmt(OH)-η-OCOIm[1]-CsA (12.5 mg, 9.52 μmol, 1312.7 g/mol) was dissolved in DCM (200 μL). To this solution was added 22 μl (0.5 eq., 4.75 μmol) of a solution of xylylene diamine (14.7 mg, 136.2 g/mol) in DMSO (0.5 mL) and the reaction mixture was stirred for 72 hours at room temperature under a nitrogen atmosphere concentrating slowly. The reaction was diluted with acetonitrile (2 mL) filtered through glass wool and purified by reverse phase HPLC (Beckman C18, 10μ, 100 A, 1 cm×25 cm, 5 mL/min, 50 to 90% ACN/H$_2$O(+0.1% TFA) over 30 minutes, 70° C.) to give 6.1 mg (49% yield) of a white solid.

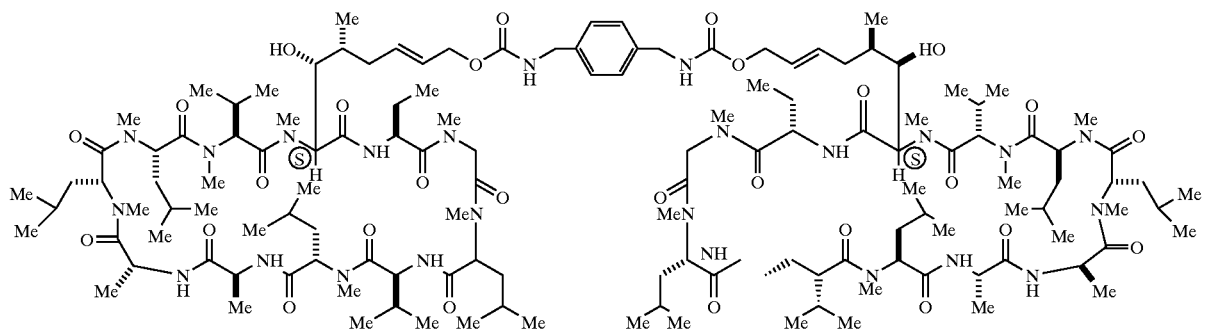

Example 21B

Synthesis of a FK506-CsA Dimer
MeBmt(OAc)-η-CH$_2$COOEt-CsA

MeBmt(OAc)-η-Br[1]-CsA (26 mg, ~80% pure, 15.7 μmol, 1323.57 g/mol) was dissolved in THF (500 μL). This solution was added by syringe pump over 15 hours to a THF solution of the magnesium enolate of ethyl hydrogen malonate (excess) prepared by the addition of iPrMgCl (2.15 mL, 2.34 M in ether) to a 0° C. solution of ethyl hydrogen malonate (Lancaster, 2.5 mmol, 332 mg, 132.12 g/mol) in THF (4.7 mL) followed by warming to room temperature. The reaction mixture was quenched with 1N HCL (50 mL) and extracted with ethyl acetate (2×50 mL). The organic layers were dried over Na$_2$SO$_4$, filtered and evaporated.

The crude product was dissolved in DMF (1 mL). Et$_4$NOAc.4H$_2$O (150 mg, excess) was added and the mixture was heated at 90° C. for 2 hours. The reaction mixture was cooled to room temperature, diluted with H$_2$O (50 mL)

and extracted with ether (2×50 mL). The combined organics were dried over Na2SO4, filtered and evaporated. The residue was purified by flash chromatography on silica gel, eluting with 75–100% ethyl acetate/hexanes to give 11.4 mg (55%) of a white solid.

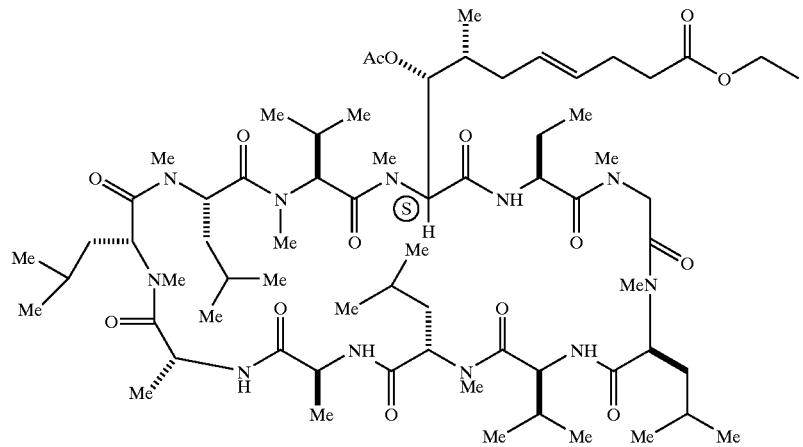

MeBmt(OH)-η-CH$_2$COOH$^1$-CsA

MeBmt(OAc)-η-CH$_2$COOEt$^1$-CsA (11.0 mg, 8.27 μmol, 1330.76 gl/mol) was dissolved in MeOH (2 mL) and added to a solution of NaOMe (1.30 M in MeOH, 10 mL). The reaction mixture was stirred at room temperature under a nitrogen atmosphere for 5 hours at which time H$_2$O (2 mL) was added and the mixture was stirred for another 2 hours. The reaction was quenched with glacial acetic acid (1 mL), filtered through glass wool and purified by reverse phase HPLC (Rainin C18 dynamax, 5μ, 300 A, 21.4 mm×250 mm, 20 mL/min, 50 to 90% ACN/H$_2$O (+0.1% TFA) over 30 minutes, 70° C.) to give 5.5 mg (53% yiel) of a white solid.

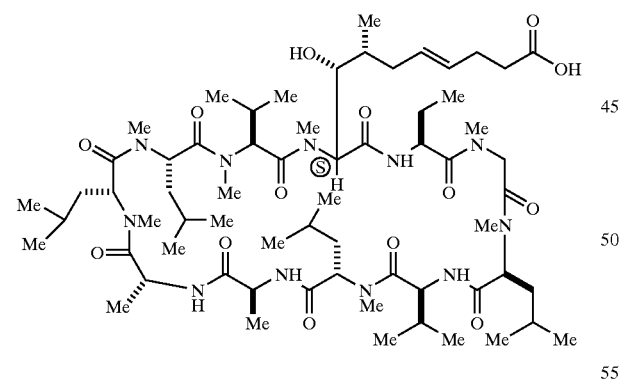

bis-TBS-N-(6-(Boc-amino)hexyl) FKS506 Carbamate bis-TBS-FKS506 succinimidyl carbonate (also a precursor to (tbs)4-FK1012) (5.8 mg, 1177.62 g/mol, 4.93 μmol) was dissolved in DCM. To this was added N-Boc-1,6-diaminohexane (7.25 mg, excess). After stirring for 10 min at room temperature the reaction mixture was evaporated and the product purified by flash chromatography eluting with 10 to 40% ethyl acetate/hexanes to provide 5.9 mg (94% yield).

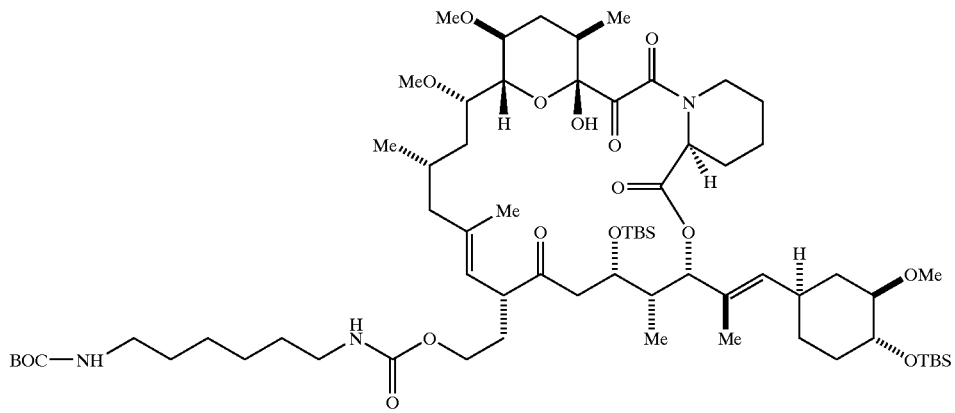

N-(6-aminohexyl) FKS506 Carbamate bis-TBS-N-(6(Boc-amino)hexyl) FK506 carbamate (59 mg, 1278.88 g/mol, 4.61 μmol) was transfered to a polypropylene tube in ACN (700 μl) followed by aqueous HF (49%, 100 μL). The reaction was complete after six hours at room temperature and was quenched by the slow addition of a saturated solution of NaHCO$_3$. The mixture was diluted with saturated NaHCO$_3$ (4 mL), H2O (4 mL) and extracted with DCM (3×10 mL). The combined organic phases were dried with MgSO$_4$, filtered and evaporated to give 3.6 mg (82% yield) of crude product.

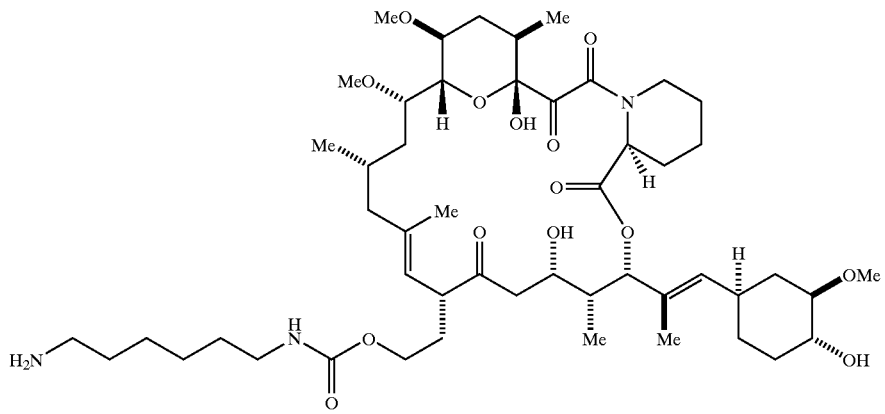

FKCsA

MeBmt(OH)-η-CH$_2$COOH$^1$-CsA (2.86 mg, 2.27 μmol, 1260.66 g/mol) and N-(6-aminohexyl) FK506 carbamate (crude, 2.16 mg, 2.28 μmol, 949.21 g/mol) were dissolved in DCM (900 μL). To this solution was added 127 μl (3.0 eq., 6.8 μmol) of a solution of BOP (11.9 mg, 442.5 g/mol) in DCM (500 μL), followed by 45 μL (2.25 eq., 5.1 μmol) of a solution of diisopropylethyl amine (20 μL, d=0.74 2129.25 g/mol) in DCM (1.0 mL). Finally DMF (40 μL) was added and the reaction mixture was evaporated slowly at room temperature under a stream of nitrogen over 12 hours. The reaction mixture was diluted with acetonitrile (1 mL) filtered through glass wool and purified by reverse phase HPLC (Beckman C18, 1 cm×25 cm, 5 mL/min, 50 to 90% ACN/ H$_2$O over 25 minutes, 50° C.) to give 2.4 mg (48% yield) of a white solid.

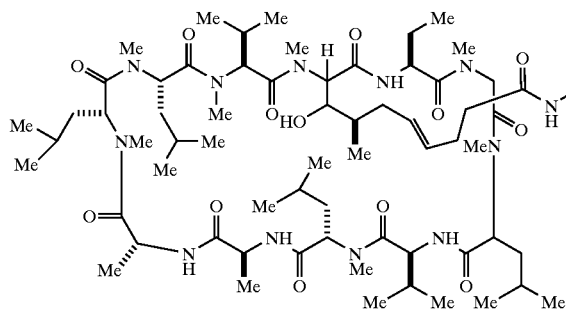
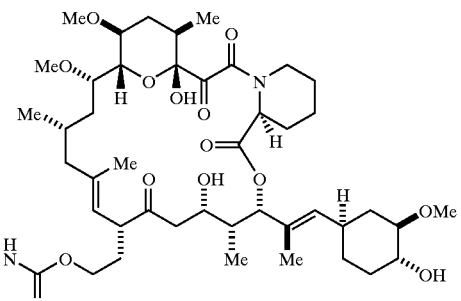

Example 22

Figure 21:
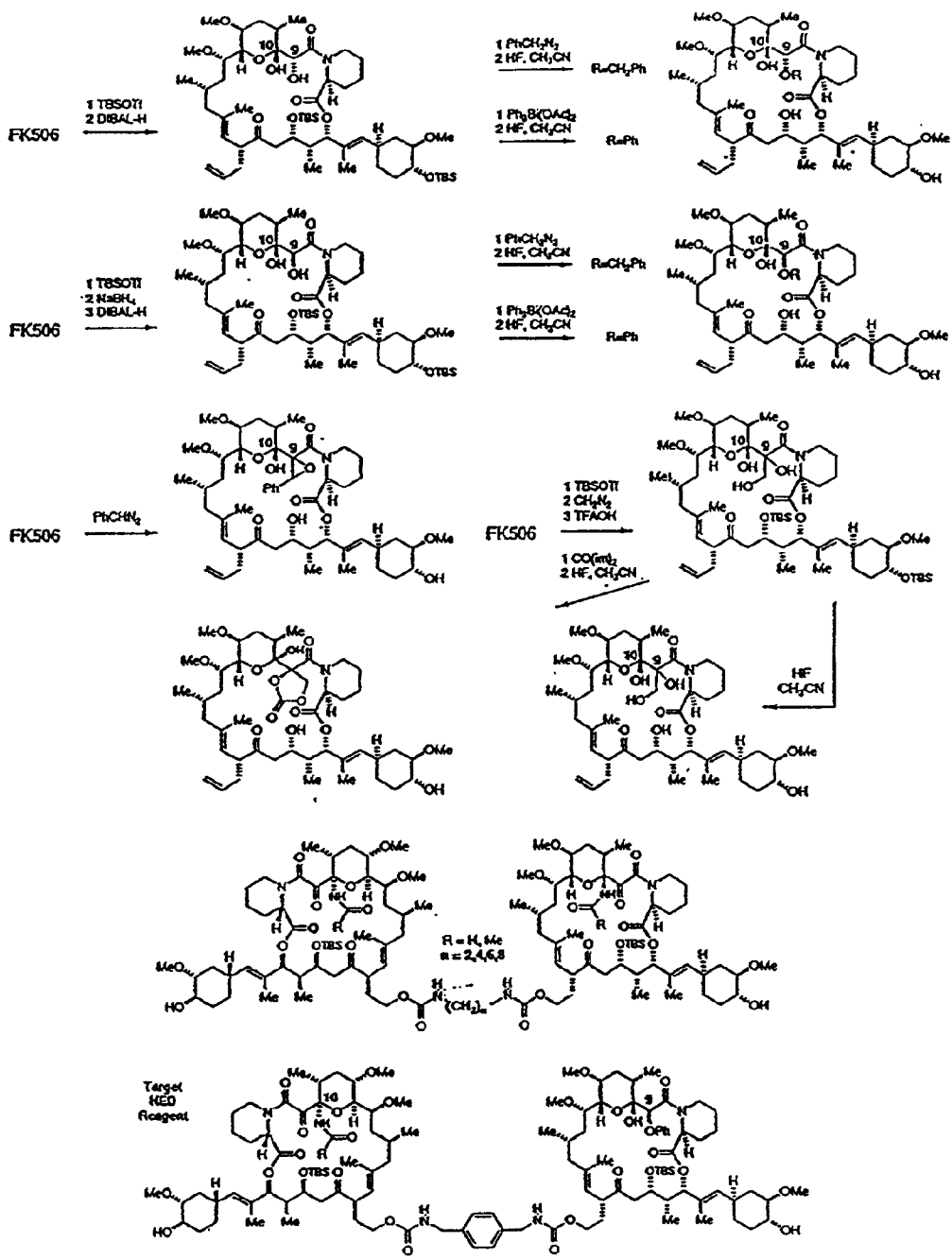
FIG. 21 depicts the synthesis of modified FK506 type compounds.

(A) Structure-Based Design and Synthesis of FK1012-"Bump" Compounds and FKBP12s with Compensatory Mutations Substituents at C9 and C10 of FK506, which can be and have been accessed by synthesis, clash with a distinct set of FKBP12 sidechain residues. Thus, one class of mutant receptors for such ligands should contain distinct modifications, one creating a compensatory hole for the C10 substituent and one for the C9 substituent. Carbon 10 was selectively modified to have either an N-acetyl or N-formyl group projecting from the carbon (vs. a hydroxyl group in FK506). The binding properties of these derivatives clearly reveal that these C10 bumps effectively abrogate binding to the native FKBP12. FIG. 21 depicts syntheses of FK506-type moieties containing additional C9 bumps. By assembling such ligands with linker moieties of this invention one can construct HED and HOD (and antagonist) reagents for chimeric proteins containing corresponding binding domains bearing compensatory mutations. An illustrative HED reagent is depicted in FIG. 21 that contains modifications at C9 and C10.

This invention thus encompasses a class of FK506-type compounds comprising an FK506-type moiety which contains, at one or both of C9 and C10, a functional group comprising —OR, —R, —(CO)OR, —NH(CO)H or —NH(CO)R, where R is substituted or unsubstituted, alkyl or arylalkyl which may be straight-chain, branched or cyclic, including substituted or unsubstituted peroxides, and carbonates. "FK506-type moieties" include FK506, FK520 and synthetic or naturally occurring variants, analogs and derivatives hereof (including rapamycin) which retain at least the (substituted or unsubstituted) C2 through C15 portion of the ring structure of FK506 and are capable of binding with a natural or modified FKBP, preferably with a Kd value below about $10^{-6}$ M.

This invention further encompasses homo- and heterodimers and higher order oligomers containing one or more of such FK506-type compounds covalently linked to a linker moiety of this invention. Monomers of these FK506-type compounds are also of interest, whether or not covalently attached to a linker moiety or otherwise modified without abolishing their binding affinity for the corresponding FKBP. Such monomeric compounds may be used as oligomerization antagonist reagents, i.e., as antagonists for oligomerizing reagents based on a like FK506-type compound. Preferably the compounds and oligomers comprising them in accordance with this invention bind to natural, or preferably mutant, FKBPs with an affinity at least 0.1% and preferably at least about 1% and even more preferably at least about 10% as great as the affinity of FK506 for FKBP12. See e.g. Holt et al, infra.

Receptor domains for these and other ligands of this invention may be obtained by structure-based, site-directed or random mutagenesis methods. We contemplate a family of FKBP12 moieties which contain Val, Ala, Gly, Met or other small amino acids in place of one or more of Tyr26, Phe36, Asp37, Tyr82 and Phe99 as receptor domains for FK506-type and FK520-type ligands containing modifications at C9 and/or C10. In particular, we contemplate using FKBP's with small replacements such as Gly or Ala for Asp37 in conjunction with FK506-type and FK520-type ligands containing substituents at C10 (e.g., —NHCOR, where R is alkyl, preferably lower alkyl such as methyl for example; or —NHCHO), and FKBP's with small replacements such as Gly or Ala for Phe36, Phe99 and Tyr26 in conjunction with FK506-type and FK520-type ligands containing replacements at C9 (e.g., oxazalines or imines).

Site-directed mutagenesis may be conducted using the megaprimer mutagenesis protocol (see e.g., Sakar and Sommer, *BioTechniques* 8 4 (1990): 404–407). cDNA sequencing is performed with the Sequenase kit. Expression of mutant FKBP12s may be carried out in the plasmid pHN1+ in the *E. coli* strain XA90 since many FKBP12 mutants have been expressed in this system efficiently. Mutant proteins may be conveniently purified by fractionation over DE52 anion exchange resin followed by size exclusion on Sepharse as described elsewhere. See e.g. Aldape et al, *J Biol Chem* 267 23 (1992): 16029–32 and Park et al, *J Biol Chem* 267 5 (1992): 3316–3324. Binding constants may be readily determined by one of two methods. If the mutant FKBPs maintain sufficient rotamase activity, the standard rotamase assay may be utilized. See e.g., Galat et al. *Biochemistry* 31 (1992): 2427–2434. Otherwise, the mutant FKBP12s may be subjected to a binding assay using LH20 resin and radiolabeled $^3H_2$-dihydroFK506 and $^3H_2$-dihyroCsA that we have used previously with FKBPs and cyclophilins. Bierer et al, *Proc. Nat. Aca. Sci. U.S.A.* 87 4 (1993): 555–69.

(B) Selection of Compensatory Mutations in FKBP12 for Bump-FK506s Using the Yeast Two-Hybrid System One approach to obtaining variants of receptor proteins or domains, including of FKBP12, is the yeast "two-hybrid" or "interaction trap" system. The two-hybrid system has been used to detect proteins that interact with each other. A "bait" fusion protein consisting of a target protein fused to a transcriptional activation domain is co-expressed with a cDNA library of potential "hooks" fused to a DNA-binding domain. A protein-protein (bait-hook) interaction is detected by the appearance of a reporter gene product whose synthesis requires the joining of the DNA-binding and activation domains. The yeast two-hybrid system mentioned here was originally developed by Elledge and co-workers. Durfee et al, Genes & Development 7 4 (1993): 555–69 and Harper et al, Cell 75 4 (1993): 805–816.

Since the two-hybrid system per se cannot provide insights into receptor-ligand interactions involving small molecule organic ligands, we have developed a new, FK1012-inducible transcriptional activation system (discussed below). Using that system one may extend the two hybrid system so that small molecules (e.g., FK506s or FK1012s or FK506-type molecules of this invention) can be investigated. One first generates a cDNA library of mutant FKPs (the hooks) with mutations that are regionally localized to sites that surround C9 and C10 of FK506. For the bait, two different strategies may be pursued the first uses the ability of FK506 to bind to FKBP12 and create a composite surface that binds to calcineurin. The sequence-specific transcriptional activator is thus comprised of: DNA-binding domain-mutant FKBP12-bump-FK506-calcineurin A-activation domain (where—refers to a noncovalent binding interaction). The second strategy uses the ability of FK1012s to bind two FKBPs simultaneously. A HED version of an FK1012 may be used to screen for the following ensemble: DNA-binding domain-mutant FKBP12-bump-FK506-normal FK506-wildtype FKBP12-activation domain.

1. Calcineurin-GAL4 activation domain fusion as a bait: A derivative of pSE1107 that contains the GAL4 activation domain and calcineurin. A subunit fusion construct has been constructed. Its ability to act as a bait in the proposed manner has been verified by studies using the two-hybrid system to map out calcineurin's FKBP-FK506 binding site.

2. hFKBP12-GAL4 activation domain fusion as a bait: hFKBP12 cDNA may be excised as an EcoRI-HindIII fragment that covers the entire open reading frame, blunt-ended and ligated to the blunt-ended XhoI site of pSE1107 to generate the full-length hFKBP-GAL4 activation domain protein fusion.

3. Mutant hFKBP12 cDNA libraries hFKBP12 may be digested with EcoRI and HindIll, blunted and cloned into pAS1 (Durfee et al, supra) that has been cut with NcoI and blunted. This plasmid is further digested with NdeI to eliminate the NdeI fragment between the NdeI site in the polylinker sequence of pAS1 and the 5' end of hFKBP12 and religated. This generated the hFKBP12-GAL4 DNA binding domain protein fusion. hFKBP was reamplified with primers #11206 and #11210, Primer Table (SEQ ID NOs: 67–76);

```
11206              NdeI
5NdFK:   5'-GGAATTTC CAT ATG GGC GTG CAG G-3'
                     H   M   G   V   Q

11207              SmaI
3SmFK37: 5'-CTGTC CCG GGA NNN NNN NNN TTT CTT TCC ATC TTC AAG C-:
                  R   S   X   X   X   K   K   G   D   E   L

11208              SmaI
3SmFK27: 5'-CTGTC CCG GGA GGA ATC AAA TTT CTT TCC ATC TTC AAG CA⁻
                  R   S   S   D   F   K   K   G   D   E   L   M

NNN NNN NNN GTG CAC CAC GCA GG-3'
             X   X   X   H   V   V   C

11209              BamHI
38mFK98: 5'-CGC GGA TCC TCA TTC CAG TTT TAG AAG CTC CAC ATC NNN
                     END E   L   K   L   L   E   V   D   X

NNN NNN AGT GGC ATG TGG-3'
             X   X   T   A   H   P

11210              BamHI
38mFK:   5'-CGC GGA TCC TCA TTC CAG TTT TAG AAG C-3'
                     END E   L   K   L   L
```

Primer Table: Primers used in the construction of a regionally localized hFKBP12 cDNA library for use in screening for compensatoy mutations.

Mutant hFKBP12 cDNA fragments were then prepared using the primers listed below that contain randomized mutant sequences of hFKBP at defined positions by the polymerase chain reaction, and were inserted into the GAL4 DNA binding domain-hFKBP(NdeI/BamHI) construct.

4. Yeast strain S. cerevisiae Y153 carries two selectable marker genes (his3/β-galactosidase) that are integrated into the genome and are driven by GAL4 promoters. (Durfee, supra.).

Using Calcineurin GAL4 Activation Domain as Bait. The FKBP12-FK506 complex binds with high affinity to calcineurin, a type 2B protein phosphatase. Since we use C9- or C10-bumped ligands to serve as a bridge in the two-hybrid system, only those FKBPs from the cDNA library that contain a compensatory mutation generate a transcriptional activator. For convenience, one may prepare at least three distinct libraries (using primers 11207–11209, Primer Table) that will each contain 8,000 mutant FKBP12s. Randomized sites were chosen by inspecting the FKBP12-FK506 structure, which suggested clusters of residues whose mutation might allow binding of the offending C9 or C10 substituents on bumped FK506s. The libraries are then individually screened using both C9- and C10-bumped. The interaction between a bumped-FK506 and a compensatory hFKBP12 mutant can be detected by the ability of host yeast to grow on his dropout medium and by the expression of β-galactosidase gene. Since this selection is dependent on the presence of the bumped-FK506, false positives can be eliminated by substractive screening with replica plates that are supplemented with or without the bumped-FK506 ligands.

Using hFKBP12-GAL4 Activation Domain as Bait Using the calcineurin A-GAL4 activation domain to screen hFKBP12 mutant cDNA libraries is a simple way to identify compensatory mutations on FKBP12. However, mutations that allow bumped-FK506s to bind hFKBP12 may disrupt the interaction between the mutant FKBP12-bumped-FK506 complex and calcineurin. If the initial screening with calcineurin as a bait fails, the wild type hFKBP12-GAL4 activation domain will instead be used. An FK1012 HED reagent consisting of native-FK506-bumped-FK506 (FIG. 16) may be synthesized and used as a hook. The FK506 moiety of the FK1012 can bind the FKBP12-GAL4 activation domain. An interaction between the bumped-FK506 moiety of the FK1012 and a compensatory mutant of FKBP12 will allow host yeast to grow on this drop-out medium and to express β-galactosidase. In this way, the selection is based solely on the ability of hFKBP12 mutant to interact with the bumped-FK506. The same substractive screening strategy can be used to eliminate false positives.

In addition to the in vitro binding assays discussed earlier, an in vivo assay may be used to determine the binding affinity of the bumped-FK506s to the compensatory hFKBP12 mutants. In the yeast two-hybrid system, β-gal activity is determined by the degree of interaction between the "bait" and the "prey". Thus, the affinity between the bumped-FK506and the compensatory FKBP12 mutants can be estimated by the corresponding β-galactosidase activities produced by host yeasts at different HED (native-FK506-bumped-FK506) concentrations.

Using the strategy, additional randomized mutant FKBP12 cDNA libraries may be created in other bump-contact residues with low-affinity compensatory FKBP12 mutants as templates and may be screened similarly.

Phage Display Screening for High-Affinity Compensatory FKBP Mutations

Some high-affinity hFKBP12 mutants for bump-FK506 may contain several combined point mutations at discrete regions of the protein. The size of the library that contains appropriate combined mutations can be too large for the yeast two-hybrid systems capacity (e.g., >$10^8$ mutations). The use of bacteriophage as a vehicle for exposing whole functional proteins should greatly enhance the capability for screening a large numbers of mutations. See e.g. Bass et al, Proteins: Structure, Function & Genetics 8 4 (1990): 309–14; McCafferty et al, Nature 348 6301 (1990): 552–4; and Hoogenboom, Nucl Acids Res 19 15 (1991): 4133–7. If the desired high-affinity compensatory mutants is not be identified with the yeast two-hybrid system, a large number of combined mutations can be created on hFKBP12 with a phage vector as a carrier. The mutant hFKBP12 fusion phages can be screened with bumped-FK506-Sepharose as an affinity matrix, which can be synthesized in analogy to our original FK506-based affinity matrices. Fretz et al, J Am Chem Soc 113 4 (1991): 1409–1411. Repeated rounds of binding and phage amplification should lead to the identification of high-affinity compensatory mutants.

(C) Synthesis of "Bumped (CsA)2s": Modification of MeVal(11)CsA

As detailed above, we have demonstrated the feasibility of using cyclophilin as a dimerization domain and (CsA)2 as a HOD reagent in the context of the cell death signaling pathway. However, to further optimize the cellular activity of the (CsA)2 reagent one may rely upon similar strategies as described with FK1012s. Thus, modified (bumped) CsA-based oligomerizing reagents should be preferred in applications where it is particularly desirable for the reagent to be able to differentiate its target, the artificial protein constructs, from endogenous cyclophilins.

One class of modified CsA derivatives of this invention are CsA analogs in which (a) NMeVal11 is replaced with NMePhe (which maybe substituted or unsubstituted) or NMeThr (which may be unsubstituted or substituted on the threonine betahydroxyl group) or (b) the pro-S methyl group of NMeVal11 is replaced with a bulky group of at least 2 carbon atoms, preferably three or more, which may be straight branched and/or contain a cyclic moiety, and may be alkyl (ethyl, or preferably propyl, butyl, including t-butyl, and so forth), aryl, or arylalkyl. These compounds include those CsA analogs which contain NMeLeu, NMeIle, NMe-Phe or specifically the unnatural NMe[betaMePhe], in place of MeVal11. The "(b)"CsA compounds are of formula 2 where R represents a functional group as discussed above.

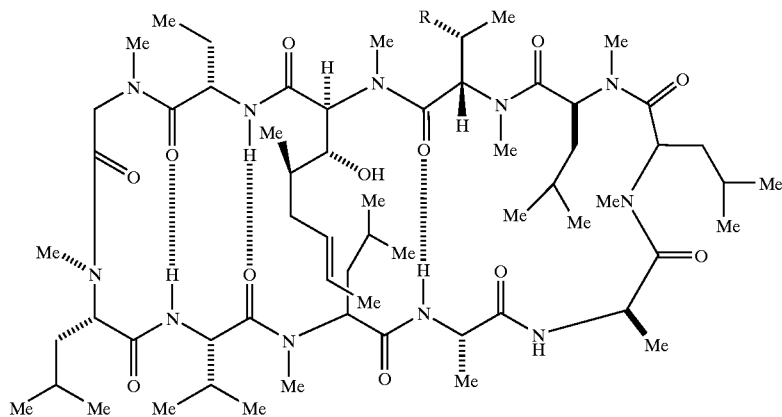

1 (R = Me):CsA
2 (R ≠ M):Modified [MeVal¹¹]CsA

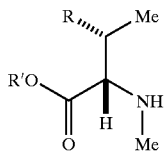

This invention further encompasses homo- and hetero-dimers and higher order oligomers containing one or more such CsA analogs. Preferably the compounds and oligomers comprising them in accordance with this invention bind to natural, or preferably mutant, cyclophilin proteins with an affinity at least 0.1% and preferably at least about 1% and even more preferably at least about 10% as great as the affinity of CsA for cyclophilin.

A two step strategy may be used to prepare the modified [MeVal¹¹]CsA derivatives starting from CsA. In the first step the residue MeVal11 is removed from the macrocycle. In the second step a selected amino acid is introduced at the (former) MeVal11 site and the linear peptide is cyclized. The advantage of this strategy is the ready access to several modified [MeVal¹¹]CsA derivatives in comparison with a total synthesis. The synthetic scheme is as follows:

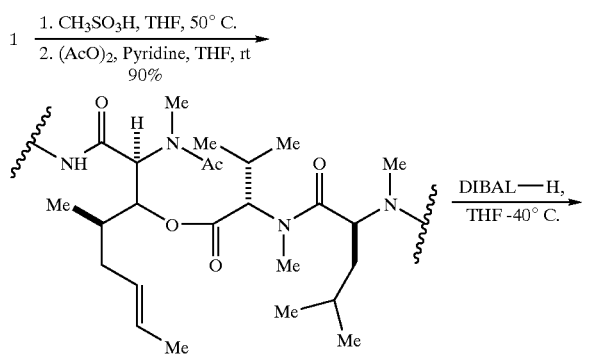

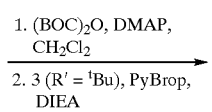

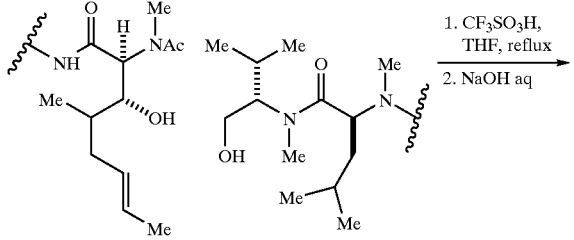

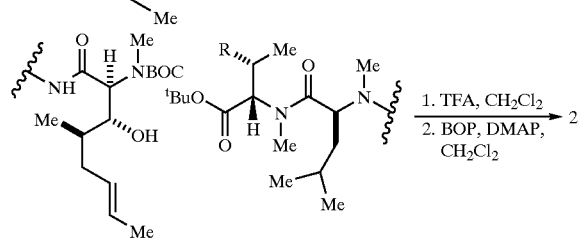

To differentiate the amide bonds, an N,O shift has been achieved between the amino and the hydroxyl groups from MeBmt1 to give IsoCsA (Ruegger et al, Helv Chim Acta 59 4 (1976): 1075–92) (see scheme above). The reaction was carried out in THF in the presence of methanesulfonic acid. (Oliyai et al, Pharm Res 9 5 (1992): 617–22). The free amine was protected with an acetyl group with pyridine and acetic anhydride in a one-pot procedure. The overall yield of the N-acetyl protected IsoCsA is 90%. The ester MeBmt1-MeVal11 bond is then reduced selectively in the presence of the N-methyl amide bonds, e.g. using DIBAL-H. The resulting diol is then transformed to the corresponding di-ester with another acid-induced N,O shift. This will prepare both the N-acetyl group and MeVal11 residues for removal through hydrolysis of the newly formed esters with aqueous base.

After protection of the free amino group the new amino acid residue is introduced e.g. with the PyBrop coupling agent. Deprotection and cyclization of the linear peptide with BOP in presence of DMAP (Alberg and Schreiber, Science 262 5131 (1993): 248–250) completes the synthesis of 2. The binding of bumped-CsAs to cyclophilins can be evaluated by the same methods described for FK506s and FK1012s. Once cyclophilins are identified with compensatory mutations, bumped (CsA)2 HED and HOD reagents may be synthesized according to the methods discussed previously. Of particular interest are bumped CsA compounds which can for dimers which themselves can bind to a cyclophilin protein with 1:2 stoichiometry. Homo dimers and higher order homo-oligomers, heterodimers and hetero-higher order oligomers containing at least one such CsA or modified CsA moiety may be designed and evaluated by the methods developed for FK1012A and (CsA)2, and optimize the linker element in analogy to the FK1012 studies.

Mutant cyclophilins that bind our position 11 CsA variants (2) by accommodating the extra bulk on the ligand may be new be prepared. Cyclophilins with these compensatory mutations may be identified through the structure-based site-directed and random mutagenesis/screening protocols described in the FK1012 studies.

It is evident from the above results, that the subject method and compositions provide for great versatility in the production of cells for a wide variety of purposes. By employing the subject constructs, one can use cells for therapeutic purposes, where the cells may remain inactive until needed, and then be activated by administration of a safe drug. Because cells can have a wide variety of lifetimes in a host, there is the opportunity to treat both chronic and acute indications so as to provide short- or long-term protection. In addition, one can provide for cells which will be directed to a particular site, such as an anatomic site or a functional site, where therapeutic effect may be provided.

Cells can be provided which will result in secretion of a wide variety of proteins, which may serve to correct a deficit or inhibit an undesired result, such as activation of cytolytic cells, to inactivate a destructive agent, to kill a restricted cell population, or the like. By having the cells present in the host over a defined period of time, the cells may be readily activated by taking the drug at a dose which can result in a rapid response of the cells in the host. Cells can be provided where the expressed chimeric receptor is intracellular, avoiding any immune response due to a foreign protein on the cell surface. Furthermore, the intracellular chimeric receptor protein provides for efficient signal transduction upon ligand binding, apparently more efficiently than the receptor binding at an extracellular receptor domain.

By using relatively simple molecules which bind to chimeric membrane bound receptors, resulting in the expression of products of interest or inhibiting the expression of products, one can provide for cellular therapeutic treatment. The compounds which may be administered are safe, can be administered in a variety of ways and can ensure a very specific response so as not to upset homeostasis.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. A recombinant chimeric protein comprising at least one ligand-binding domain which binds to a selected ligand and an action domain which is heterologous with respect to the ligand-binding domain, wherein the selected ligand binds to the ligand-binding domain and to a ligand-binding domain of another protein to form a ligand cross-linked complex with the two protein molecules, and further has one or more of the following characteristics:

(i) the ligand is not a protein;
(ii) the ligand has a molecular weight less than 5 kD; and
(iii) the ligand is membrane permeable; and wherein the action domain induces apoptosis in a cell following formation of the ligand cross-linked complex.

2. The chimeric protein of claim 1, wherein the chimeric protein comprises two or more ligand-binding domains.

3. The chimeric protein of claim 1, wherein the chimeric protein comprises at least one ligand-binding domain which binds to a ligand having a molecular weight less than 3 kD.

4. The chimeric protein of claim 1, wherein the chimeric protein comprises at least one ligand-binding domain having between 50 and 350 amino acid residues.

5. The chimeric protein of claim 1, wherein the chimeric protein comprises at least one naturally-occurring ligand binding domain.

6. The chimeric protein of claim 1, wherein the chimeric protein comprises at least one ligand-binding domain comprising a non-naturally-occurring peptide sequence.

7. The chimeric protein of claim 1, wherein the chimeric protein binds to the selected ligand with a kD value less than or equal to about $10^{-6}$ M.

8. The chimeric protein of claim 1, wherein the chimeric protein comprises at least one ligand binding domain comprising an immunophilin domain.

9. The chimeric protien of claim 1, wherein the chimeric protein comprises at least one ligand-binding domain which binds to FK506, FK520, or derivatives thereof.

10. The chimeric protein of claim 1, wherein the action domain comprises a cytoplasmic portion of a Fas or TNF receptor sufficient to induce apoptosis in a cell following formation of the ligand cross-linked complex.

11. The chimeric protein of claim 1, wherein the action domain comprises a cytoplasmic domain of a receptor which induces apoptosis.

12. The chimeric protein of claim 1, wherein said ligand is a synthetic organic molecule having a molecular weight of less than 5 kDa.

* * * * *

UNITED STATES PATENT AND TRADEMARK OFFICE
CERTIFICATE OF CORRECTION

| | | |
|---|---|---|
| PATENT NO. | : 6,891,021 B2 | Page 1 of 1 |
| APPLICATION NO. | : 10/054712 | |
| DATED | : May 10, 2005 | |
| INVENTOR(S) | : Crabtree et al. | |

It is certified that error appears in the above-identified patent and that said Letters Patent is hereby corrected as shown below:

In the Specification:

At column 1, line 20: Insert

GOVERNMENT SUPPORT
This invention was made with Government support under contract CA039612 awarded by the National Institutes of Health. The Government has certain rights to the invention.

Signed and Sealed this

Twenty-first Day of November, 2006

JON W. DUDAS
*Director of the United States Patent and Trademark Office*

```
                        SEQUENCE LISTING (1) GENERAL INFORMATION:

(iii) NUMBER OF SEQUENCES: 81

(2) INFORMATION FOR SEQ ID NO: 1:

(i) SEQUENCE CHARACTERISTICS:
          (A) LENGTH: 14 amino acids
          (B) TYPE: amino acid
          (D) TOPOLOGY: linear (ii) MOLECULE TYPE: peptide (xi) SEQUENCE DESCRIPTION: SEQ ID NO: 1:

Met Gly Ser Ser Lys Ser Lys Pro Lys Asp Pro Ser Gln Arg
  1               5                  10

(2) INFORMATION FOR SEQ ID NO: 2:

(i) SEQUENCE CHARACTERISTICS:
          (A) LENGTH: 11 base pairs
          (B) TYPE: nucleic acid
```

```
            (C) STRANDEDNESS: single
            (D) TOPOLOGY: linear (ii) MOLECULE TYPE: cDNA (xi) SEQUENCE DESCRIPTION: SEQ ID NO: 2:

GTTAAGTTAA C                                                                11

(2) INFORMATION FOR SEQ ID NO: 3:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 3:

TGACTCAGCG C                                                                11

(2) INFORMATION FOR SEQ ID NO: 4:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: misc_feature
            (B) LOCATION: 6..11
            (D) OTHER INFORMATION: /note= "Sac II restriction site."

(ix) FEATURE:
            (A) NAME/KEY: misc_signal
            (B) LOCATION: 12..16
            (D) OTHER INFORMATION: /note= "Kozak sequence."

(ix) FEATURE:
            (A) NAME/KEY: CDS
            (B) LOCATION: 17..31

(ix) FEATURE:
            (A) NAME/KEY: misc_feature
            (B) LOCATION: 17..33
            (D) OTHER INFORMATION: /note= "Region of homology with
                target sequence."

(xi) SEQUENCE DESCRIPTION: SEQ ID NO: 4:

CGACACCGCG GCCACC ATG GCC ACA ATT GGA GC                                    33
                  Met Ala Thr Ile Gly
                   1               5

(2) INFORMATION FOR SEQ ID NO: 5:

(i) SEQUENCE CHARACTERISTICS:
            (A) LENGTH: 5 amino acids
            (B) TYPE: amino acid
            (D) TOPOLOGY: linear (ii) MOLECULE TYPE: protein (xi) SEQUENCE DESCRIPTION: SEQ ID NO: 5:

Met Ala Thr Ile Gly
 1               5

(2) INFORMATION FOR SEQ ID NO: 6:
```

```
    (i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 6..11
        (D) OTHER INFORMATION: /note= "Xho I restriction site."

(ix) FEATURE:
        (A) NAME/KEY: misc_feature
        (B) LOCATION: 12..27
        (D) OTHER INFORMATION: /note= "Region of homology with
            target sequence."

(xi) SEQUENCE DESCRIPTION: SEQ ID NO: 6:

CGACACTCGA GAGCCCATGA CTTCTGG                                                27

(2) INFORMATION FOR SEQ ID NO: 7:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..4
        (D) OTHER INFORMATION: /note= "Translation product of
            complement of SEQ ID NO:6, bases 9 to 20."

(xi) SEQUENCE DESCRIPTION: SEQ ID NO: 7:

Ser Trp Ala Leu
1

(2) INFORMATION FOR SEQ ID NO: 8:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 6..11
        (D) OTHER INFORMATION: /note= "Xho I restriction site."

(ix) FEATURE:
        (A) NAME/KEY: misc_feature
        (B) LOCATION: 12..41
        (D) OTHER INFORMATION: /note= "Region of homology with
            target sequence."

(ix) FEATURE:
        (A) NAME/KEY: CDS
        (B) LOCATION: 9..41

(ix) FEATURE:
        (A) NAME/KEY: misc_feature
        (B) LOCATION: 28
        (D) OTHER INFORMATION: /note= "A to G."

(xi) SEQUENCE DESCRIPTION: SEQ ID NO: 8:

CGACACTC GAG CTC TGC TAC TTG CTA GGT GGA ATC CTC TTC                         41
```

```
          Glu Leu Cys Tyr Leu Leu Gly Gly Ile Leu Phe
            1               5                  10
```

(2) INFORMATION FOR SEQ ID NO: 9:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO: 9:

```
Glu Leu Cys Tyr Leu Leu Gly Gly Ile Leu Phe
  1               5                  10
```

(2) INFORMATION FOR SEQ ID NO: 10:

(i) SEQUENCE CHARACTERISTICS:
        (A) LENGTH: 24 base pairs
        (B) TYPE: nucleic acid
        (C) STRANDEDNESS: single
        (D) TOPOLOGY: /note= "Translational stop encoded
            in complementary strand."

(ii) MOLECULE TYPE: cDNA (ix) FEATURE:
        (A) NAME/KEY: misc_feature
        (B) LOCATION: 3..8
        (D) OTHER INFORMATION: /note= "Eco RI restriction site."

(ix) FEATURE:
        (A) NAME/KEY: misc_feature
        (B) LOCATION: 9..24
        (D) OTHER INFORMATION: /note= "Region of homology with
            target sequence."

(ix) FEATURE:
        (A) NAME/KEY: misc_feature
        (B) LOCATION: 24
        (D) OTHER INFORMATION: /note= "G to C."

(ix) FEATURE:
        (A) NAME/KEY: misc_signal
        (B) LOCATION: complement (9..11)

(xi) SEQUENCE DESCRIPTION: SEQ ID NO: 10:

```
GCGAATTCTT AGCGAGGGGC CAGC                                              24
```

(2) INFORMATION FOR SEQ ID NO: 11:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..4
        (D) OTHER INFORMATION: /note= "Translational product of
            complement to SEQ ID NO:10, bases 12 to 23."

(xi) SEQUENCE DESCRIPTION: SEQ ID NO: 11:

```
Leu Ala Pro Arg
  1
```

(2) INFORMATION FOR SEQ ID NO: 12:

```
    (i) SEQUENCE CHARACTERISTICS:
        (A) LENGTH: 33 base pairs
        (B) TYPE: nucleic acid
        (C) STRANDEDNESS: single
        (D) TOPOLOGY: /note= "Translational stop signal
            encoded on complementary strand."

(ii) MOLECULE TYPE: cDNA (ix) FEATURE:
        (A) NAME/KEY: misc_feature
        (B) LOCATION: 3..8
        (D) OTHER INFORMATION: /note= "Eco RI restriction."

(ix) FEATURE:
        (A) NAME/KEY: misc_feature
        (B) LOCATION: 12..17
        (D) OTHER INFORMATION: /note= "Sal I restriction site."

(ix) FEATURE:
        (A) NAME/KEY: misc_signal
        (B) LOCATION: complement (9..11)

(xi) SEQUENCE DESCRIPTION: SEQ ID NO: 12:

GCGAATTCTT AGTCGACGCG AGGGGCCAGG GTC                                             33

(2) INFORMATION FOR SEQ ID NO: 13:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..4
        (D) OTHER INFORMATION: /note= "Translational product of
            complement to SEQ ID NO:12, bases 18 to 29."

(xi) SEQUENCE DESCRIPTION: SEQ ID NO: 13:

Leu Ala Pro Arg
  1

(2) INFORMATION FOR SEQ ID NO: 14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 4..9
        (D) OTHER INFORMATION: /note= "Xho I restriction site."

(ix) FEATURE:
        (A) NAME/KEY: misc_feature
        (B) LOCATION: 13
        (D) OTHER INFORMATION: /note= "T to G."

(ix) FEATURE:
        (A) NAME/KEY: misc_feature
        (B) LOCATION: 4..25
        (D) OTHER INFORMATION: /note= "Region of homology with
            target sequence."

(ix) FEATURE:
        (A) NAME/KEY: CDS
        (B) LOCATION: 10..24
```

(xi) SEQUENCE DESCRIPTION: SEQ ID NO: 14:

```
GGGCTCGAG CTC GGC TAC TTG CTA G                                    25
          Leu Gly Tyr Leu Leu
          1               5
```

(2) INFORMATION FOR SEQ ID NO: 15:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO: 15:

```
Leu Gly Tyr Leu Leu
 1               5
```

(2) INFORMATION FOR SEQ ID NO: 16:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 6..11
        (D) OTHER INFORMATION: /note= "Xho I restriction site."

(ix) FEATURE:
        (A) NAME/KEY: misc_feature
        (B) LOCATION: 12..26
        (D) OTHER INFORMATION: /note= "Region of homology with
            target sequence."

(xi) SEQUENCE DESCRIPTION: SEQ ID NO: 16:

```
CGACACTCGA GGTGACGGAC AAGGTC                                       26
```

(2) INFORMATION FOR SEQ ID NO: 17:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 6..11
        (D) OTHER INFORMATION: /note= "Sal I restriction site."

(ix) FEATURE:
        (A) NAME/KEY: misc_feature
        (B) LOCATION: 12..26
        (D) OTHER INFORMATION: /note= "Region of homology with
            target sequence."

(xi) SEQUENCE DESCRIPTION: SEQ ID NO: 17:

```
CGACAGTCGA CCCAATCAGG GACCTC                                       26
```

(2) INFORMATION FOR SEQ ID NO: 18:

(i) SEQUENCE CHARACTERISTICS:
        (A) LENGTH: 33 base pairs

```
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: misc_feature
            (B) LOCATION: 1..5
            (D) OTHER INFORMATION: /note= "Xho I restriction site."

(ix) FEATURE:
            (A) NAME/KEY: misc_feature
            (B) LOCATION: 10..15
            (D) OTHER INFORMATION: /note= "Bsi WI restriction site."

(ix) FEATURE:
            (A) NAME/KEY: CDS
            (B) LOCATION: 6..32

(xi) SEQUENCE DESCRIPTION: SEQ ID NO: 18:

TCGAG TAT CCG TAC GAC GTA CCA GAC TAC GCA G                        33
      Tyr Pro Tyr Asp Val Pro Asp Tyr Ala
        1               5

(2) INFORMATION FOR SEQ ID NO: 19:

(i) SEQUENCE CHARACTERISTICS:
            (A) LENGTH: 9 amino acids
            (B) TYPE: amino acid
            (D) TOPOLOGY: linear (ii) MOLECULE TYPE: protein (xi) SEQUENCE DESCRIPTION: SEQ ID NO: 19:

Tyr Pro Tyr Asp Val Pro Asp Tyr Ala
  1               5

(2) INFORMATION FOR SEQ ID NO: 20:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: misc_feature
            (B) LOCATION: 1..5
            (D) OTHER INFORMATION: /note= "Sal I restriction site."

(xi) SEQUENCE DESCRIPTION: SEQ ID NO: 20:

TCGACTGCGT AGTCTGGTAC GTCGTACGGA TAC                               33

(2) INFORMATION FOR SEQ ID NO: 21:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: misc_feature
            (B) LOCATION: 1..5
            (D) OTHER INFORMATION: /note= "Sal I restriction site."

(xi) SEQUENCE DESCRIPTION: SEQ ID NO: 21:
```

```
TCGACTATCC GTACGACGTA CCAGACTACG CAC                                    33

(2) INFORMATION FOR SEQ ID NO: 22:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..5
        (D) OTHER INFORMATION: /note= "Xho I restriction site."

(xi) SEQUENCE DESCRIPTION: SEQ ID NO: 22:

TCGAGTGCGT AGTCTGGTAC GTCGTACGGA TAG                                    33

(2) INFORMATION FOR SEQ ID NO: 23:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 6..11
        (D) OTHER INFORMATION: /note= "Sac II restriction site."

(ix) FEATURE:
        (A) NAME/KEY: misc_signal
        (B) LOCATION: 12..16
        (D) OTHER INFORMATION: /note= "Kozak sequence."

(ix) FEATURE:
        (A) NAME/KEY: misc_signal
        (B) LOCATION: 17..58
        (D) OTHER INFORMATION: /note= "Myristoylation signal."

(ix) FEATURE:
        (A) NAME/KEY: misc_feature
        (B) LOCATION: 59..64
        (D) OTHER INFORMATION: /note= "Xho I restriction site."

(ix) FEATURE:
        (A) NAME/KEY: misc_feature
        (B) LOCATION: 65..80
        (D) OTHER INFORMATION: /note= "Zeta homology."

(ix) FEATURE:
        (A) NAME/KEY: CDS
        (B) LOCATION: 17..79

(xi) SEQUENCE DESCRIPTION: SEQ ID NO: 23:

CGACACCGCG GCCACC ATG GGG AGT AGC AAG AGC AAG CCT AAG GAC CCC           49
               Met Gly Ser Ser Lys Ser Lys Pro Lys Asp Pro
                 1               5                  10

AGC CAG CGC CTC GAG AGG AGT GCA GAG ACT G                               80
Ser Gln Arg Leu Glu Arg Ser Ala Glu Thr
             15                  20

(2) INFORMATION FOR SEQ ID NO: 24:

(i) SEQUENCE CHARACTERISTICS:
        (A) LENGTH: 21 amino acids
        (B) TYPE: amino acid
        (D) TOPOLOGY: linear
```

(ii) MOLECULE TYPE: protein (xi) SEQUENCE DESCRIPTION: SEQ ID NO: 24:

Met Gly Ser Ser Lys Ser Lys Pro Lys Asp Pro Ser Gln Arg Leu Glu
 1               5                  10                  15

Arg Ser Ala Glu Thr
            20

(2) INFORMATION FOR SEQ ID NO: 25:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 12..26

(ix) FEATURE:
        (A) NAME/KEY: misc_feature
        (B) LOCATION: 6..11
        (D) OTHER INFORMATION: /note= "Xho I restriction site."

(ix) FEATURE:
        (A) NAME/KEY: misc_feature
        (B) LOCATION: 12..27
        (D) OTHER INFORMATION: /note= "Region of homology with
            target sequence."

(xi) SEQUENCE DESCRIPTION: SEQ ID NO: 25:

CGACACTCGA G GAG CTC TGT GAC GAT G                                27
           Glu Leu Cys Asp Asp
            1               5

(2) INFORMATION FOR SEQ ID NO: 26:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO: 26:

Glu Leu Cys Asp Asp
 1               5

(2) INFORMATION FOR SEQ ID NO: 27:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 6..11
        (D) OTHER INFORMATION: /note= "Xho I restriction site."

(ix) FEATURE:
        (A) NAME/KEY: misc_feature
        (B) LOCATION: 12..41
        (D) OTHER INFORMATION: /note= "Region of homology with
            target sequence."

(ix) FEATURE:
            (A) NAME/KEY: misc_feature
            (B) LOCATION: 27..29
            (D) OTHER INFORMATION: /note= "GAT to AAG."

(ix) FEATURE:
            (A) NAME/KEY: CDS
            (B) LOCATION: 9..41

(xi) SEQUENCE DESCRIPTION: SEQ ID NO: 27:

CGACACTC GAG CTC TGC TAC TTG CTA AAG GGA ATC CTC TTC           41
         Glu Leu Cys Tyr Leu Leu Lys Gly Ile Leu Phe
          1               5                  10

(2) INFORMATION FOR SEQ ID NO: 28:

(i) SEQUENCE CHARACTERISTICS:
            (A) LENGTH: 11 amino acids
            (B) TYPE: amino acid
            (D) TOPOLOGY: linear (ii) MOLECULE TYPE: protein (xi) SEQUENCE DESCRIPTION: SEQ ID NO: 28:

Glu Leu Cys Tyr Leu Leu Lys Gly Ile Leu Phe
 1               5                  10

(2) INFORMATION FOR SEQ ID NO: 29:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: misc_feature
            (B) LOCATION: 6..11
            (D) OTHER INFORMATION: /note= "Xho I restriction site."

(ix) FEATURE:
            (A) NAME/KEY: CDS
            (B) LOCATION: 9..44

(ix) FEATURE:
            (A) NAME/KEY: misc_feature
            (B) LOCATION: 27..44
            (D) OTHER INFORMATION: /note= "Region of homology with
                target sequence."

(xi) SEQUENCE DESCRIPTION: SEQ ID NO: 29:

CGACACTC GAG CTG CTG GAT CCG AAG CTC TGC TAC TTG CTA AAG       44
         Glu Leu Leu Asp Pro Lys Leu Cys Tyr Leu Leu Lys
          1               5                  10

(2) INFORMATION FOR SEQ ID NO: 30:

(i) SEQUENCE CHARACTERISTICS:
            (A) LENGTH: 12 amino acids
            (B) TYPE: amino acid
            (D) TOPOLOGY: linear (ii) MOLECULE TYPE: protein (xi) SEQUENCE DESCRIPTION: SEQ ID NO: 30:

Glu Leu Leu Asp Pro Lys Leu Cys Tyr Leu Leu Lys
 1               5                  10

(2) INFORMATION FOR SEQ ID NO: 31:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 6..11
        (D) OTHER INFORMATION: /note= "Xho I restriction site."

(ix) FEATURE:
        (A) NAME/KEY: misc_feature
        (B) LOCATION: 12..31
        (D) OTHER INFORMATION: /note= "Region of homology with
            target sequence."

(ix) FEATURE:
        (A) NAME/KEY: CDS
        (B) LOCATION: 9..31

(xi) SEQUENCE DESCRIPTION: SEQ ID NO: 31:

```
CGACACTC GAG ACA ACA GAG TAC CAG GTA GC                           31
         Glu Thr Thr Glu Tyr Gln Val Ala
           1               5
```

(2) INFORMATION FOR SEQ ID NO: 32:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO: 32:

```
Glu Thr Thr Glu Tyr Gln Val Ala
  1               5
```

(2) INFORMATION FOR SEQ ID NO: 33:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 6..11
        (D) OTHER INFORMATION: /note= "Xho I restriction site."

(ix) FEATURE:
        (A) NAME/KEY: misc_feature
        (B) LOCATION: 12..28
        (D) OTHER INFORMATION: /note= "Region of homology with
            target sequence."

(ix) FEATURE:
        (A) NAME/KEY: CDS
        (B) LOCATION: 9..28

(xi) SEQUENCE DESCRIPTION: SEQ ID NO: 33:

```
CGACACTC GAG GGC GTG CAG GTG GAG AC                               28
         Glu Gly Val Gln Val Glu Thr
           1               5
```

(2) INFORMATION FOR SEQ ID NO: 34:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO: 34:

Glu Gly Val Gln Val Glu Thr
1              5

(2) INFORMATION FOR SEQ ID NO: 35:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 6..11
        (D) OTHER INFORMATION: /note= "Sal I restriction site."

(ix) FEATURE:
        (A) NAME/KEY: misc_feature
        (B) LOCATION: 12..27
        (D) OTHER INFORMATION: /note= "Region of homology with
            target sequence."

(ix) FEATURE:
        (A) NAME/KEY: CDS
        (B) LOCATION: complement (9..26)

(xi) SEQUENCE DESCRIPTION: SEQ ID NO: 35:

CGACAGTCGA CTTCCAGTTT TAGAAGC                        27

(2) INFORMATION FOR SEQ ID NO: 36:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO: 36:

Leu Leu Lys Leu Glu Val
1              5

(2) INFORMATION FOR SEQ ID NO: 37:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 7..12
        (D) OTHER INFORMATION: /note= "Xho I restriction site."

(ix) FEATURE:
        (A) NAME/KEY: CDS
        (B) LOCATION: 10..27

```
        (ix) FEATURE:
            (A) NAME/KEY: misc_feature
            (B) LOCATION: 13..27
            (D) OTHER INFORMATION: /note= "Region of homology with
                target sequence."

(xi) SEQUENCE DESCRIPTION: SEQ ID NO: 37:

TCGACACTC GAG ACG GGG GCC GAG GGC                                          27
          Glu Thr Gly Ala Glu Gly
            1               5

(2) INFORMATION FOR SEQ ID NO: 38:

(i) SEQUENCE CHARACTERISTICS:
            (A) LENGTH: 6 amino acids
            (B) TYPE: amino acid
            (D) TOPOLOGY: linear (ii) MOLECULE TYPE: protein (xi) SEQUENCE DESCRIPTION: SEQ ID NO: 38:

Glu Thr Gly Ala Glu Gly
  1               5

(2) INFORMATION FOR SEQ ID NO: 39:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: misc_feature
            (B) LOCATION: 7..12
            (D) OTHER INFORMATION: /note= "Sal I restriction site."

(ix) FEATURE:
            (A) NAME/KEY: CDS
            (B) LOCATION: complement (10..18)

(ix) FEATURE:
            (A) NAME/KEY: misc_feature
            (B) LOCATION: 13..28
            (D) OTHER INFORMATION: /note= "Region of homology with
                target sequence."

(xi) SEQUENCE DESCRIPTION: SEQ ID NO: 39:

CCGACAGTCG ACCTCTATTT TGAGCAGC                                             28

(2) INFORMATION FOR SEQ ID NO: 40:

(i) SEQUENCE CHARACTERISTICS:
            (A) LENGTH: 3 amino acids
            (B) TYPE: amino acid
            (D) TOPOLOGY: linear (ii) MOLECULE TYPE: protein (xi) SEQUENCE DESCRIPTION: SEQ ID NO: 40:

Ile Glu Val
  1

(2) INFORMATION FOR SEQ ID NO: 41:

(i) SEQUENCE CHARACTERISTICS:
            (A) LENGTH: 38 base pairs
            (B) TYPE: nucleic acid
            (C) STRANDEDNESS: single
```

(D) TOPOLOGY: linear (ii) MOLECULE TYPE: cDNA (xi) SEQUENCE DESCRIPTION: SEQ ID NO: 41:

CGACACCGCG GCCACCATGA AGCTACTGTC TTCTATCG                              38

(2) INFORMATION FOR SEQ ID NO: 42:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 42:

CGACAGTCGA CCGATACAGT CAACTGTC                                        28

(2) INFORMATION FOR SEQ ID NO: 43:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: misc_feature
            (B) LOCATION: 6..11
            (D) OTHER INFORMATION: /note= "Sac II restriction site."

(ix) FEATURE:
            (A) NAME/KEY: misc_signal
            (B) LOCATION: 12..16
            (D) OTHER INFORMATION: /note= "Kozak sequence."

(ix) FEATURE:
            (A) NAME/KEY: CDS
            (B) LOCATION: 17..37

(ix) FEATURE:
            (A) NAME/KEY: misc_feature
            (B) LOCATION: 17..38
            (D) OTHER INFORMATION: /note= "Gal4 (1-147) coding
                region."

(xi) SEQUENCE DESCRIPTION: SEQ ID NO: 43:

CGACACCGCG GCCACC ATG AAG CTA CTG TCT TCT ATC G                       38
                 Met Lys Leu Leu Ser Ser Ile
                  1               5

(2) INFORMATION FOR SEQ ID NO: 44:

(i) SEQUENCE CHARACTERISTICS:
            (A) LENGTH: 7 amino acids
            (B) TYPE: amino acid
            (D) TOPOLOGY: linear (ii) MOLECULE TYPE: protein (xi) SEQUENCE DESCRIPTION: SEQ ID NO: 44:

Met Lys Leu Leu Ser Ser Ile
 1               5

(2) INFORMATION FOR SEQ ID NO: 45:

(i) SEQUENCE CHARACTERISTICS:

```
            (A) LENGTH: 28 base pairs
            (B) TYPE: nucleic acid
            (C) STRANDEDNESS: double
            (D) TOPOLOGY: linear (ii) MOLECULE TYPE: cDNA (ix) FEATURE:
            (A) NAME/KEY: misc_feature
            (B) LOCATION: 1..17
            (D) OTHER INFORMATION: /note= "Region encoding for
                C-terminal end of Gal4 (1-147)."

(ix) FEATURE:
            (A) NAME/KEY: CDS
            (B) LOCATION: 3..17

(ix) FEATURE:
            (A) NAME/KEY: misc_feature
            (B) LOCATION: 18..23
            (D) OTHER INFORMATION: /note= "Sal I restriction site."

(xi) SEQUENCE DESCRIPTION: SEQ ID NO: 45:

GA CAG TTG ACT GTA TCG GTCGACTGTC G                                28
   Arg Gln Leu Thr Val Ser
    1               5

(2) INFORMATION FOR SEQ ID NO: 46:

(i) SEQUENCE CHARACTERISTICS:
            (A) LENGTH: 6 amino acids
            (B) TYPE: amino acid
            (D) TOPOLOGY: linear (ii) MOLECULE TYPE: protein (xi) SEQUENCE DESCRIPTION: SEQ ID NO: 46:

Arg Gln Leu Thr Val Ser
 1               5

(2) INFORMATION FOR SEQ ID NO: 47:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 47:

CGACACCGCG GCCACCATGG TTTCTAAGCT GAGC                              34

(2) INFORMATION FOR SEQ ID NO: 48:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 48:

CGACAGTCGA CCAACTTGTG CCGGAAGG                                     28

(2) INFORMATION FOR SEQ ID NO: 49:

(i) SEQUENCE CHARACTERISTICS:
            (A) LENGTH: 34 base pairs
            (B) TYPE: nucleic acid
```

```
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 6..11
        (D) OTHER INFORMATION: /note= "Sac II restriction site."

(ix) FEATURE:
        (A) NAME/KEY: misc_signal
        (B) LOCATION: 12..16
        (D) OTHER INFORMATION: /note= "Kozak sequence."

(ix) FEATURE:
        (A) NAME/KEY: CDS
        (B) LOCATION: 17..34

(ix) FEATURE:
        (A) NAME/KEY: misc_feature
        (B) LOCATION: 17..34
        (D) OTHER INFORMATION: /note= "Region encoding N-terminal
            end of HNF1 (1281)."

(xi) SEQUENCE DESCRIPTION: SEQ ID NO: 49:

CGACACCGCG GCCACC ATG GTT TCT AAG CTG AGC                              34
              Met Val Ser Lys Leu Ser
               1               5

(2) INFORMATION FOR SEQ ID NO: 50:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO: 50:

Met Val Ser Lys Leu Ser
 1               5

(2) INFORMATION FOR SEQ ID NO: 51:

(i) SEQUENCE CHARACTERISTICS:
        (A) LENGTH: 28 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: misc_feature
        (B) LOCATION: 1..20
        (D) OTHER INFORMATION: /note= "Region encoding for
            C-terminal end of HNF1 (1-282)."

(ix) FEATURE:
        (A) NAME/KEY: CDS
        (B) LOCATION: 3..17

(xi) SEQUENCE DESCRIPTION: SEQ ID NO: 51:

CC TTC CGG CAC AAG TTG GTCGACTGTC G                                    28
Ala Phe Arg His Lys Leu
 1               5

(2) INFORMATION FOR SEQ ID NO: 52:

(i) SEQUENCE CHARACTERISTICS:
        (A) LENGTH: 6 amino acids
        (B) TYPE: amino acid
```

(D) TOPOLOGY: linear (ii) MOLECULE TYPE: protein (xi) SEQUENCE DESCRIPTION: SEQ ID NO: 52:

Ala Phe Arg His Lys Leu
 1               5

(2) INFORMATION FOR SEQ ID NO: 53:

(i) SEQUENCE CHARACTERISTICS:
        (A) LENGTH: 11 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: misc_signal
        (B) LOCATION: 3..7
        (D) OTHER INFORMATION: /note= "Kozak sequence."

(ix) FEATURE:
        (A) NAME/KEY: misc_feature
        (B) LOCATION: 1..11
        (D) OTHER INFORMATION: /note= "Complementary to bases 5 to
            15 of SEQ ID NO:54."

(xi) SEQUENCE DESCRIPTION: SEQ ID NO: 53:

GGCCACCATG C                                                              11

(2) INFORMATION FOR SEQ ID NO: 54:

(i) SEQUENCE CHARACTERISTICS:
        (A) LENGTH: 3 amino acids
        (B) TYPE: amino acid
        (C) STRANDEDNESS: single
        (D) TOPOLOGY: linear (ix) FEATURE:
        (A) NAME/KEY: Peptide
        (B) LOCATION: 1..3
        (D) OTHER INFORMATION: /note= "Translation product of SEQ
            ID NO:53 and SEQ ID NO:55.  Translational start
            site at base 8 of SEQ ID NO:53."

(xi) SEQUENCE DESCRIPTION: SEQ ID NO: 54:

Met Leu Glu
 1

(2) INFORMATION FOR SEQ ID NO: 55:

(i) SEQUENCE CHARACTERISTICS:
        (A) LENGTH: 17 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: misc_feature
        (B) LOCATION: 14..17
        (D) OTHER INFORMATION: /note= "Sac II restriction site
            overhang."

(ix) FEATURE:
        (A) NAME/KEY: misc_feature
        (B) LOCATION: 1..5
        (D) OTHER INFORMATION: /note= "Xho I restriction site
            overhang."

(ix) FEATURE:
            (A) NAME/KEY: misc_feature
            (B) LOCATION: 5..15
            (D) OTHER INFORMATION: /note= "Complementary to bases 1 to
                11 of SEQ ID NO:53."

(xi) SEQUENCE DESCRIPTION: SEQ ID NO: 55:

TCGAGCATGG TGGCCGC                                                          17

(2) INFORMATION FOR SEQ ID NO: 56:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 56:

TCGACCCTAA GAMGAAGAGA AAGGTAC                                               27

(2) INFORMATION FOR SEQ ID NO: 57:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 57:

TCGAGTACCT TTCTCTTCKT CTTAGGG                                               27

(2) INFORMATION FOR SEQ ID NO: 58:

(i) SEQUENCE CHARACTERISTICS:
            (A) LENGTH: 27 base pairs
            (B) TYPE: nucleic acid
            (C) STRANDEDNESS: both
            (D) TOPOLOGY: linear (ii) MOLECULE TYPE: cDNA (ix) FEATURE:
            (A) NAME/KEY: misc_feature
            (B) LOCATION: 1..5
            (D) OTHER INFORMATION: /note= "Sal I restriction site
                overhang."

(ix) FEATURE:
            (A) NAME/KEY: misc_feature
            (B) LOCATION: 5..27
            (D) OTHER INFORMATION: /note= "Complementary to SEQ ID
                NO:60, bases 5 to 27."

(xi) SEQUENCE DESCRIPTION: SEQ ID NO: 58:

TCGACCCTAA GAAGAAGAGA AAGGTAC                                               27

(2) INFORMATION FOR SEQ ID NO: 59:

(i) SEQUENCE CHARACTERISTICS:
            (A) LENGTH: 11 amino acids
            (B) TYPE: amino acid
            (C) STRANDEDNESS: single
            (D) TOPOLOGY: linear (ix) FEATURE:
            (A) NAME/KEY: Peptide
            (B) LOCATION: 1..11

(D) OTHER INFORMATION: /note= "Translation product of SEQ
    ID NOS:58 and 60."

(xi) SEQUENCE DESCRIPTION: SEQ ID NO: 59:

Leu Asp Pro Lys Lys Lys Arg Lys Val Leu Glu
1               5                   10

(2) INFORMATION FOR SEQ ID NO: 60:

(i) SEQUENCE CHARACTERISTICS:
        (A) LENGTH: 27 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: misc_feature
        (B) LOCATION: 1..5
        (D) OTHER INFORMATION: /note= "Xho I restriction site
            overhang."

(ix) FEATURE:
        (A) NAME/KEY: misc_feature
        (B) LOCATION: 5..27
        (D) OTHER INFORMATION: /note= "Complementary to SEQ ID
            NO:58, bases 5 to 27."

(xi) SEQUENCE DESCRIPTION: SEQ ID NO: 60:

TCGAGTACCT TTCTCTTCTT CTTAGGG                                       27

(2) INFORMATION FOR SEQ ID NO: 61:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 61:

CGACAGTCGA CGCCCCCCCG ACCGATGTC                                     29

(2) INFORMATION FOR SEQ ID NO: 62:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 62:

CGACACTCGA GCCCACCGTA CTCGTC                                        26

(2) INFORMATION FOR SEQ ID NO: 63:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 6..11

(D) OTHER INFORMATION: /note= "Sal I restriction site."

(ix) FEATURE:
         (A) NAME/KEY: CDS
         (B) LOCATION: 12..29

(ix) FEATURE:
         (A) NAME/KEY: misc_feature
         (B) LOCATION: 12..29
         (D) OTHER INFORMATION: /note= "Region encoding N-terminal
             end of VP16 (413-490)."

(xi) SEQUENCE DESCRIPTION: SEQ ID NO: 63:

CGACAGTCGA C GCC CCC CCG ACC GAT GTC                          29
            Ala Pro Pro Thr Asp Val
             1           5

(2) INFORMATION FOR SEQ ID NO: 64:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO: 64:

Ala Pro Pro Thr Asp Val
 1           5

(2) INFORMATION FOR SEQ ID NO: 65:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (ii) MOLECULE TYPE: cDNA (ix) FEATURE:
         (A) NAME/KEY: CDS
         (B) LOCATION: 1..15

(ix) FEATURE:
         (A) NAME/KEY: misc_feature
         (B) LOCATION: 1..15
         (D) OTHER INFORMATION: /note= "Region encoding C-terminal
             end of VP16 (413-490)."

(xi) SEQUENCE DESCRIPTION: SEQ ID NO: 65:

GAC GAG TAC GGT GGG CTCGAGTGTC G                              26
Asp Glu Tyr Gly Gly
 1           5

(2) INFORMATION FOR SEQ ID NO: 66:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO: 66:

Asp Glu Tyr Gly Gly
 1           5

(2) INFORMATION FOR SEQ ID NO: 67:

(i) SEQUENCE CHARACTERISTICS:

(A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 67:

GGAATTCCAT ATGGGCGTGC AGG                                           23

(2) INFORMATION FOR SEQ ID NO: 68:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO: 68:

His Met Gly Val Gln
 1               5

(2) INFORMATION FOR SEQ ID NO: 69:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 69:

CTGTCCCGGG ANNNNNNNNN TTTCTTTCCA TCTTCAAGC                           39

(2) INFORMATION FOR SEQ ID NO: 70:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO: 70:

Arg Ser Xaa Xaa Xaa Lys Lys Gly Asp Glu Leu
 1               5                  10

(2) INFORMATION FOR SEQ ID NO: 71:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 71:

CTGTCCCGGG AGGAATCAAA TTTCTTTCCA TCTTCAAGCA NNNNNNNNNG TGCACCACGC    60

AGG                                                                 63

(2) INFORMATION FOR SEQ ID NO: 72:

(i) SEQUENCE CHARACTERISTICS:
        (A) LENGTH: 19 amino acids
        (B) TYPE: amino acid (D) TOPOLOGY: linear (ii) MOLECULE TYPE: peptide (xi) SEQUENCE DESCRIPTION: SEQ ID NO: 72:

Arg Ser Ser Asp Phe Lys Lys Gly Asp Glu Leu Met Xaa Xaa Xaa His
 1               5                  10                  15
Val Val Cys (2) INFORMATION FOR SEQ ID NO: 73:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 73:

CGCGGATCCT CATTCCAGTT TTAGAAGCTC CACATCNNNN NNNNNAGTGG CATGTGG                57

(2) INFORMATION FOR SEQ ID NO: 74:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO: 74:

Glu Leu Lys Leu Leu Glu Val Asp Xaa Xaa Xaa Thr Ala His Pro
 1               5                  10                  15

(2) INFORMATION FOR SEQ ID NO: 75:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 75:

CGCGGATCCT CATTCCAGTT TTAGAAGC                                                28

(2) INFORMATION FOR SEQ ID NO: 76:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO: 76:

Glu Leu Lys Leu Leu
 1               5

(2) INFORMATION FOR SEQ ID NO: 77:

(i) SEQUENCE CHARACTERISTICS:
        (A) LENGTH: 28 base pairs
        (B) TYPE: nucleic acid
        (C) STRANDEDNESS: single
        (D) TOPOLOGY: linear

```
    (ii) MOLECULE TYPE: cDNA (xi) SEQUENCE DESCRIPTION: SEQ ID NO: 77:

CGACAGTCGA CCGATACAGT CAACTGTC                                    28

(2) INFORMATION FOR SEQ ID NO: 78:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 78:

CGACAGTCGA CCAACTTGTG CCGGAAGG                                    28

(2) INFORMATION FOR SEQ ID NO: 79:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 79:

TCGAGCATGG TGGCCGC                                                17

(2) INFORMATION FOR SEQ ID NO: 80:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 80:

TCGAGTACCT TTCTCTTCTT CTTAGGG                                     27

(2) INFORMATION FOR SEQ ID NO: 81:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 81:

CGACACTCGA GCCCACCGTA CTCGTC                                      26
```